US 7,060,247 B2

(12) United States Patent
Hoffman et al.

(10) Patent No.: US 7,060,247 B2
(45) Date of Patent: *Jun. 13, 2006

(54) GASTRIN RECEPTOR-AVID PEPTIDE CONJUGATES

(75) Inventors: Timothy J. Hoffman, Columbia, MO (US); Wynn A. Volkert, Columbia, MO (US); Gary Sieckman, Ashland, MO (US); Charles J. Smith, Columbia, MO (US); Hariprasad Gali, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/847,134

(22) Filed: May 2, 2001

(65) Prior Publication Data

US 2002/0054855 A1 May 9, 2002

Related U.S. Application Data

(60) Continuation-in-part of application No. 09/537,423, filed on Mar. 29, 2000, now abandoned, which is a division of application No. 09/064,499, filed on Apr. 22, 1998, now Pat. No. 6,200,546

(60) Provisional application No. 60/044,049, filed on Apr. 22, 1997.

(51) Int. Cl.
*A61K 49/00* (2006.01)

(52) U.S. Cl. ............... 424/9.1; 424/1.11; 424/1.65; 424/1.69

(58) Field of Classification Search ............ 424/1.11, 424/1.65, 1.37, 9.1, 9.3, 9.4, 9.5, 9.6, 9.7, 424/1.69; 534/7, 10.16; 530/300, 333, 317, 530/309, 338, 324, 327; 206/569, 570; 514/14–16
See application file for complete search history.

(56) References Cited

U.S. PATENT DOCUMENTS

| | | | |
|---|---|---|---|
| 4,885,363 A | | 12/1989 | Tweedle et al. |
| 4,988,496 A | * | 1/1991 | Srinivasan et al. ......... 424/1.11 |
| 5,428,019 A | * | 6/1995 | Edwards et al. ............ 514/169 |
| 5,686,410 A | * | 11/1997 | Albert et al. ............... 514/12 |
| 6,200,546 B1 | * | 3/2001 | Hoffman et al. .............. 424/9.1 |

FOREIGN PATENT DOCUMENTS

| | | |
|---|---|---|
| WO | WO 91/01144 | 2/1991 |
| WO | WO 96/03427 | 2/1996 |

OTHER PUBLICATIONS

Bjisterbosch, M.K., et al., Selective Drug Delivery by Means of Receptor–Mediated Endocytosis, (1995) Quarterly J. Nucl. Med. 39:4–19.

Bushbaum, (1995) Pharmakokinetics of Antibodies and Their Radiolabels. In: Cancer Therapy with Radiolabeled Antibodies, (ed) D.M. Goldenberg, CRC Press, Boca Raton, Chapter 10, 115–140 FL.

Cai et al, Pseudononapeptide Bombesin Antagonists Containing C–Terminal Trp or Tpi, (1992) Peptides, 13:267–271.

Cai et al., Potent bombesin antagonists with C–terminal Leu–$\Psi(CH_2-N)$–Tac–$NH_2$ or its derivatives, (1994) Proc. Natl. Acad. Sci., 91:12664–12668.

Coy et al., Probing Peptide Backbone Function in Bombesin, (1988) J. Biolog. Chem., 263(11), 5056–5060.

Davis et al. Metabolic Stability and Tumor Inhibition of Bombesin/GRP Receptor Antagonists, (1992) Peptides, 13:401–407.

De Jong et al., Yttrium–90 and indium–111 labelling receptor binding and biodistribution of [$DOTA^0,_D$–$Phe^1$, $Tyr^3$] octreotide, a promising somatostatin analogue for radionuclide therapy, (1997) Eur. J. Nucl. Med., 24:368–371.

Duncan et al., Indium–111 Diethylenetriaminepentaacetic Acid–Octreotide Is Delivered in Vivo To Pancraetic, Tumor Cell, Renal, and Hepatocyte Lysosomes, (1997) Cancer Res. 57:659–671.

Eckelman Radiolabeling with technetium–99m to study high–capacity and low–capacity biochemical systems, (1995) Eur. J. Nucl. Med., 22:249–263.

Eckelman et al., (1993) The design of site–directed radiopharmaceuticals for use in drug discovery. In: Nuclear Imaging in Drug Discovery, Development and Approval (eds) H.D. Burns et al., Birkhauser Publ. Inc., Boston, MA.

Fischman et al., A Ticket to Ride: Peptide Radiopharmaceuticals, (1993) J. Nucl. Med., 34:2253–2263.

Fritzberg et al., Targeted Proteins for Diagnostic Imaging: Does Chemistry make a Difference?, (Mar. 1992) J. Nucl. Med., 33:394–397.

Frizberg et al. (1995) Radiolaeling of antibodies for targeted diagnostics. In: Targeted Delivery of Imaging Agents (ed) V.P. Torchilin, CRC Press, Boca Raton, FL, pp. 83–101.

(Continued)

*Primary Examiner*—Dameron L. Jones
(74) *Attorney, Agent, or Firm*—Kohn & Associates, PLLC

(57) ABSTRACT

A compound for use as a therapeutic or diagnostic radiopharmaceutical includes a group capable of complexing a medically useful metal attached to a moiety which is capable of binding to a gastrin releasing peptide receptor. A method for treating a subject having a neoplastic disease includes administering to the subject an effective amount of a radiopharmaceutical having a metal chelated with a chelating group attached to a-moiety capable of binding to a gastrin releasing peptide receptor expressed on tumor cells with subsequent internalization inside of the cell. A method of forming a therapeutic or diagnostic compound includes reacting a metal synthon with a chelating group covalently linked with a moiety capable of binding a gastrin releasing peptide receptor.

57 Claims, 32 Drawing Sheets

OTHER PUBLICATIONS

Gali, H., Hoffman, T.J., Owen, N.K., Sieckman, G.L., and Volkert, W.A., "In Vitro and In Vivo Evaluation of 111In_Labeled DOTA_8_Aoc_BBN[7_14]NH2 Conjugate for Specific Targeting of Tumors Expressing Gastrin Releasing Peptide (GRP) Receptors", 47th Annual Meeting—Society of Nuclear Medicine, St. Louis, MO, J.Nucl. Med., 41(5), 119P, #471, 2000.

Gali, H., Hoffman, T.J., Sieckman, G.L., Katti, K.V., and Volkert, W.A., "Synthesis, Characterization and Labeling with 99m Tc/188Re of Peptide Conjugates Containing a Dithio–Biosphosphine Chelating Agent" Bioconjugate Chemistry, 2001 12:354–363.

Gali, H., Smith, C.J., Hoffman, T.J., Sieckman, G.L., Hayes, D.L., Owen, N.K., and Volkert, W.A., "Influence of the Radiometal on the In Vivo Pharmacokinetic Properties of a Radiometal–labeled DOTA–Conjugated Peptide", 222nd American Chemical Society National Meeting, Chicago, IL, Aug., 2001 (Accepted).

Hermanson (1996) In: Bioconjugate Techniques, Functional Targets, Academic Press, pp. 3–136.

Hoffken, (ed) (1994) In: Peptides in Oncology II, Somatostatin Analogues: Mechanisms of Aciton, Springer–Verlag, Berlin–Heidelberg, 1–136.

Hoffman, T.J., Gali, H., Sieckman, G.L., Forte, L.R., Chin, D.T., Owen, N.K., Wooldridge, J.E., and Volkert, W.A., "Development and Characterization of a Receptor–Avid 111In–Labeled Peptide for Site–Specific Targeting of Colon Cancer", 92nd Annual Meeting of the American Association for Cancer Research, New Orleans, LA. Proceedings of the American Association for Cancer Research, vol. 42, 139, #746, Mar. 2001.

Hoffman, T.J., Li, N., Sieckman, G.L., Higginbotham, C., Ochrymoycz, L.A., Volkert, W.A., Rh–105 Bombesin Analogs: Selecive In Vivo Targeting of Prostate Cancer with a Therapeutic Radionuclide, 45$^{th}$ Annual Meeting–Society of Nuclear Medicine, Jun. 1998 J. Nucl. Med., 39(5), #982, 222P.

Hoffman, T.J., Li, N., Sieckman, G., and Volkert, W.A., "Uptake and Retention of a Rh–105 Labeled Bombesin Analogue in GRP Receptor Expressing Neoplasms: An In–Vitro Study", 44th Annual Meeting—Society of Nuclear Medicine, Jun., 1997;J.Nucl. Med., 38(5), 188P, 1997 #808.

Hoffman, T.J., Li, N., Sieckman, G., Higginbotham, C.A., and Volkert, W.A., "Evaluation of Radiolabeled (I–125 vs. Rh–105) Bombesin Analogue Internalization in Normal and Tumor Cell Lines", 10th International Symposium on Radiopharmacology, May, 1997: Quarterly J. Nucl. Med., 41(2) Suppl#1, 5, 1997.

Hoffman, T.J., Li, N., Volkert, W.A., Sieckman, G., Higginbotham, C.A., and Ochrymowycz, L.A., "Synthesis and Characterization of Rh–105 Labeled Bombesin Analogues: Enhancement of GRP Receptor Binding Affinity Utilizing Aliphatic Carbon Chain Linkers", 12th International Symposium on Radiopharmaceutical Chemistry, Jun., 1997.

Hoffman, T.J., Li, N., Higginbotham, C.A., Sieckman, G., Volkert, W.A., "Specific Uptake and Retention of Rh–105 Labeled Bombesin Analogues in GRP–Receptor Expressing Cells", European Society of Nuclear Medicine, Aug., 1997; Eur. J. Nucl. Med., 24(8), 901, 1997 #30.4.

Hoffman, T.J., Quinn, T.P., and Volkert, W.A., "Radiometallated Receptor–Avid Peptide Conjugates for Specific In Vivo Targeting of Cancer", Nuc. Med. & Biol. 28:527–539, 2001.

Hoffman, T.J., Sieckman, G., Volkert, W.A., "Targeting Small Cell Lung Cancer Using Iodinated Peptide Analogs", 11th International Symposium on Radiopharmaceutical Chemistry, Aug., 1995; J. Label. Comp'd Radiopharm., 37:321–323, 1995.

Hoffman, T.J., Sieckman, G.L., Volkert, W.A., "Iodinated Bombesin Analogs: Effect of N–Terminal Chain Iodine Attachment on BBN/GRP Receptor Binding", 43rd Annual Meeting—Society of Nuclear Medicine, May, 1996; J.Nucl. Med., 37(5), p185P, #850, 1996.

Hoffman, T.J., Simpson, S.D., Smith, C.J., Sieckman, G.L., Higginbotham, C., Eshima, D., Volkert, W. and Thornback, J.R. "Accumulation and Retention of 99mTc–RP591 by GRP Receptor Expressing Tumors in SCID Mice", Congress of the European Association of Nuclear Medicine, Barcelona, Spain, Eur. J. Nucl. Med., 26(9), 1157, #PS–416, Sep., 1999.

Hoffman, T.J., Simpson, S.D., Smith, C.J., Sieckman, G.L., Higginbotham, C., Volkert, W. and Thornback, J.R. "Accumulation and Retention of 99mTc–RP527 by GRP Receptor Expressing Tumors SCID Mice", 46th Annual Meeting—Society of Nuclear Medicine, Jun. 9, 1999, Los Angeles, CA, J.Nucl. Med., 40(5), 104P, #419, 1999.

Hoffman, T.J., Smith, C.J., Gali, H., Owen, N.K., Sieckman, G.L., Hayes, D.L., Foster, F., Volkert, W.A., $^{111}$In / $^{90}$Y Radiolabeled Peptides for Targeting Prostate Cancer; A Matched Pain Gastrin Releasing Peptide (GRP) Receptor Localizing Radiopharmaceutical, 48th Annual Meeting–Society of Nuclear Medicine, #1149, Toronto, Ontario, Canada, Jun. 2001. (Accepted).

Hoffman, T.J., Smith, C.J., Gali, H., Owen, N.K., Sieckman, and Volkert, W.A., "In Vitro and In Vivo Evaluation of 111In/90Y Radiolabeled Peptides for Specific Targeting of Tumors Expressing Gastrin Releasing Peptide (GRP) Receptors", 92nd Annual Meeting of the American Association for Cancer Research, New Orleans, LA. Proceedings of the American Association for Cancer Research, vol. 42, 773, #4148, Mar. 2001.

Hoffman, T.J., Smith, C.J., Gali, H., Owen, N.K., Sieckman, Hayes, D.L., and Volkert, W.A., "Development of a Diagnostic Radiopharmaceutical for Visualization of Primary and Metastatic Breast Cancer", 48th Annual Meeting–Society of Nuclear Medicine, Toronto, Ontario, Canada, Jun. 2001,.J. Nuc. Med., 45(5):245P, #1067.

Hoffman, T.J., Smith, C.J., Sieckman, G.L., Owen, N.K., and Volkert, W.A., "Design Synthesis, and Biological Evaluation of Novel Gastrin Releasing Peptide Receptor Targeting Radiopharmaceuticals" American Chemical Society Annual Meeting, Aug. 2000, Washington, D.C.

Hoffman, T.J., Smith, C.J., Simpson, S.D., Sieckman, G.L., Higginbotham, C., Jimenez, H., Eshima, D., Thornback, J.R., and Volkert, W.A. "Targeting Gastrin Releasing Peptide Receptor (GRP–R) Expression in Prostate and Pancreatic Cancer Using Radiolabeled GRP Agonist Peptide Vectors", American Association for Cancer Research Annual Meeting, San Francisco, CA, Proceedings of the American Association for Cancer Research, vol. 41, 529, #3374, Apr., 2000.

Hoffman, T.J., Smith, C.J., Simpson, S.D., Sieckman, G.L., Higginbothan, C., Jimenez, H., Eshima, D., Thornback, J.R., and Volkert, W.A., "Optimizing Pharmacokinetics of Tc–99m–GRP Receptor Targeting Peptides Using Multi–Amino Acid Linking Groups", 47th Annual Meeting—Society of Nuclear Medicine, St. Louis, MO, J.Nucl. Med., 41(5), 228P, #1013, 2000.

Jensen et al., (1993) Rec. Result. Cancer Res., 129:87.

Jurisson, S., Cutler, C., Hu, F., Hoffman, T.J., Volkert, W.A., "DOTA Bombesin Complexes with Sm–153 and NCA PM–149", The International Chemical Congress of Pacific Basin Societies, Pacifichem 2000,, Honolulu, HI, Dec., 2000.

Katti, K.V., Gali, H., Schibli, R., Hoffman, T.J., and Volkert, W.A. "99mTc/Re Coordination Chemistry and Biomolecule Conjugation Strategy of a Novel Water Soluble Phosphine–Based Bifunctional Chelating Agent", In Technetium, Rhenium and Other Metals in Chemistry and Nuclear Medicine (5), Ed. By M. Nicolini and U. Mazzi, Servizi Grafici Editoriali, Padova, pp. 93–100, 1999.

Kothari, K.K., Katti, K.V., Prabhu, K.R., Gali, H., Pillarsetty, N.K., Hoffman, T.J., Owen, N.K., and Volkert, W.A., "Development of a Diamido–Diphosphine (N2P2)–BFCA for Labeling Cancer Seeking Peptides via the 99mTc(I)(CO)3(H2O)3 Intermediate", 47th Annual Meeting—Society of Nuclear Medicine, St. Louis, MO, J.Nucl. Med., 41(5), 244P, #1079, 2000.

Krenning et al., Essentials of Peptide Receptor Scintigraphy With Emphisis on the Somatostatin Analog Octreotide, (Oct. 1994) Semin. In Oncology, vol. 21, No. 5, Suppl. 13, pp. 6–14.

Lamberts, S.W.J., Reubi, J,C., Krenning, E.P., Somatostatin and the Concept of Peptide Receptor Scintigraphy in Oncologu, (Oct. 1994) Semin. In Oncol., vol. 21, No. 5, Suppl. 13, pp. 1–5.

Leban et al. Potent Gastrin–Releasing Peptide (GRP) Antagonists Derived from GRP (19–27) with a C–Terminal $_D$Proψ [CH$_2$NH] Phe–NH$_2$ and N–Terminal Aromatic Residues, (1994) J. Med. Chem., 37:439–445.

Li, W.P., Ma, D.S., Higginbotham, C. Hoffman, T.J., Ketring, A.R., Cutler, C.S., Jurisson, S.S., Development of an In Vitro Model for Assessing the In Vivo Stability of Lanthanide Chelates, Nuc. Med. & Biol. 28:145–154, 2001.

Li et al., Comparisons of $^{105}$Rh(III) Chloride Complexation with [14]aneNS$_3$, [14]aneN$_2$S$_2$ and [14]and N$_4$ Macrocycles in Aqueous Solution, (1996) Radiochim Acta, 75:83–95.

Lister–James et al. Pharmacokinetic considerations in the development of peptide–based imaging agents, (1997) Quart. J. Nucl. Med., 41:111–118.

Mattes, (1995) Pharmacokinetics of antibodies and their radiolabels. In: Cancer Therapy with Radiolabeled Antibodies (ed) D.M. Goldenberg, CRC Press, Boca Raton, FL, 89–99.

Moody et al., BW2258U89: A GRP Receptor Antagonist Which Inhibits Small Cell Lung Cancer Growth, (1995) Life Sciences, 56(7), 521–529, 1995.

Moody et al., BW1023U90: A New GRP Receptor Antagonist for Small–Cell Lung Cancer Cells, Peptides, 17(8), 1337–1343, 1996.

Ning, Li, Hoffman, T.J., Sieckman, G.L., Ochrymowycz, L.A., Higginbotham, C., Struttman, M., Volkert, W.A., and Ketring, A.R., In–vitro and In–vivo Characterization of a RH–105–tetrathiamacrocycle Conjugate of a Bombesin Analogue, 43rd Annual Meeting—Society of Nuclear Medicine, May, 1996; J.Nucl. Med., 37(5), p61P, #235. 1996.

Parker, D., Tumour Targeting with Radiolabelled Macrocycle–Antibody Conjugates, (1990) Chem. Soc. Rev., 19:271–291.

Qin et al., Bombesin antagonist inhibit in vitro and in vivo growth of human gastric cancer and binding of bombesin to its receptors, (1994) J. Canc. Res. Clin. Oncol., 120:519–528.

Qin, Y. et al., Inhibitory Effect of Bombesin Receptor Antagonist RC–3095 on the Growth of Human Pancreatic Cancer Cells in Vivo and in Vitro, (Feb. 15, 1994) Cancer Research 54:1035–1041.

Reile, H. et al., Characterization of High–Affinity Receptors for Bombesin/Gastrin Releasing Peptide on the Human Prostate Cancer Cell Lines PC–3 and DU–145: Internalization of Receptor Bound $^{125}$I–(Tyr$^4$) Bombesin by Tumor Cells, (1994) The Prostate 25:29–38.

Schibli, R., Karra, S., Katti, K.V., Gali, H., Higginbotham, C., Sieckman, G., Hoffman, T.J., Volkert, W.A., A Tc–99m–Dithia–Di(Bis–Hydroxy–methylene) Phosphine Conjugate of Bombesin: In Vitro and In Vivo Studies, 45th Annual Meeting—Society of Nuclear Medicine, May 1998; J.Nucl. Med., 39(5), 225P, #997.

Schibli, R., Karra, S.R., Gali, H., Katti, K.V., Hoffman, T.J., and Volkert, W.A., Conjugation of Small Biomolecules and Peptides with Water–Soluble Dithio–Bis–Hydroxymethylphosphine Ligands, Center Radiological Research, University Missouri, Columbia, MO, USA. Book of Abstracts, 215$^{th}$ ACS National Meeting, Dallas, Mar. 19–Apr. 2, 1998, NUCL–062.

Schubiger et al., Vehicles, Chelators, and Radionuclides: Choosing the "Building Blocks" of an Effective Therapeutic Radioimmunoconjugate, (Mar./Apr. 1996) Bioconj. Chem. 7(2):165–179.

Seifert et al. No Carrier Added Preparations of '3 + 1' Mixed–ligand $^{99m}$Tc Complexes, (1998) Appl. Radiat. Isot., 49(1–2):5–11.

Smith et al., In Vitro and In Vivo Characterization of Novel Water–Soluble Dithio–Biosphine $^{99m}$TcComplexes, (1997) Nucl. Med. & Biol., 24:685–691.

Smith, C.J., Hoffman, T.J., Gali, H., Hayes, D.L., Owen, N.K., Sieckman, G.L., and Volkert, W.A., "Radiochemical Investigations of $^{177}$Lu–DOTA–8–Aoc–BBN(7–14)NH$_2$: A New Gastrin Releasing Peptide Receptor (GRPr) Targeting Radiopharmaceutical", J. Labeled Compounds and Radiopharmaceutical, J. Labelled Cpd. Radiopharm., 44 (51):5706–5708, 2001.

Smythe, E. et al., The Mechanism of receptor–mediated endocytosis, (1991) Eur. J. Biochem. 202:689–699.

Troutner, D.E., Chemical and Physical Properties of Radionuclides, (1987) Nucl. Med. Biol., 14(3):171–176.

Vallabhajosula et al., Preclinical Evaluation of Technetium–99m–Labeled Somatostatin Receptor–Binding Peptides, (1996) J. Nucl. Med., 37(6):1016–1022.

Volkert, W.A., and Hoffman, T.J., Design and Development of Receptor–avid Peptide Conjugates for In Vivo Targeting of Cancer, Part of the SPIE Conferene of Molecular Imaging: Reporters–Dyes, Markers and Instrumentation, SPIE vol. 3600:86–98, Jan. 1999.

Volkert, W.A., Gali, H–P, Hoffman, T.J., Owen, N.K., Sieckman, G.L., and Smith, C.J., In–111 / 90Y Labeled GRP Analogs: A Structure–Activity Relationship, The International Chemical Congress of Pacific Basin Societies, Pacifichem 2000,, Honolulu, HI, Dec. 2000.

Wong, E. et al., Rhenium(V) and Technetium(V) Oxo Complexes of an N2N'S Peptide Chelator: Evidence of Interconversion between the Syn and Anti Conformations, (1997) Inorg. Chem. 36:5799–5808.

Zhu, W–Y. et al., Binding, internalization, and processing of bombesin by rat pancreatic acini, (1991) The Am. Physiol. Society, G57–64.

Heppeler et al., Receptor Targeting for Tumor Localization and Therapy with Radiopeptides. Current Medicinal Chemistry 2000, 7:971–994.

* cited by examiner

A.
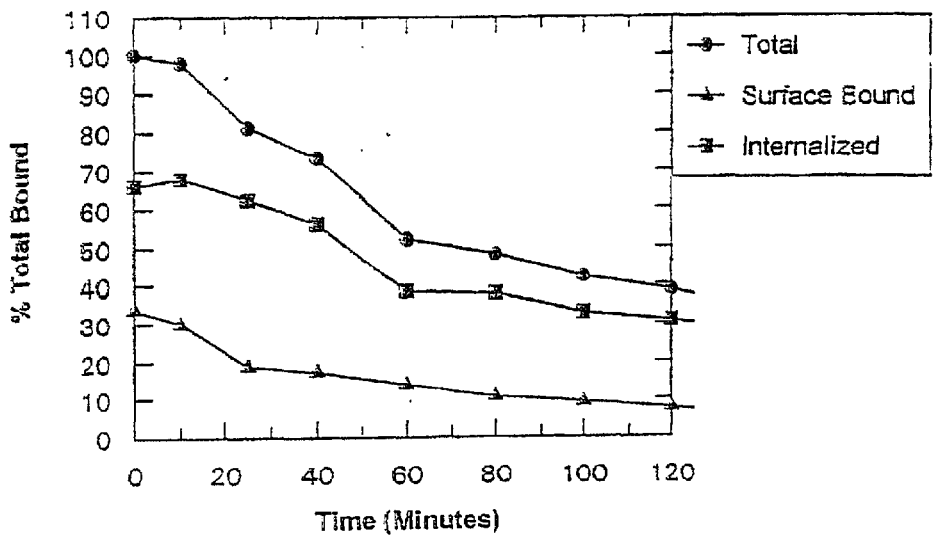
B.
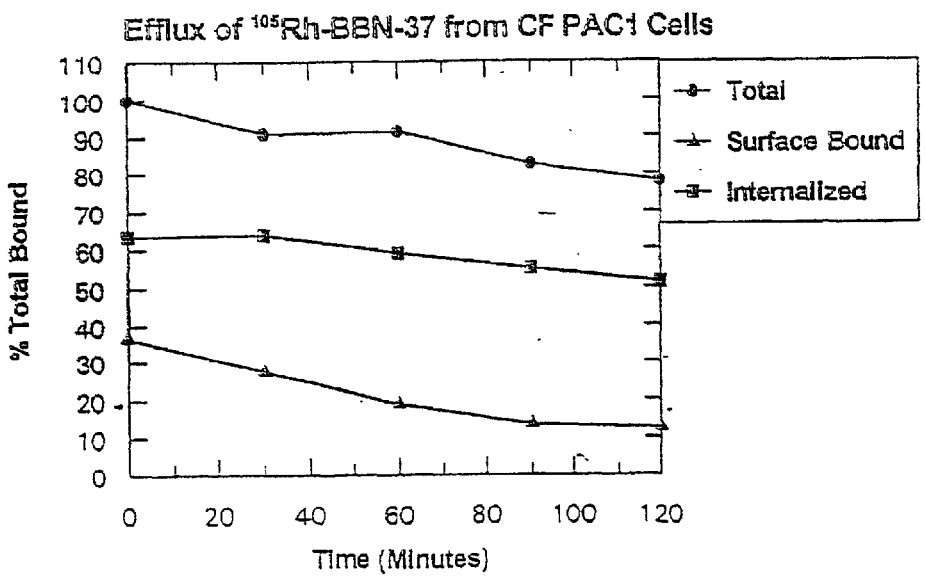
Figure 17

US 7,060,247 B2

GASTRIN RECEPTOR-AVID PEPTIDE CONJUGATES

CROSS-REFERENCE

This patent application is a continuation-in-part of U.S. patent application Ser. No. 09/537,423, filed Mar. 29, 2000, now abandoned which is a divisional of U.S. patent application Serial No. 09/064,499, filed Apr. 22, 1998 now U.S. Pat. No. 6,200,546 which is a conversion of U.S. Provisional Application Serial No. 601044,049, filed on Apr. 22, 1997, all of which are incorporated herein by reference.

GRANT REFERENCE

The research carried out in connection with this invention was supported in part by a grant from the Department of Energy (DOE), grant number DE-FG02-89ER60875, a grant from the U.S. Department of Veterans Affairs Medical Research Division and the Department of Radiology MU-C2-02691. The Government has certain rights in the invention.

TECHNICAL FIELD

This invention relates to radionuclide-labeled compounds useful as radiopharmaceuticals. More particularly, the present invention relates to conjugates of bombesin (BBN) analogues and a metal complexing group which, when complexed to a radionuclide, are useful therapeutic and imaging agents for cancer cells that express gastrin releasing peptide (GRP) receptors.

BACKGROUND OF THE INVENTION

Detection and treatment of cancers using radiopharmaceuticals that selectively target cancers in human patients has been employed for several decades. Unfortunately, only a limited number of site-directed radiopharmaceuticals that exhibit highly specific in vivo localization in or near cancer cells are currently in routine use, as being approved by the United States Food and Drug Administration (FDA). There is a great deal of interest in developing new radioactive drugs due to the emergence of more sophisticated biomolecular carriers that have high affinity and high specificity for in vivo targeting of tumors. Several types of agents are being developed and have been investigated including monoclonal antibodies (MAbs), antibody fragments ($F_{AB}$'S and $(F_{AB})_2$s), receptor-avid peptides [Bushbaum, 1995; Fischman et al., 1993; Schubiger et al. 1996].

The potential utility of using radiolabeled receptor-avid peptides for producing radiopharmaceuticals is best exemplified by $^{111}$In-DTPA-conjugated octreotide (an FDA approved diagnostic imaging agent, Octreoscan®, marketed in the United States. by Mallinckrodt Medical, Inc.) [Lowbertz et al. 1994]. This radiopharmaceutical is an $^{111}$In-DTPA conjugate of Octreotide, a small peptide analogue of the human hormone somatostatin. This drug specifically binds to somatostatin receptors that are over-expressed on neuroendocrine cancers (e.g., carcinoid Ca, neuroblastoma, etc.) as well as others [Krenning et al., 1994]. Since indium-111 ($^{111}$In) is not the ideal radionuclide for scintigraphic imaging, other somatostatin analogues and other receptor-avid biomolecules that are labeled with $^{99m}$Tc (the optimal radionuclide for diagnostic imaging) are being studied and developed [Eckelman, 1995; Vallabhajosula et al., 1996].

Bombesin (BBN) is a 14 amino acid peptide that is an analogue of human gastrin releasing peptide (GRP) that binds to GRP receptors with high specificity and has an affinity similar to GRP [Davis et al., 1992]. GRP receptors have been shown to be over-expressed or uniquely expressed on several types of cancer cells. Binding of GRP receptor agonists (also autocrine factors) increases the rate of cell division of these cancer cells. For this reason, a great deal of work has been, and is being pursued to develop BBN Qr GRP analogues that are antagonists [Davis et al., 1992; Hoffken, 1994; Moody et al., 1996; Coy et al., 1988; Cai et al., 1994]. These antagonists are designed to competitively inhibit endogenous GRP binding to GRP receptors and reduce the rate of cancer cell proliferation [Hoffken, 1994]. Treatment of cancers using these antagonists with these non-radioactive peptides requires chronic injection regimens (e.g., daily, using large quantities of the drug).

In designing an effective receptor-avid radiopharmaceutical for use as a diagnostic or therapeutic agent for cancer, it is important that the drug have appropriate in vivo targeting and pharmacokinetic properties [Fritzberg et al., 1992; Eckelman et al., 1993]. For example, it is essential that the radiolabeled receptor-avid peptide have high specific uptake by the cancer cells (e.g., via GRP receptors). In addition, it is necessary that once the radionuclide localizes at a tumor site, it must remain there for an extended time to deliver a highly localized radiation dose to the tumor. In order to achieve sufficiently high specific uptake of radiolabeled BBN analogues in tumors, the binding affinity of promising derivatives must be high (i.e., $Kd_d \cong 1-5$ nmolar or less) with prolonged retention of radioactivity [Eckelman et al., 1995; Eckelman, et al., 1993]. Work with $^{125}$I-BBN derivatives has shown, however, that for cancer cells that bind the $^{125}$I-BBN derivatives (whether they be agonists or antagonists), the radioactivity is either washed off or expelled from the cells (in vitro) at a rapid rate [Hoffman et al., 1997]. Thus, these types of derivatives have a low probability of remaining "trapped" at the tumor site (in vivo) sufficiently long to be effective therapeutic or diagnostic agents.

Developing radiolabeled peptides that are cleared efficiently from normal tissues is also an important and especially critical factor for therapeutic agents. When labeling biomolecules (e.g., MAb, FAB'S or peptides) with metallic radionuclides (via a chelate conjugation), a large percentage of the metallic radionuclide (in some chemical form) usually becomes "trapped" in either the kidney or liver parenchyma (i.e., is not excreted into the urine or bile) [Duncan et al., 1997; Mattes, 1995]. For the smaller radiolabeled biomolecules (i.e., peptides or FAB's), the major route of clearance of activity is through the kidneys which in turn retain high levels of the radioactive metal (i.e., normally>10–15% of the injected dose) [Duncan et al., 1997]. This presents a major problem that must be overcome in the development of therapeutic agents that incorporate metallic radionuclides, otherwise the radiation dose to the kidneys would be excessive. For example, $^{111}$In-octreotide, the FDA approved diagnostic agent, exhibits high uptake and retention in kidneys of patients [Eckelman et al., 1995]. Even though the radiation dose to the kidneys is higher than desirable, it is tolerable in that it is a diagnostic radiopharmaceutical (it does not emit alpha- or beta-particles), and the renal dose does not produce observable radiation induced damage to the organ.

It has been found that conjugating non-metallated metal chelates to BBN derivatives can form GRP agonists which exhibit binding affinities to GRP receptors that are either similar to or approximately an order of magnitude lower than the parent BBN derivative. [Li et al., 1996a] Our recent results show that it is now possible to add radiometal chelates to BBN analogues, to form conjugates which are agonists, and retain GRP receptor binding affinities that are sufficiently high (i.e., approx. 1–5 nmolar Kd's) for further development as potential radiophanmaceuticals. These agonist conjugates are transported intracelluladly after binding to cell surface GRP receptors and retained inside of the cells for extended time periods. In addition, in vivo studies in normal mice have shown that retention of the radioactive metal in the kidneys was low (i.e., <5%) with the majority of the radioactivity excreted into the urine.

According to one aspect of the present invention, there is provided a BBN conjugate consisting of essentially a radiometal chelate covalently appended to the receptor binding region of BBN [e.g., BBN(8–14) or BBN(7–14)] to form radiolabeled BBN analogues that have high specific binding affinities with GRP receptors. These analogues are retained for long times inside of GRP expressing cancer cells. Furthermore, their clearance from the bloodstream, into the urine with minimal kidney retention, is efficient. Preferably, the radiometals are selected from $^{99m}Tc$, $^{186/188}Re$, $^{105}Rh$ $^{153}Sm$, $^{166}Ho$, $^{90}Y$, $^{199}Au$, $^{177}Lu$, $^{149}Pr$, or $^{111}In$, all of which hold the potential for diagnostic (i.e., $^{99m}Tc$ and $^{111}In$) or therapeutic (i.e., $^{186/188}Re$, $^{105}Rh$, $^{153}Sm$, $^{166}Ho$, $^{90}Y$, $^{199}Au$, $^{177}Lu$, $^{149}Pm$, $^{166}Dy$, $^{175}Yb$, $^{117m}Sm$ and $^{111}In$) utility in cancer patients [Schubiger et al, 1996; Eckelman, 1995; Troutner, 1978].

SUMMARY OF THE INVENTION

In accordance with the present invention, there is provided a compound for use as a therapeutic or diagnostic radiopharmaceutical which includes a group which is capable of complexing a metal attached to a moiety capable of binding to a gastrin releasing peptide receptor.

Additionally, in accordance with the present invention, a method for treating a subject having a neoplastic disease which includes the step of administering to the subject an effective amount of a radiopharmaceutical having a metal chelated with a chelating group attached to a moiety capable of binding to a gastrin releasing peptide receptor on a cancer cell, subsequently intracellularly transported and residualized inside the cell, is disclosed.

Additionally, in accordance with the present invention, a method of forming a therapeutic or diagnostic compound including the step of reacting a metal synthon with a chelating group covalently linked with a moiety capable of binding a gastrin releasing peptide receptor is disclosed.

BRIEF DESCRIPTION OF THE DRAWINGS

Other advantages of the present invention will be readily appreciated as the same becomes better understood by reference to the following detailed description when considered in connection with the accompanying drawings wherein:

FIG. 17 are graphs illustrating Pancreatic CA cell binding wherein (A) illustrates the efflux $^{125}$-Tyr$^4$-BBN from CF PAC1 cells and (B) illustrates the efflux of $^{105}Rh$-BBN-37 from CF PAC1 cells;

DETAILED DESCRIPTION OF THE INVENTION

Figure 1:
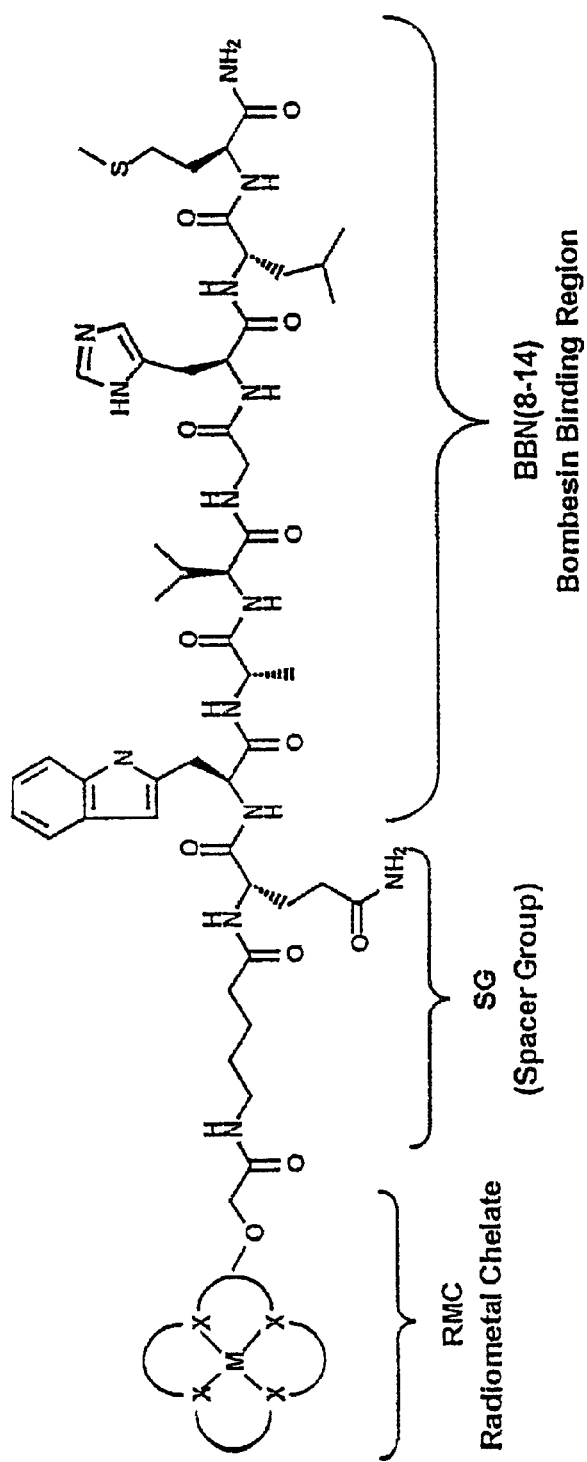
FIG. 1 illustrates a radiometal conjugate according to the present invention.

According to the present invention, compounds for use as diagnostic and/or therapeutic radiopharmaceuticals include a group capable of complexing a metal attached to a moiety capable of binding to a gastrin releasing peptide (GRP) receptor as shown in FIG. 1. These compounds can be prepared with either a diagnostic radiometal or a therapeutic radiometal thus affording utilities as either a diagnostic agent to identify cancerous tissues within the body using scintigraphic imaging techniques, or a therapeutic agent forjhe treatment and control of cancerous tissues. The moiety capable of specific binding to the GRP receptor is a GRP agonist. A GRP agonist activates or produces response by the GRP receptor upon interaction with the GRP receptor and is subsequently internalized inside of the cell by endocytosis. In contrast, a GRP antagonist counteracts the effect of an agonist and is not internalized inside of the cell.

More specifically, the GRP agonist for the purpose of this invention is a compound such as selected amino acid sequences or peptidomimetics which are internalized or residualized following binding with high affinity and selectivity to GRP receptors and that can be covalently linked to the metal complexing group. Many examples of specific modifications of the BBN(7–14) or BBN(8–14) that can be made to produce sequences with high antagonistic and agonistic binding affinity for GRP repectors have been reported by numerous investigations [Davis et al., 1992; Hoffken, 1994; Moody et al., 1996; Coy et al., 1988; Cai et al., 1994; Moody et al., 1995; Leban et al., 1994; Cai et al., 1992].

In a preferred embodiment of the present invention, the metal complexing group or moiety is a chelating agent or chelator which complexes to metals such as $^{105}$Rh-, $^{186/188}$Re, $^{99m}$—Tc, $^{153}$Sm, $^{166}$Ho, $^{90}$Y, $^{111}$In, $^{177}$Lu, $^{149}$Sm or $^{199}$Au. The chelating agent or chelator is attached or bound to the GRP agonist "binding region" through a spacer to produce a conjugate that retains its capability for high affinity and specific binding to GRP receptors.

In a more preferred embodiment of the present invention, the GRP agonist is a bombesin (BBN) analogue and/or a derivative thereof. The BBN derivative or analog thereof preferably contains either the same primary structure of the BBN binding region [i.e., BBN(8–14) or BBN[7–14)] or similar primary structures, with specific amino acid substitutions, that will specifically bind to GRP receptors with better or similar binding affinities as BBN alone (i.e., Kd≅1–5 nmolar) Compounds containing this BBN binding region (or binding moiety), when covalently linked to other groups (e.g., a radiometal chelate), are also referred to as BBN conjugates.

In general, the compounds of the present invention have a structure of the general formula:

X-Y-B wherein X is a group capable of complexing a metal, such as a radiometal; Y is a covalent bond on a spacer group; and B is a bombesin agonist binding moiety.

The metal bound to the metal complexing group can be any suitable metal chosen for a specific therapeutic or diagnostic use including transition metals, lanihanides, auger electron emitting isotopes, a, p or y emitting isotopes. Preferably, the metal is a radiometal such as $^{105}$Rh—, $^{99m}$Tc—, 186/188Re, $^{153}$ Sm—, $^{168}$Ho—, $^{111}$In, $^{90}$Y—, $^{177}$Lu, $^{149}$Pm, $^{153}$Sm, and $^{199}$Au— whose chelates can be covalently linked (i.e., conjugated) to the specific BBN binding region via the N-terminal end of the primary binding sequence (e.g., BBN-8 or Trp$^8$) as shown in FIG. 1.

In a preferred embodiment, the radiometal complexes are positioned by being spaced apart from or remotely from the amino acid Trp$^8$ by the spacer groups. The spacer groups can include a peptide (i.e., ≧1 amino acid in length), a hydrocarbon spacer of, $C_1$–$C_{10}$ or a combination of thereof. Preferably, the hydrocarbon spacer is a $C_3$-Ca group. The resulting radio-labeled BBN conjugates retain high binding affinity and specificity for GRP receptors and are subsequently internalized inside of the cell.

The BBN conjugates can further incorporate a spacer group or component to couple the binding moiety to the metal chelator (or metal binding backbone) while not adversely affecting either the targeting function of the BBN-binding moiety or the metal complexing function of the metal chelating agent.

The term "spacer group" or "linker" refers to a chemical group that serves to couple the BBN binding moiety to the metal chelator while not adversely affecting either the targeting function of the BBN binding moiety or the metal complexing function of the metal chelator. Suitable spacer groups include peptides (i.e., amino acids linked together) alone, a non-peptide group (e.g., hydrocarbon chain) or a combination of an amino acid sequence and a non-peptide spacer. The type of spacer group used in most of the experimental studies described below in the Examples section were composed of a combination of L-glutamine and hydrocarbon spacers. A pure peptide spacer could consist of a series of amino acids (e.g., diglycine, triglycine, gly-gly-glu, gly-ser-gly, etc.), in which the total number of atoms between the N-terminal residue of the BBN binding moiety and the metal chelator in the polymeric chain is ≦12 atoms.

The spacer can also include a hydrocarbon chain [i.e., —(CH$_2$)$_n$—R$_2$] wherein n is 0–10, preferably n=3 to 9, R$_1$ is a group (e.g., H$_2$N—, HS—, —COOH) that can be used as a site for covalently linking the ligand backbone or the preformed metal chelator or metal complexing backbone; and R$_2$ is a group that is used for covalent coupling to the N-terminal NH$_2$-group of the BBN binding moiety (e.g., R$_2$ is an activated COOH group). Several chemical methods for conjugating ligands (i.e., chelators) or preferred metal chelates to biomolecules have been well described in the literature [Wilbur, 1992; Parker, 1990; Hermanson, 1996; Frizberg et al., 19951. One or more of these methods could be used to link either the uncomplexed ligand (chelator) or the radiometal chelate to the spacergroup or to link the spacer group to the BBN(8–14) derivatives. These methods include the formation of acid anhydrides, aldehydes, arylisothiocyanates, activated esters, or N-hydroxysuccinimides [Wilbur, 1992; Parker, 1990; Hermanson, 1996; Frizberg et al., 1995].

Figure 2:
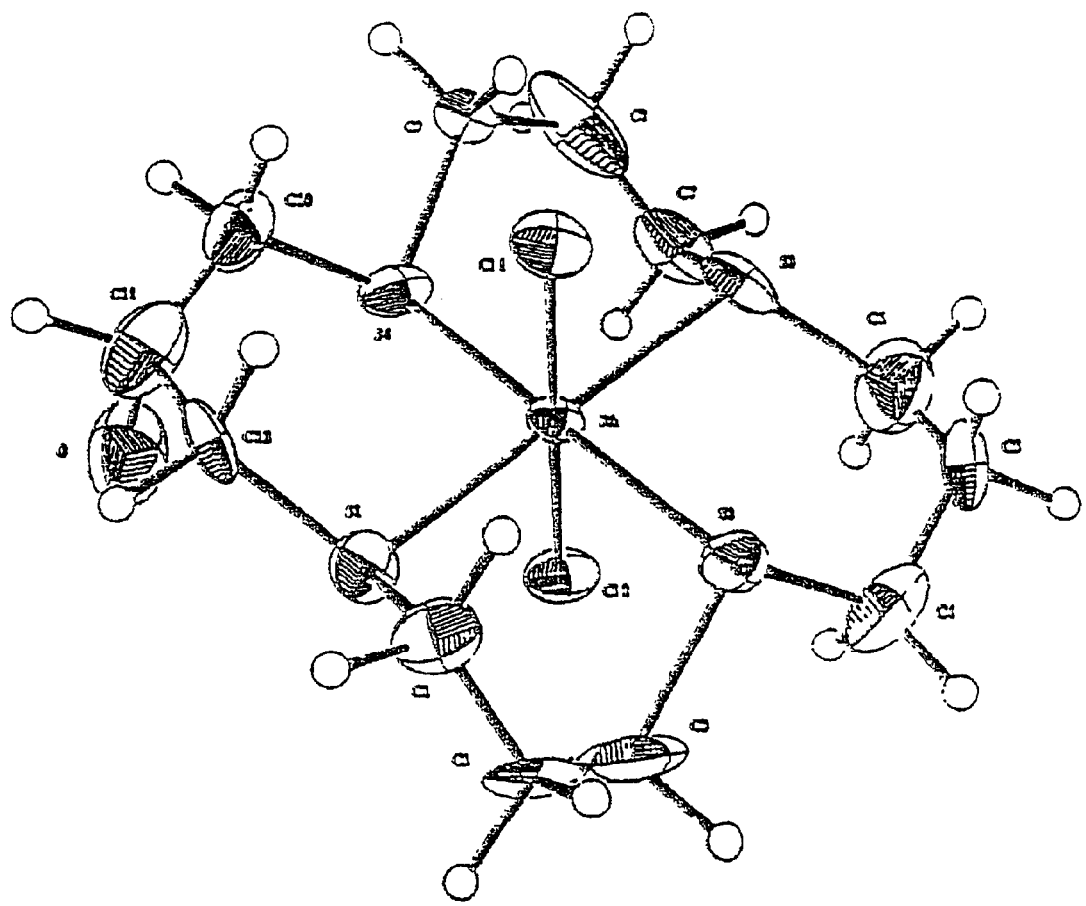
FIG. 2 is an ORTEP drawing of the {Rh[16]aneS$_4$-olCl$_2$}$^+$, illustrating the crystal structure a Rhodium macrocycle.

The term "metal complexing chelator" refers to a molecule that forms a complex with a metal atom that is stable under physiological conditions. That is, the metal will remain complexed to the chelator backbone in vivo. More particularly, a metal complexing chelator is a molecule that complexes to a radionuclide metal to form a metal complex that is stable under physiological conditions and which also has at least one reactive functional group for conjugation with the BBN agonist binding moiety. Metal complexing chelators can include monodentate and polydentate chelators [Parker, 1990; Frizberg et al., 1995; Lister-James et al., 1997; Li et al., 1996b; Albert et al., 1991; Pollak et al., 1996; de Jong et al., 1997; Smith et al., 1997] and include the DOTA chelators discussed in more detail below. Metal complexing chelators include tetradentate metal chelators which can be macrocyclic and have a combination of four nitrogen and/or sulfur metal-coordinating atoms [Parker et al., 1990; Li et al., 1996b] and are designated as N$_4$, S$_4$, N$_3$S, N$_2$S$_2$, NS$_3$, etc. as shown in FIG. 2. A number of suitable multidentate chelators that have been used to conjugate proteins and receptor-avid molecules have been reported [Frizberg et al., 1995; Lister-James et al., 1997; Li et al., 1996b; Albert et al., 1991; Pollak et al., 1996; de Jong et al., 1997] and include the DOTA chelators discussed in more detail below These multidentate chelators can also incorporate other metal-coordinating atoms such as oxygen and phosphorous in various combinations. The metal binding complexing moiety can also include "3+1" chelators [Seifert etal., 1998].

For diagnostic purposes, metal complexing chelators preferably include chelator backbones for complexing the radionuclide metals mTc andl In. For therapeutic purposes, metal complexing chelators preferably include chelator backbones that complex the beta particle emitting radionuclide metals including $^{105}$Rh, $^{186/188}$Re, $^{153}$Sm, $^{90}$Y, $^{166}$Ho, $^{199}$Au, $^{177}$Lu, $^{111}$In, $^{166}$Dy, $^{175}$Yb and $^{149}$Pm [Schubiger et al., 1996; Hoffken, 1994].

As was briefly described above, the term "bombesin agonist" or "BBN agonist" refers to compounds that bind with high specificity and affinity to GRP receptors, and upon binding to the GRP receptor, are intracellularly internalized. Suitable compounds include peptides, peptidomimetics and analogues and derivatives thereof. In particular, previous work has demonstrated that the region on the BBN peptide structure required for binding to GRP receptors spans from residue 8 through 14 [Davis et al., 1992; Hoffken, 1994; Moody et al., 1996; Coy, 1988; Cai et al., 1994]. The presence of methionine (Met) at position BBN-14 will generally confer agonistic properties while the absence of this residue at BBN-14 generally confers antagonistic properties [Hoffken, 1994].

It is well documented in the art that there are a few and selective,number of specific amino acid substitutions in the BBN (8–14) binding region (e.g., D-Ala$^{11}$ for L-Gly$^{11}$ or D-Trp$^8$ for L-Trp$^8$), which can be made without decreasing binding affinity (Leban et al., 1994; Qin et al., 1994; Jensen et al., 1993]. In addition, attachment of some amino acid chains or other groups to the N-terminal amine group at position BBN-8 (i.e., the Trp$^8$ residue) can dramatically decrease the binding affinity of BBN analogues to GRP receptors (Davis et al., 1992; Hoffken, 1994; Moody et al., 1996; Coy, et al., 1988; Cai et al., 1994]. In a few cases, it is possible to append additional amino acids or chemical moieties without decreasing binding affinity. The effects of conjugating various side chains to BBN-8 on binding affinity, therefore, is not predicable.

The BBN conjugates of the present invention can be prepared by various methods depending upon the selected chelator. The peptide portion of the conjugate can be most conveniently prepared by techniques generally established and known in the art of peptide synthesis, such as the solid-phase peptide synthesis (SPPS) approach. Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support with its amino group protected with an N-protecting agent such as a t-butyloxycarbonyl group (tBoc) or a fluorenylmethoxycarbonyl (FMOC) group. The amino protecting group is removed with suitable deprotecting agents such as TFA in the case of tBOC or piperidine for FMOC and the next amino acid residue (in N-protected form) is added with a coupling agent such as dicyclocarbodiimide (DCC). Upon formation of a peptide bond, the reagents are washed from the support. After addition of the final residue, the peptide is cleaved from the support with a suitable reagent such as trifluoroacetic acid (TFA) or hydrogen fluoride (HF).

The spacer groups and chelator components are then coupled to form a conjugate by reacting the free amino group of the Trp$^8$ residue of the BBN binding moiety with an appropriate functional group of the chelator, metal chelator or spacer group, such as a carboxyl group or activated ester.

The BBN conjugate can also incorporate a metal complexing chelator backbone that is peptidic and compatible with solid-phase peptide synthesis. In this case, the chelator backbone can be added to the BBN binding moiety in the same manner as described above or, more conveniently, the metal complexing chelator backbone coupled to the BBN binding moiety can be synthesized in toto starting from the C-terminal residue of the peptide and ending with the N-terminal residue of the metal complexing chelator structure.

Figure 3:
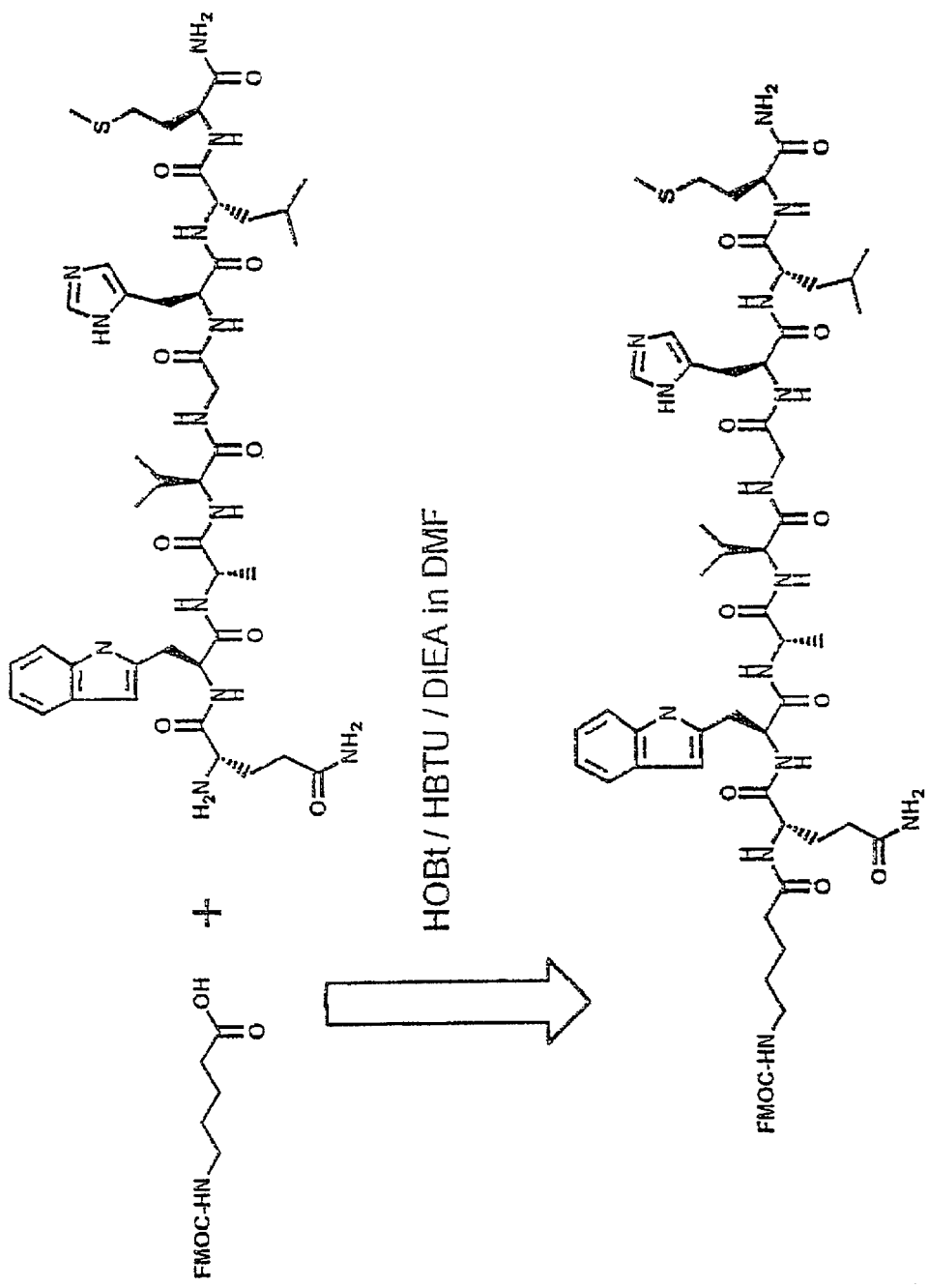
FIG. 3 illustrates a coupling reaction wherein a spacer group is coupled to a bombesin agonist binding moiety.
Figure 4:
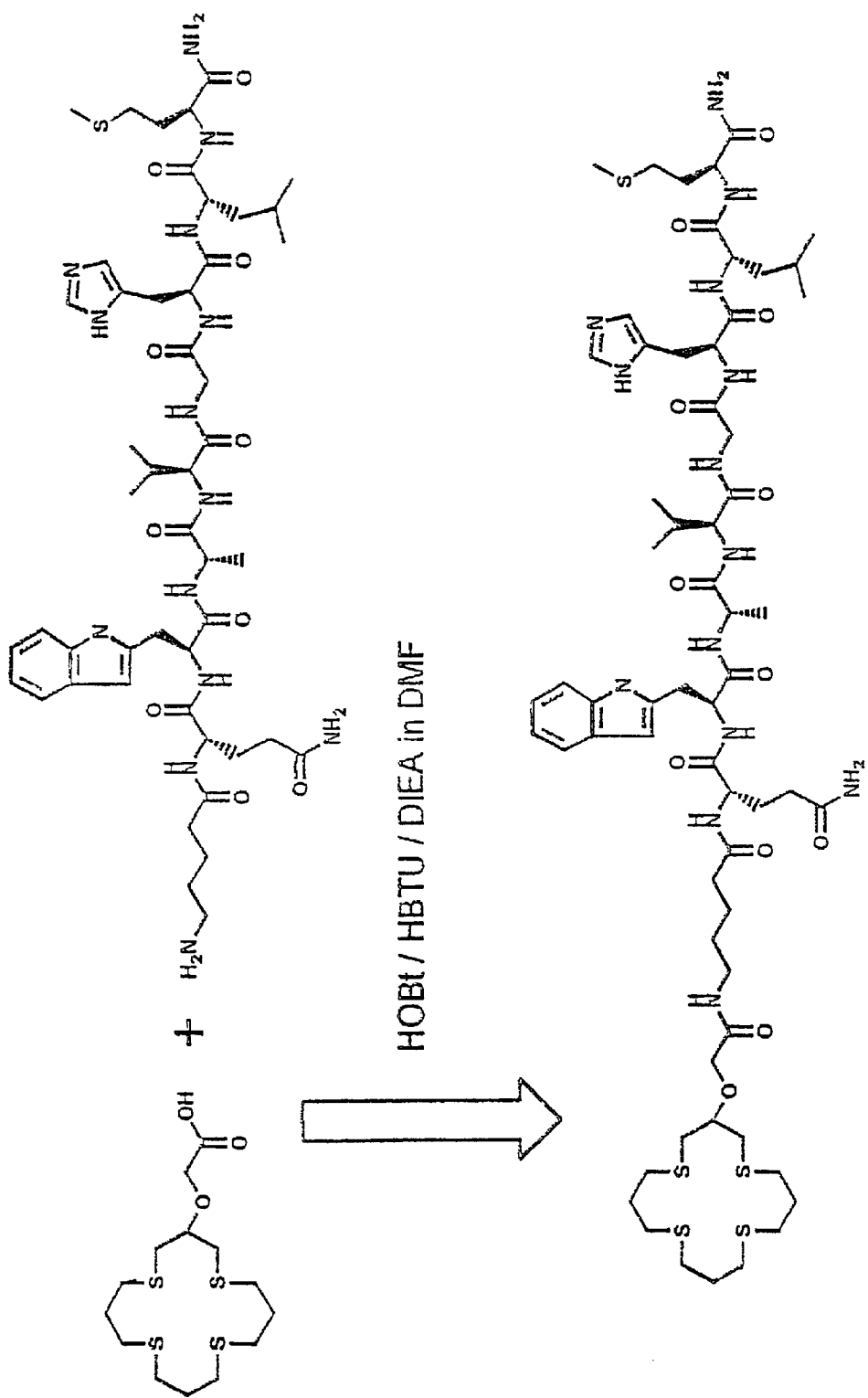
FIG. 4 illustrates a coupling reaction for coupling a metal chelate to a peptide.

The chelator backbones used in accordance with the present invention are commercially available or they could be made by methods similar to those outlined in the literature [Fnzberg et al., 1995; Lister-James et al., 1997; Li et al., 1996b; Albert et al., 1991; Pollak et al., 1996; de Jong et al., 1997; Smith et al., 1997; Seifert et al., 1998]. Attachment of the spacer groups to functionalizable atoms appended to the ligand backbone can be performed by standard methods known to those skilled in the art. For example, the HOBt/HBTU activated —COOH group on 5-aminovaleric acid (5-AVA) was reacted with the N-terminal amine on Gin$^7$ to produce an amide linkage as shown in FIG. 3. Similarly, the —COOH group attached to the characterized [16]aneS$_4$ ligand was conjugated to the amine group on the hydrocarbon spacer (shown below) by reaction of the HOBtlHBTU activated carboxyl group appended to the [16]aneS$_4$ macrocycle with the terminal amine group on 5-AVA to form BBN-37 as shown in FIG. 4. Other standard conjugation reactors that produce covalent linkages with amine groups can also be used [Wilbur, 1992; Parker, 1990].

The chelating framework, conjugated via Trp$^8$, that complexes the radiometals should form a 1:1 chelator to metal ratio. Since $^{99m}$Tc has a short half-life (6 hour) and is a diagnostic radionuclide, the method of forming the $^{99}$mTc-BBN analogues should permit complexation (either directly or by transmetallation) of $^{99m}$Tc to the conjugated chelating framework in a one-step, high yield reaction (exemplified below in the Experimental Section).

In contrast, the longer half lives of the therapeutic radionuclides (e.g., $^{105}$Rh, $^{186/188}$Re, $^{153}$SM, $^{166}$HO, $^{90}$Y, $^{177}$Lu, $^{149}$Pm, $^{199}$Au, $^{111}$In, $^{177}$Lu) permit formation of the corresponding radiolabeled BBN analogues by either a one step high yield complexation step or by performing a $^{105}$Rh—, $^{186/188}$Re—, $^{153}$Sm, $^{166}$Ho, $^{90}$Y, $^{177}$Lu, $^{111}$In or $^{149}$Au chelate synthon followed by conjugation of the preformed complex to the N-terminal end of the BBN binding moiety. In all cases, the resulting specific activity of the final radiolabeled BBN derivative must be high (i.e.,>1Ci/mole). Re— and Tc—-conjugates Re and Tc are both in row VIIB of the Periodic Table and they are chemical congeners. Thus, for the most part, the complexation chemistry of these two metals with ligand frameworks that exhibit high in vitro and in vivo stabilities are the same [Eckelman, 1995]. Many $^{99m}$Tc or $^{186/188}$Re complexes, which are employed to form stable radiometal complexes with peptides and proteins, chelate these metals in their +5 oxidation state [Lister-James et al., 1997]. This oxidation state makes it possible to selectively place $^{99m}$Tc- or $^{186/188}$Re into ligand frameworks already conjugated to the biomolecule, constructed from a variety of $^{99m}$Tc(V) and/or $^{186/188}$Re(V) weak chelates (e.g., $^{99}$Tc—glucoheptonate, citrate, gluconate, etc.) [Eckelman, 1995; Lister-James et al., 1997; Pollak et al., 1996]. Tetradentate ligand frameworks have been shown to form well-defined, single chemical species in high specific activities when at least one thiol group or at least one hydroxymethylene phosphine group is present on the ligand backbone [Smith et al., 1997].

Ligands which form stable Tc(V) or Re(V) tetradentate complexes containing, but not limited to, amino N-atoms, amido-N-atoms, carboxy-O-atoms and thioether-S-atoms, are donor atoms that can also be present [Eckelman, 1995; Fritzberg et al., 1992; Parker, 1990; Frizberg et al., 1995; Pollak et al., 1996; Seifert et al., 1998]. Depending upon the mix of donor atoms (groups), the overall complex charge normally ranges from −1 to +1.

Incorporation of the metal within the conjugate can be achieved by various methods commonly known in the art of coordination chemistry. When the metal is technetium-99m, the following general procedure can be used to form a technetium complex. A peptide-chelator conjugate solution is formed by initially dissolving the conjugate in water or in an aqueous alcohol such as ethanol. The solution is then degassed to remove oxygen. When an -SH group is present in the peptide, the thiol protecting group(s) are removed with a suitable reagent, for example with sodium hydroxide, and are then neutralized with an organic acid such as acetic acid (pH 6.0–6.5). In the labeling step, sodium pertechnetate obtained from a molybdenum generator is added to a solution of the conjugate with a sufficient amount of a reducing agent, such as stannous chloride, to reduce technetium and is either allowed to stand at room temperature or is heated. The labeled conjugate can be separated from the contaminants $^{99m}$TcO$_4^-$ and colloidal $^{99m}$TCO$_2$ chromatographically, for example with a C-18 Sep Pak cartridge [Millipore Corporation, Waters Chromatography Division, 34 Maple Street, Milford, Mass. 01757].

In an alternative method, the labeling can be accomplished by a transchelation reaction. The technetium source is a solution of technetium complexed with labile ligands facilitating ligand exchange with the selected chelator. Examples of suitable ligands for transchelation includes tartrate, citrate, gluconate, and heptagluconate. It will be appreciated that the conjugate can be labeled using the techniques described above, or alternatively, the chelator itself may be labeled and subsequently coupled to the peptide to form the conjugate; a process referred to as the "prelabeled chelate" method.

When labeled with diagnostically and/or therapeutically useful metals, peptide-chelator conjugates or pharmaceutically acceptable salts, esters, amides, and prodrugs of the present invention can be used to treat and/or detect cancers, including tumors, by procedures established in the art of radiodiagnostics and radiotherapeutics. [Bushbaum, 1995; Fischman et al., 1993; Schubiger et al., 1996; Lowbertz et al., 1994; Krenning et al., 1994]. A conjugate labeled with a radionuclide metal, such as technetium-99m, can be administered to a mammal, including human patients or subjects, by intravenous or intraperitoneal injection in a pharmaceutically acceptable carrier and/or solution such as salt solutions like isotonic saline. The amount of labeled conjugate appropriate for administration is dependent upon the distribution profile of the chosen conjugate iA the sense that a rapidly cleared conjugate may be administered in higher doses than one that clears less rapidly. Unit doses acceptable for Tc-99m imaging radiopharmaceuticals are in the range of about 5–40 mCi for a 70 kg individual. In vivo distribution and localization can be tracked by standard scintigraphic techniques at an appropriate time subsequent to administration; typically between thirty minutes and 180 minutes depending upon the rate of accumulation at the target site with respect to the rate of clearance at non-target tissue.

The compounds of the present invention can be administered to a patient alone or as part of a composition that contains other components such as excipients, diluents, radical scavengers, stabilizers, and carriers, all of which are well-known in the art. The compounds can be administered to patients either intravenously or intraperitoneally.

There are numerous advantages associated with the present invention. The compounds made in accordance with the present invention form stable, well-defined $^{99}$mTc or $^{186/188}$Re conjugate analogues of BBN agonists. Similar BBN agonist analogues can also be made by using appropriate chelator frameworks for the respective radiometals, to form stable-well-defined products labeled with $^{153}$Sm, $^{90}$Y, $^{166}$Ho, $^{105}$Rh, $^{199}$Au, $^{149}$Pm, $^{177L}$u, or $^{111}$In. The radiolabeled BBN agonist conjugates, selectively bind to neoplastic cells expressing GRP receptors, become internalized, and are retained in the tumor cells for extended time periods. Incorporating the spacer group between the metal chelator and the BBN agonist binding moiety maximizes the uptake and retention of the radioactive metal inside of the neoplasts or cancer cells. The radioactive material that does not reach (i.e., does not bind) the cancer cells is preferentially excreted efficiently into the urine with minimal radiometal retention in the kidneys.

Radiotherapeutics

The diagnostic application of these compounds can be as a first line diagnostic screen for the presence of neoplastic cell using scintigraphic imaging, as an agent for targeting neoplastic tissue using hand held radiation detection instrumentation in the field of radioimmuno guided surgery (RIGS), as a means to obtain dosimetry data prior to administration of the matched pair therapeutic compound, and as a means to assess GRP receptor population as a function of treatment over time.

The therapeutic application of these compounds can be defined either as an agent that will be used as a first line therapy in the treatment of cancer, as combination therapy where these radiolabeled agents could be utilized in conjunction with adjuvant chemotherapy, and as the matched pair therapeutic agent. The matched pair concept refers to one compound which can serve as both a diagnostic and a therapeutic agent depending on the radiometal with the appropriate chelate selected and can be understood in connection with the data set forth below.

Radioisotope therapy involves the administration of a radiolabeled compound in sufficient quantity to damage or destroy the targeted tissue. After administration of the compound (by e.g. intravenous or intraperitonal injection), the radiolabeled pharmaceutical localizes preferentially at the disease site (in this instance, tumor tissue that expresses the GRP-receptor). Once localized, the radiolabeled compound then damages or destroys the diseased tissue with the energy that is released during the radioactive decay of the isotope that is administered.

The design of a successful radiotherapeutic involves several critical factors:

1. selection of an appropriate targeting group to deliver the radioactivity to the disease site;
2. selection of an appropriate radionuclide that releases sufficient energy to damage that disease site, without substantially damaging adjacent normal tissues; and 3. selection of an appropriate combination of the targeting group and the radionuclide without adversely affecting the ability of this conjugate to localize at the disease site. For radiometals, this often involves a chelating group that coordinates tightly to the radionuclide, combined with a linker that couples said chelate to the targeting group, and that affects the overall biodistribution of the compound to maximize uptake in target tissues and minimizes uptake in normal, non-target organs.

The present invention provides radiotherapeutic agents that satisfy all three of the above criteria, through proper selection of targeting group, radionuclide, metal chelate and linker.

Radiotherapeutic agents may contain a chelated 3+metal ion from the class of elements known as the lanthanides (elements of atomic number 57–71) and their analogs (i.e. $M^{3+}$ metals such as yttrium and indium). Typical radioactive metals in this class include the isotopes 90-Yttrium, 111-Indium, 149-Promethium, 153-Samarium, 166-Dysprosium, 166-Holmium, 175-Ytterbium, and 177-Lutetium. All of these metals (and others in the lanthanide series) have very similar chemistries, in that they remain in the +3 oxidation state, and prefer to chelate to ligands that bear hard (oxygen/nitrogen) donor atoms, as typified by derivatives of the well known chelate DTPA (Diethylenetriaminepentaacetic acid) and polyaza-polycarboxylate macrocycles such as DOTA (1,4,7,10-tetrazacyclododecane-N, N',N'',N'''-tetraacetic acid and its close analogs. The structures of these chelating ligands, in their fully deprotonated form are shown below.

For radiotherapy applications, forms of the DOTA chelate [Tweedle MF, Gaughan GT, Hagan JT, "1-Substituted-1,4,7-triscarboxymethyl-1,4,7,10-tetraazacyclododecane and analogs." U.S. Pat. No. 4,885,363, Dec. 5, 1989] are particularly preferred, as the DOTA chelate is expected to de-chelate less in the body than DTPA or other linear chelates.

General methods for coupling DOTA-type macrocycles to targeting groups through a linker (e.g. by activation of one of the carboxylates of the DOTA to form an active ester, which is then reacted with an amino group on the linker to form a stable amide bond), are known to those skilled in the art. (See e.g. Tweedle et al. U.S. Pat. No. 4,885,363). Coupling can also be performed on DOTA-type macrocycles that are modified on the backbone of the polyaza ring.

The selection of a proper nuclide for use in a particular radiotherapeutic application depends on many factors, including:

a. Physical half-life—This should be long enough to allow-synthesis and purification of the radiotherapeutic construct from radiometal and conjugate, and delivery of said construct to the site of injection, without significant radioactive decay prior to injection. Preferably, the radionuclide should have a physical half-life between about 0.5 and 8 days.

b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby pro-

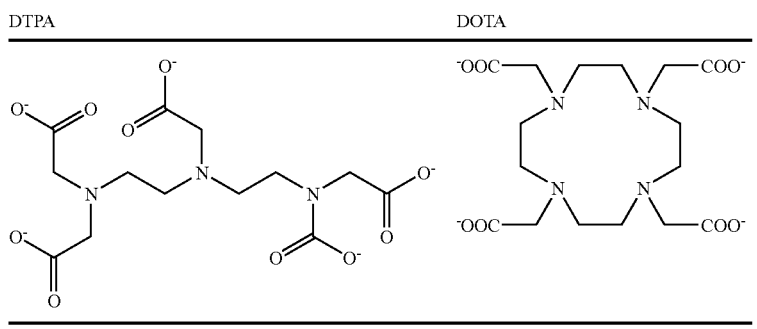

DTPA                DOTA

These chelating ligands encapsulate the radiometal by binding to it via multiple nitrogen and oxygen atoms, thus preventing the release of free (unbound) radiometal into the body. This is important, as in vivo dissociation of +3 radiometals from their chelate can result in uptake of the radiometal in the liver, bone and spleen (Brechbiel MW, Gansow OA, "Backbone-substituted DTPA ligands for $^{90}Y$ radioimmunotherapy", Bioconj. Chem. 1991; 2:187–194; Li, WP, Ma DS, Higginbotham C, Hoffman T, Ketring AR, Cutler CS, Jurisson, SS, "Development of an in vitro model for assessing the in vivo stability of lanthanide chelates." Nucl. Med. Biol. 2001; 28(2): 145–154; KasokatT, Urich K. Arzneim.-Forsch, "Quantification of dechelation of gadopentetate dimeglumine in rats". 1992; 42(6): 869–76]. Unless one is specifically targeting these organs, such non-specific uptake is highly undesirable, as it leads to non-specific irradiation of non-target tissues, which can lead to such problems as hematopoietic suppression due to irradiation of bone marrow.

ducing highly localized damage. Beta emitting radionuclides are particularly preferred, as the energy from beta particle emissions from these isotopes is deposited within 5 to about 150 cell diameters. Radiotherapeutic agents prepared from these nuclides are capable of killing diseased cells that are relatively close to their site of localization, but cannot travel long distances to damage adjacent normal tissue such as bone marrow.

c. Specific activity (i.e. radioactivity per mass of the radionuclide)—Radionuclides that have high specific activity (e.g. generator produced 90-Y, 111-In, 177-Lu) are particular preferred. The specific activity of a radionuclide is determined by its method of production, the particular target that is used to produce it, and the properties of the isotope in question.

Many of the lanthanides and lanthanoids include radio-isotopes that have nuclear properties that make them suitable for use as radiotherapeutic agents, as they emit beta particles. Some of these are listed in the table below.

| Isotope | Half-Life (days) | Max β-energy (MeV) | Gamma energy (keV) | Approximate range of b-particle (cell diameters) |
|---|---|---|---|---|
| 149-Pm | 2.21 | 1.1 | 286 | 60 |
| 153-Sm | 1.93 | 0.69 | 103 | 30 |
| 166-Dy | 3.40 | 0.40 | 82.5 | 15 |
| 166-Ho | 1.12 | 1.8 | 80.6 | 117 |
| 175-Yb | 4.19 | 0.47 | 396 | |
| 177-Lu | 6.71 | 0.50 | 208 | 20 |
| 90-Y | 2.67 | 2.28 | — | 150 |
| 111-In | 2.810 | Auger electron emitter | 173,247 | <5 μm |

Pm: promethium, Sm: samarium, Dy: dysprosium, Ho: holmium, Yb: ytterbium, Lu: Lutetium, Y: yttrium, In: Indium Methods for the preparation of radiometals such as beta-emittging lanthanide radioisotopes are known to those skilled in the art, and have been described elsewhere [e.g. Cutler C S, Smith C J, Ehrhardt G J.; Tyler T T, Jurisson S S, Deutsch E. "Current and potential therapeutic uses of lanthanide radioisotopes." Cancer Biother. Radiopharm. 2000; 15(6): 531–545]. Many of these isotopes can be produced in high yield for relatively low cost, and many (e.g. 90—Y, 149—Pm, 177—Lu) can be produced at close to carrier-free specific activities (i.e. the vast majority of atoms are radioactive). Since non-radioactive atoms can compete with their radioactive analogs for binding to receptors on the target tissue, the use of high specific activity radioisotope is important, to allow delivery of as high a dose of radioactivity to the target tissue as possible.

Radiotherapeutic derivatives of the invention containing beta-emitting isotopes of rhenium (186—Re and 188—Re) are also particularly preferred.

Proper dose schedules for the radiotherapeutic compounds of the present invention are known to those skilled in the art. The compounds can be administered using many methods which include, but are not limited to, a single or multiple IV or IP injections, using a quantity of radioactivity that is sufficient to cause damage or ablation of the targeted GRP-R bearing tissue, but not so much that substantive damage is caused to non-target (normal tissue). The quantity and dose required is different for different constructs, depending on the energy and half-life of the isotope used, the degree of uptake and clearance of the agent from the body and the mass of the tumor. In general, doses can range from a single dose of about 30–50 mCi to a cumulative dose of up to about 3 Curies.

The radiotherapeufic compositions of the invention can include physiologically acceptable buffers, and can require radiation stabilizers to prevent radiolytic damage to the compound prior to injection. Radiation stabilizers are known to those skilled in the art, and may include, for example, para-aminobenzoic acid, ascorbic acid, gentistic acid and the like.

The following examples are presented to illustrate specific embodiments and demonstrate the utility of the present invention.

Experimental Section

EXAMPLE 1

Synthesis and in vitro binding assessment of synthetic BBN analogues employing hydrocarbon chain spacers A. Synthesis:

Many BBN analogues were synthesized by Solid Phase Peptide Synthesis (SPPS). Each peptide was prepared by SPPS using an Applied Biosystems Model 432A peptide synthesizer. After cleavage of each BBN analogue from the resin using Thfluoracetic acid (TFA), the peptides were purified by C18 reversed-phase HPLC using a Vydac HS54 column and $CH_3CN/H_2O$ containing 0.1% TFA as the mobile phase. After collection of the fraction containing the desired BBN peptide (approx. 80–90% yield in most cases), the solvent was evaporated. The identity of each BBN peptide was confirmed by FAB-mass spectrometry, Department of Chemistry—Washington University, St. Louis, Mo.

Figure 5:
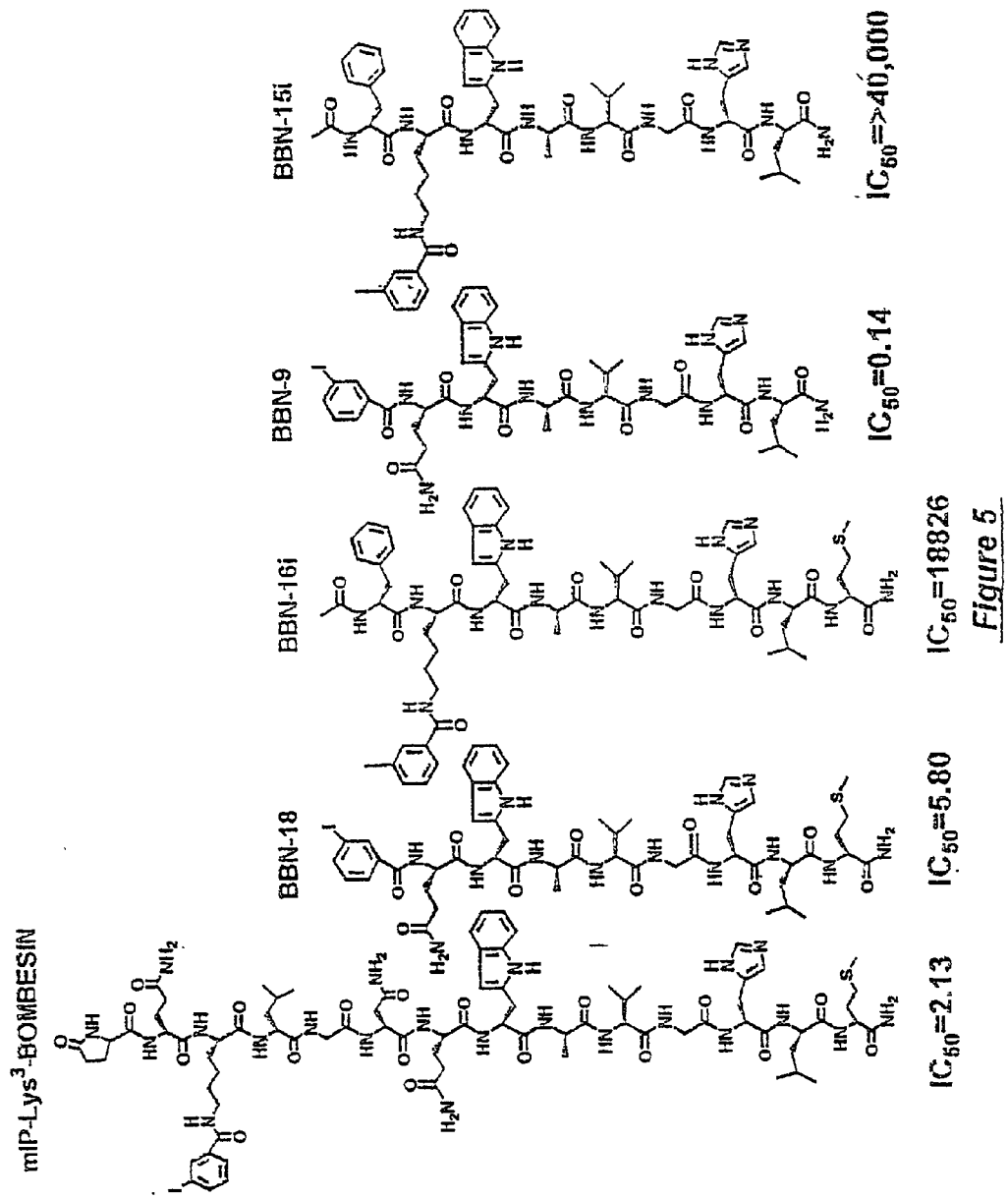
FIG. 5 illustrates several iodinated bombesin analogues including their IC$_5$'s.

Various amino acid sequences (in some cases including different chemical moieties) were conjugated to the N-terminal end of the BBN binding region (i.e., to BBN-8 or Trp8). BBN analogue numbers 9,15,15i, 16, 16i and 18 were synthesized as examples of N-terminal modified peptides as shown in FIG. 5.

Figure 6:
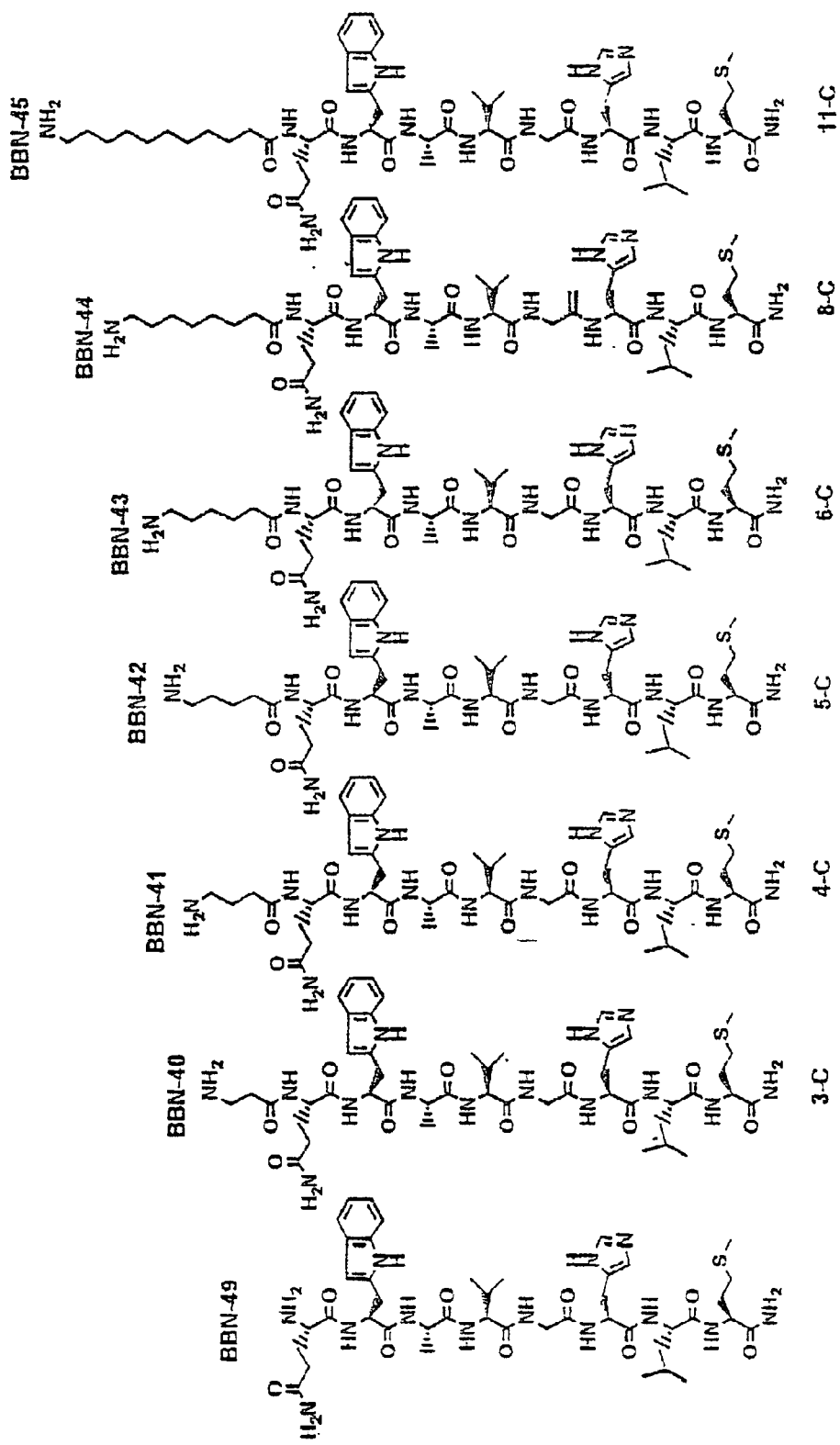
FIG. 6 illustrates several tethered bombesin analogues.

Various tethered N-terminal (via Trp8) BBN analogues were also synthesized by SPPS as exemplified by BBN-40, BBN-41, BBN-42, BBN-43, BBN-44, BBN-45, and BBN-49 as shown in FIG. 6. In these particular tethered peptides, a Glu residue was attached to Trp8 followed by attachment of fmoc protected terminal amine groups separated from a —COOH group by 3-, 4-, 5-, 6-, 8- and 11-carbon chain (CH) spacers (FIG. 6). These fmoc protected acids were added as the terminal step during the SPPS cycle. As described previously, each of the BBN analogues was purified by reversed-phase HPLC and characterized by high resolution Mass Spectroscopy. Peptide 49 employed only glutamine as the spacer group.

Figure 7:
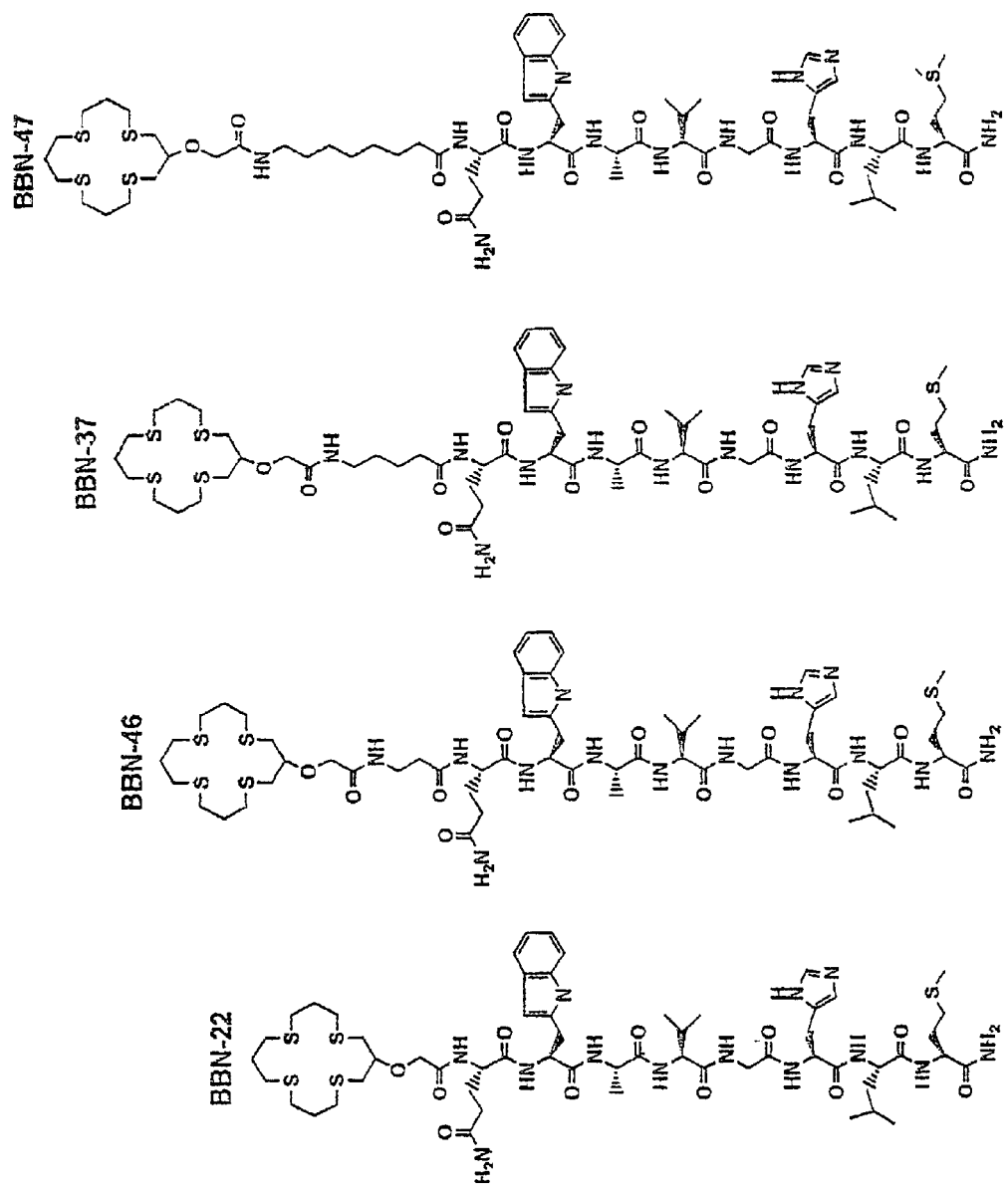
FIG. 7 illustrates several [16]aneS$_4$ bombesin analogues.

The [16]aneS4 macrocyclic ligand was conjugated to selected tethered BBN analogues shown in FIG. 6. The —$OCH_2COOH$ group on the [16]aneS4 macrocycle derivative was activated via HOBt/HBTU so that it efficiently formed an amide bond with the terminal $NH_2$ group on the spacer side arm (following deprotection). The corresponding [16]aneS$_4$tethered BBN derivatives were produced and examples of 4 of these derivatives (i.e., BBN-22, -37, -46 and -47) are shown in FIG. 7. As previously described, each [16]aneS$_4$ BBN derivative was purified by reversed phase HPLC and characterized by FAB Mass Spectroscopy.

B. In Vitro Binding Affinities

The binding affinities of the synthetic BBN derivatives were assessed for GRP receptors on Swiss 3T3 cells and, in some cases, on a variety of human cancer cell lines, that express GRP receptors. The $IC_{50}$ value of each derivative was determined relative to (i.e., in competition with) $^{125}$I-Tyr$_4$-BBN (the Kd for 125I-Tyr$_4$-BBN for GRP receptors in Swiss 3T3 cells is reported to be 1.6+0.4 nM) [Zueht et al., 1991]. The cell binding assay methods used to measure the $IC_{50}$'s is standard and used techniques previously reported [Jensen et al., 1993; Cai et al., 1994; Cai et al., 1992]. The methods used for determining $IC_{50}$'s for all GRP receptor binding compounds on all cell lines was similar. The specific method used to measure $IC_{50}$'s on Swiss 3T3 cells is briefly described as follows:

Swiss 3T3 mouse fibroblasts are grown to confluence in 48 well microtiter plates. An incubation media was prepared consisting of HEPES (1 1.916g/l), NaCI (7.598 g/l), KCI (0.574 g/l), MgCI2 (1.106 g/l), EGTA (0.380 g/l), BSA (5.0 g/l), chymostatin (0.002 g/l), soybean trypsin inhibitor (0.200 g/l), and bacitracin (0.050 g/l). The growth media was removed, the cells were washed twice with incubation media, and incubation media was returned to the cells. $^{25}$1-Tyr4-BBN (0.01 uCi) was added to each well in the presence of increasing concentrations of the appropriate competitive peptide. Typical concentrations of displacing peptide ranged from 10–12 to 10–5 moles of displacing ligand per well. The cells were incubated at 37° C. for forty minutes in a 95%0$_2$/5%C0$_2$ humidified environment. At forty minutes post initiation of the incubation, the medium was discarded, and the cells were washed twice with cold incubation media. The cells were harvested from the wells following incubation in a trypsin/EDTA solution for five minutes at 37° C. Subsequently, the radioactivity, per well, was determined and the maximum % total uptake of the radiolabeled peptide was determined and normalized to 100%.

Figure 8:
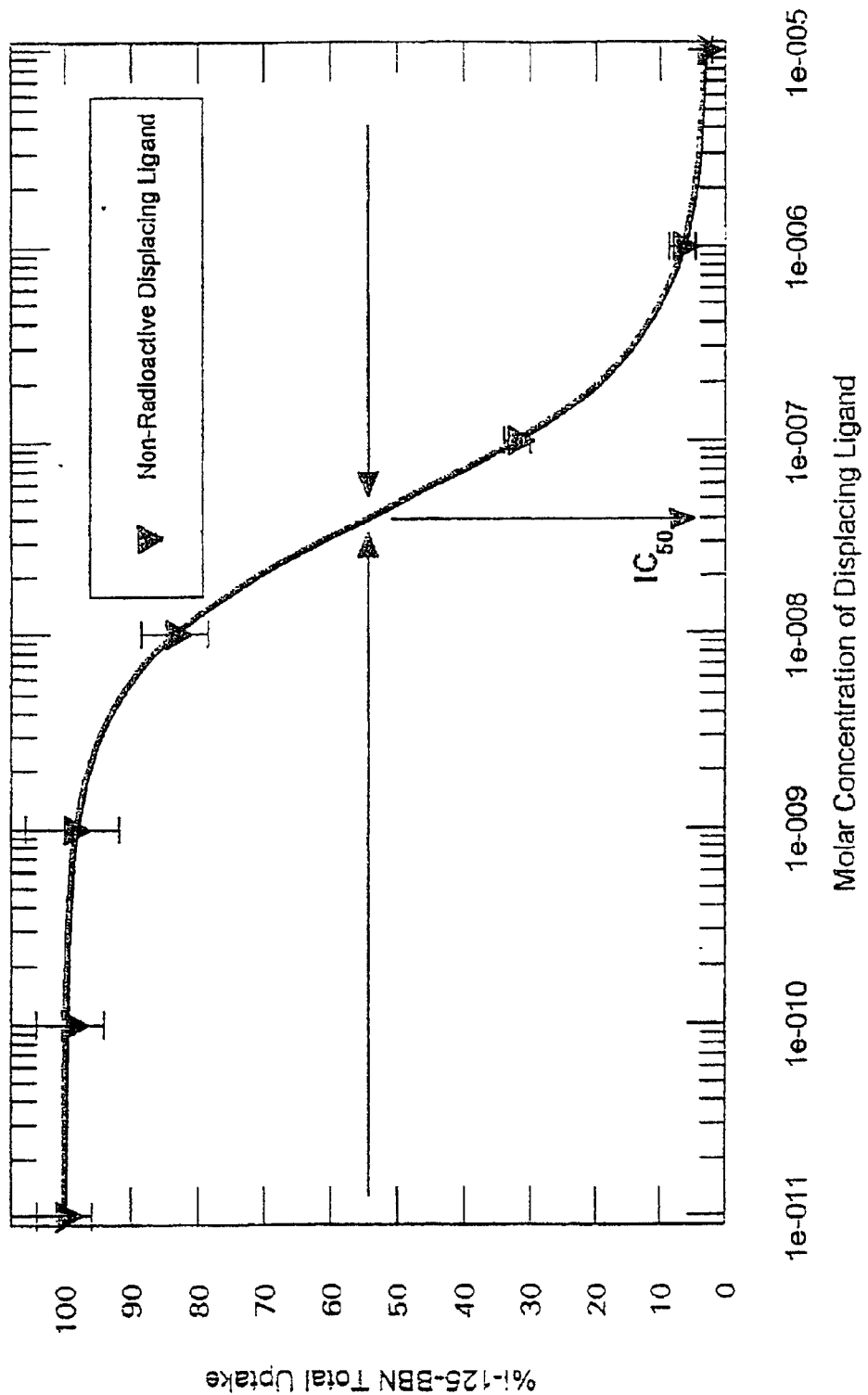
FIG. 8 is a graph illustrating lC$_{50}$ analysis wherein %-I-125-BBN total uptake versus molar concentration of displacing ligand is shown.

C. Results of Binding AfFinity Measurements:

The IC$_{50}$ values measured for the BBN derivatives synthesized in accordance with this invention showed that appending a peptide side chain and other moieties via the N-terminal BBN-8 residue (i.e., Trp$^8$) produced widely varying ICs values. For example, see IC$_{50}$ values shown for BBN 11, 15i, 16i, and 18 in FIGS. 5 and 8. The observations are consistent with previous reports showing highly variable IC$_{50}$ values when derivatizing BBN(8–13) or BBN(8–14) with a predominantly short chain of amino acid residues [Hoffken, 1994]. In contrast, when a hydrocarbon spacer of 3- to 11-carbons was appended between BBN(7–14) and the [16]aneS$_4$ macrocycle, the IC$_{50}$'s were found to be surprisingly relatively constant and in the 1–5 nM range. The following IC$_{50}$values were obtained fro the unmetallated compounds BBN-22, -37, -46, and -47 (structures shown in FIG. 7).

| COMPOUND | IC$_{50}$ (nM) |
| --- | --- |
| BBN-22 | 3.01 ± 0.21 |
| BBN-37 | 1.79 ± 0.09 |
| BBN-46 | 2.34 ± 0.53 |
| BBN-47 | 4.19 ± 0.91 |

These data suggest that using relatively simple spacer groups to extend ligands some distance from the BBN binding region [e.g., BBN(8–14)] can produce derivatives that maintain binding affinities in the 1–5 nmolar range.

Figure 9:
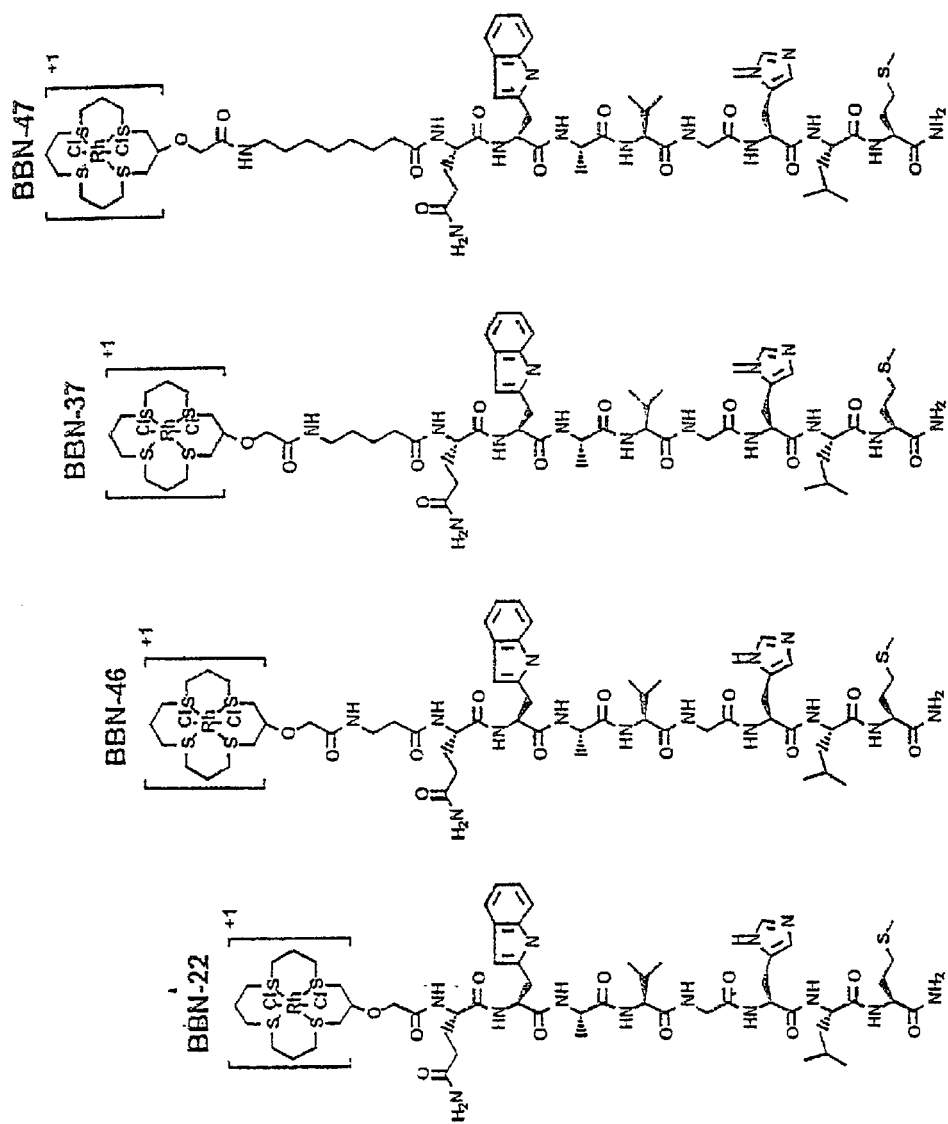
FIG. 9 illustrates several Rhodium-[16]aneS$_4$ bombesin analogues.

D. Cell Binding Studies With Metal Complexes:

The following IC$_{50}$ values were obtained for the metallated Rhodium complexes shown on FIG. 9.

| COMPOUND | IC$_{50}$ (nM) |
| --- | --- |
| RhCl$_2$BBN-22 | 37.5 ± 10.5 |
| RhCl$_2$BBN-37 | 4.76 ± 0.79 |
| RhCl$_2$BBN-46 | 3.38 ± 0.69 |

The results illustrated in FIG. 9 show that when the RhCl$_2$-[16]aneS$_4$ complexes separated from Trp$^8$ by only a glutamine (Glu$^7$), the IC$_{50}$ of this conjugate (i.e., Rh-BBN-22) was 37.5 nM. However, when a five (5) carbon spacer or an eight (8) carbon spacer was present (i.e., Rh-BBN-37 and Rh-BBN47), the IC$_{50}$'s remained below 5 nM. These data demonstrate that a straight chain spacer (along with glu$^7$) to move the +1 charged Rh-S$_4$-chelate away from the BBN binding region will result in a metallated BBN analogue with sufficiently high binding affinities to G RP receptors for in vivo tumor targeting applications.

Figure 10:
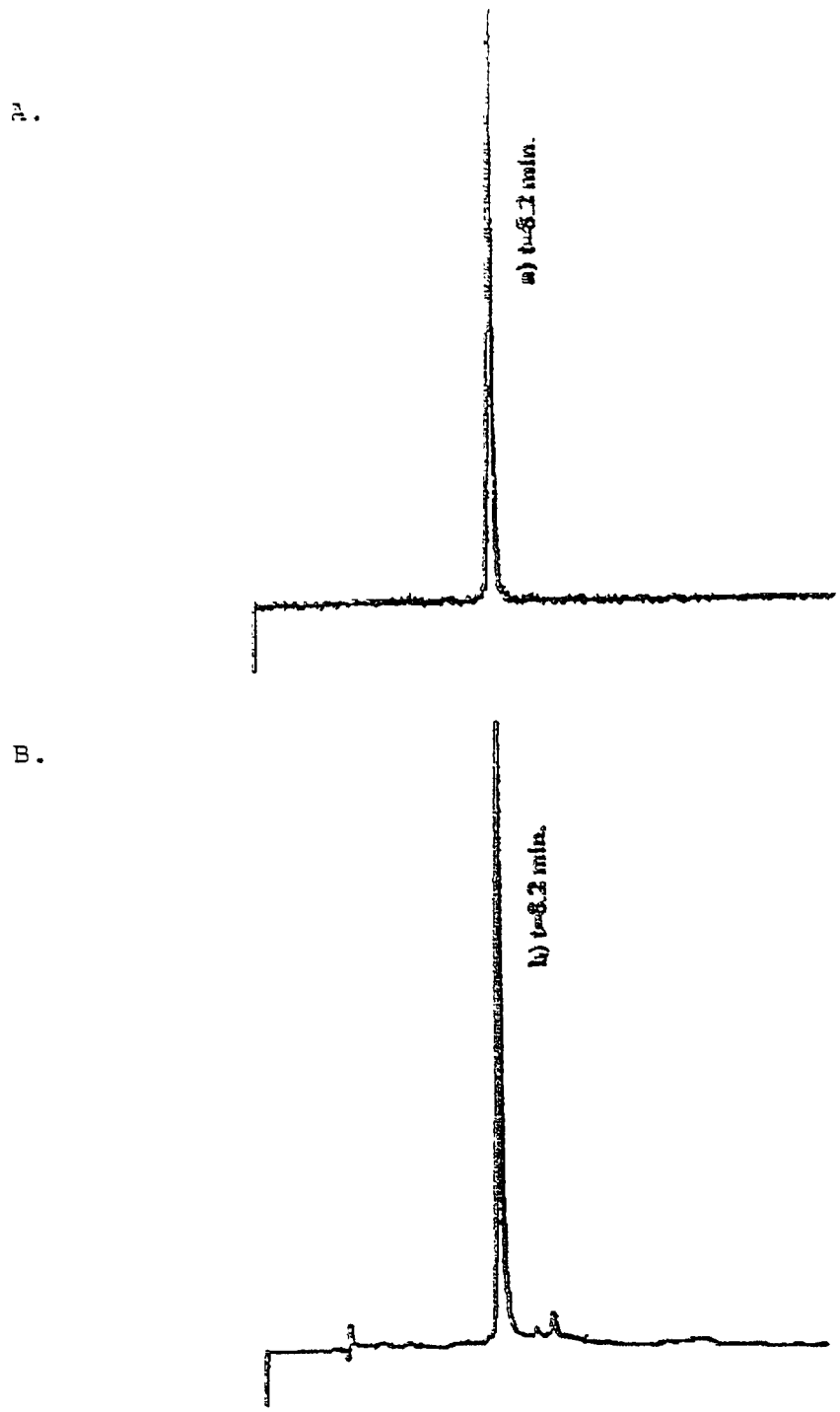
FIG. 10 illustrates an HPLC chromatogram of Rhodium-BBN-37 wherein (A) illustrates $^{105}RhCl_2$-BBN-37 and (B) illustrates RhCl$_2$-BBN-37.

E. $^{105}$Radiolabeled BBN Analogues:

The $^{105}$Rh conjugates of BBN-22, BBN-37, BBN46 and BBN-47 were synthesized using a $^{105}$Rh-chloride reagent from the Missouri University Research Reactor (MURR). This reagent was obtained as $^{105}$Rh-chloride, a no-carrier-added (NCA) product, in 0.1–1 M HCl. The pH of this reagent was adjusted to 4–5 using 0.1–1.0 M NaOH dropwise and it was added to approximately 0.1 mg of the [1 6]aneS$_4$-conjugated BBN derivatives in 0.9% aqueous NaCl and 10% ethanol. After the sample was heated at 80° C for one hour, the $^{105}$Rh-BBN analogues were purified using HPLC. In each case, a NCA or high specific activity product was obtained since the non-metallated S$_4$-BBN conjugates eluted at a retention time well after the $^{105}$Rh-BBN conjugates eluted. For example, the retention time of $^{105}$Rh-BBN-37 was 7.1 minutes while BBN-37 eluted at 10.5 minutes from a C-18-reversed phase column eluted with CH$_3$CNIH$_2$O containing 0.1% TFA as shown in FIGS. 10A–B.

EXAMPLE 2

Retention of $^{105}$Rh-BBN Analogues in Cancer Cells

Once the radiometal has been specifically "delivered" to cancer cells (e.g., employing the BBN binding moiety that specifically targets GRP receptors on the cell surface), it is necessary that a large percentage of the "delivered" radioactive atoms remain associated with the cells for a period time of hours or longer to make an effective radiopharmaceutical for effectively treating cancer. One way to achieve this association is to internalize the radiolabeled BBN conjugates within the cancer cell after binding to cell surface GRP receptors.

Figure 11:
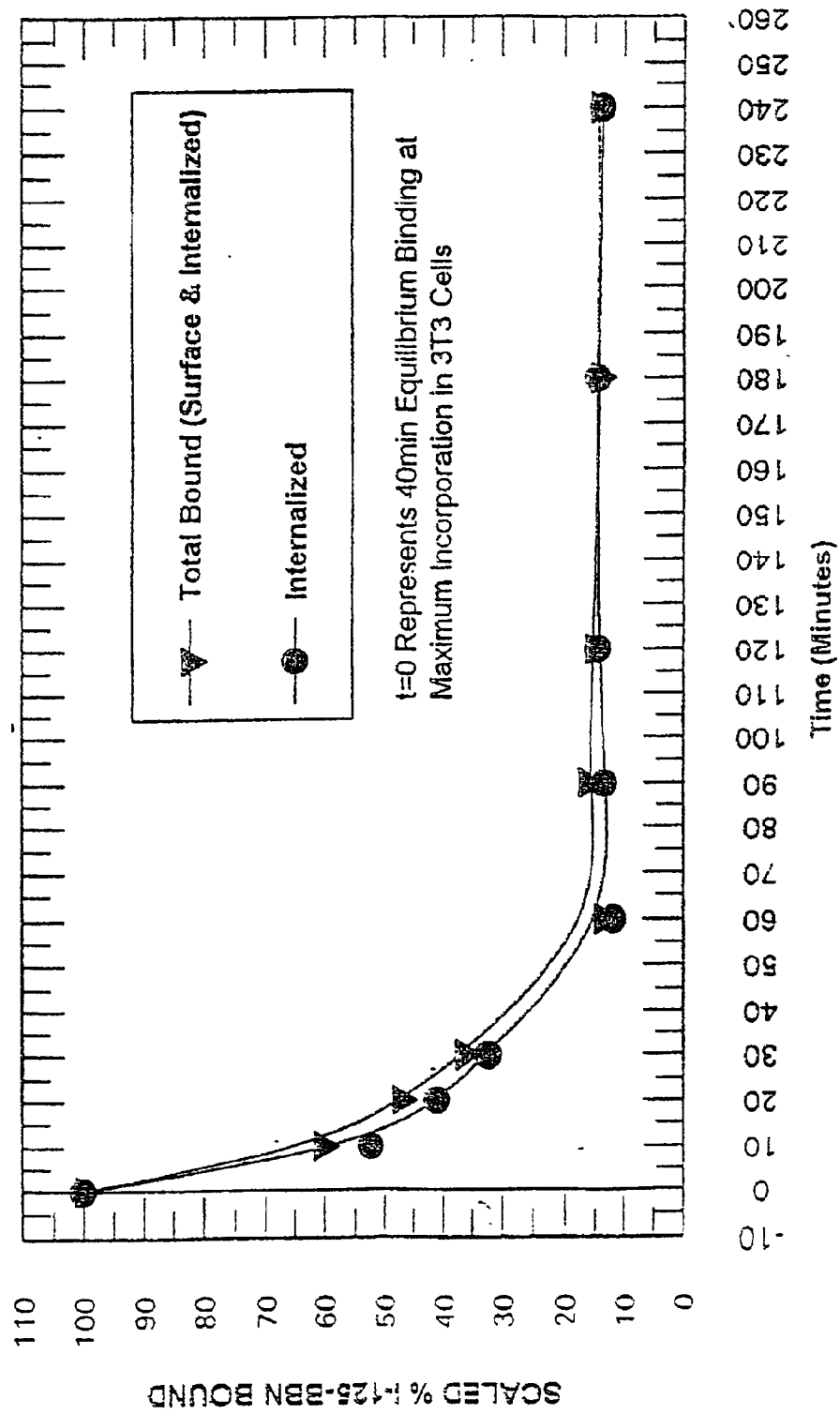
FIG. 11 is a graph illustrating $^{125}I$-Tyr$^4$-bombesin internalization efflux from Swiss 3T3 cells.

In the past, all of the work with synthetic-BBN analogues for treatment of cancers focused on synthesizing and evaluating antagonists [Davis et al., 1992; -Hoffken, 1994; Moody et al., 1996; Coy et al., 1988; Cai et al., 1994; Moody et al., 1995; Leban et al., 1994; Cai et al., 1992]. After evaluating synthetic BBN analogues that would be predicted to be either agonists or antagonists, applicants found that derivatives of BBN(8–14) (i.e., those with the methionine or amidated methionine at BBN-14) are rapidly internalized (i.e., in less than two minutes) after binding to the cell surface GRP receptors. Several radiolabeled BBN(8–14) analogues that were studied to determine their internalization and intracellular trapping efficiencies were radioiodinated (i.e., $^{125}$I) derivatives. The results of these studies demonstrated that despite rapid internalization after $^{125}$I-labeled BBN analogue binding to GRP receptors in Swiss 3T3 cells, the $^{125}$I was rapidly expelled from the cells [Hoffman et al., 1997] as shown in FIG. 11. Thus, these $^{125}$I-BBN derivatives were not suitable for further development.

In contrast, the $^{105}$Rh-BBN(8–14) derivatives that bind to GRP receptors are not only rapidly internalized, but there is a large percentage of the $^{105}$Rh activity that remains trapped within the cells for hours (and in some cell lines>twenty four hours). This observation indicates that these radiometallated BBN derivatives have real utility as radiopharmaceuticals for in vivo targeting of neoplasms expressing GRP receptors.

Experiments designed to determine the fraction of a radiotracer internalized within cells were performed by adding excess $^{125}$I—or $^{105}$Rh-BBN derivatives to the cell incubation medium. After establishment of equilibrium after a forty minute incubation, the media surrounding the cells was removed and the cells were washed with fresh media containing no radioactivity. After washing, the quantity of radioactivity associated with the cells was determined (i.e., total counts per minute (TCPM) of $^{125}$I or $^{105}$Rh associated with the cells). The cells were then incubated in a 0.2M acetic acid solution (pH 2.5) which caused the surface proteins (incl., GRP receptors) to denature and release all surface bound radioactive materials. After removing this buffer and washing, the cells were counted again. The counts per minute (c.p.m.) associated with the cells at that point were only related to the 251 or ORh that remained trapped inside of the cells.

Figure 12:
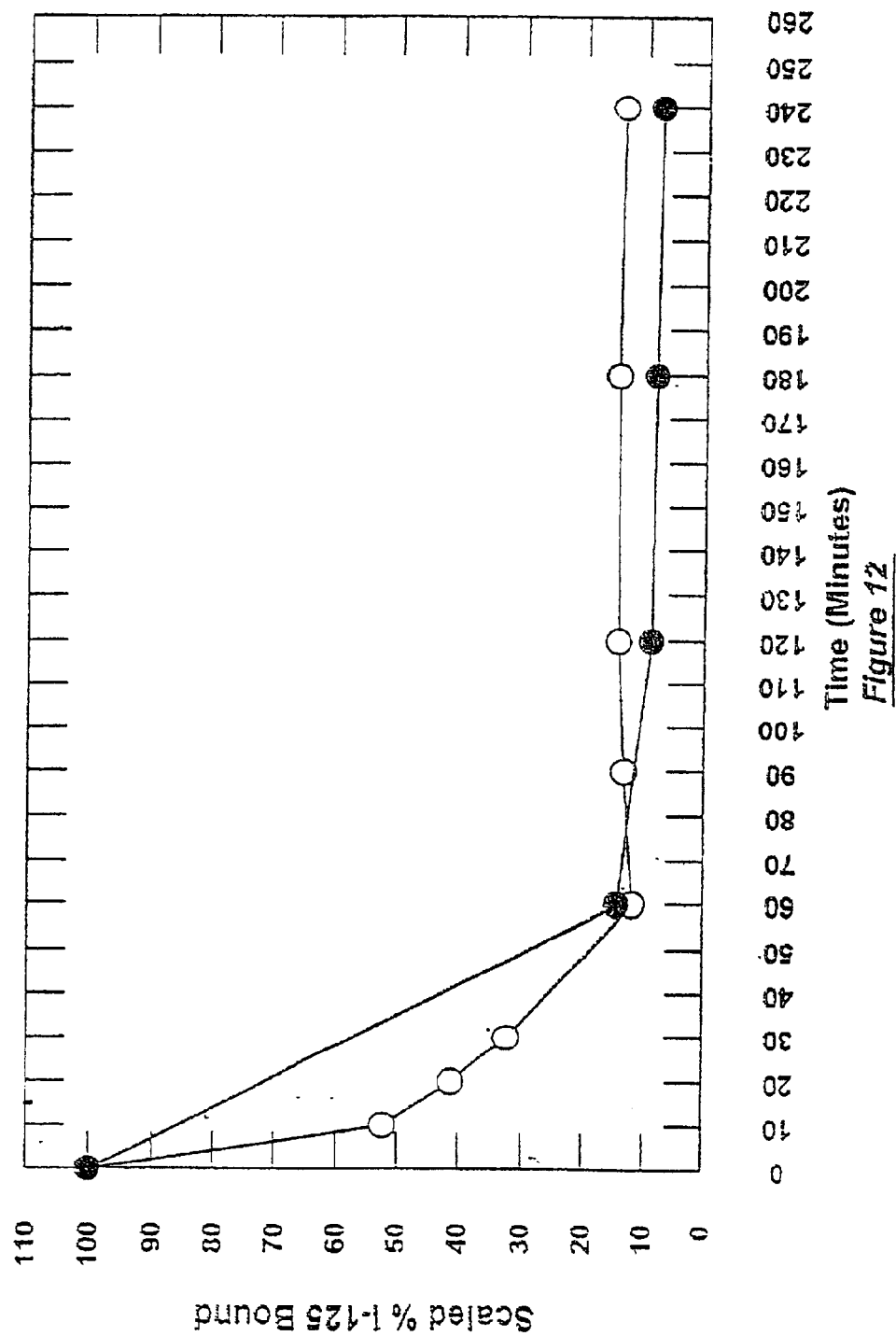
FIG. 12 illustrates I-125 bombesin internalization efflux in I-125 free bufferwherein $^{125}I$-Tyr$^4$-BBN vs. $^{125}I$-Lys$^3$-BBN efflux from Swiss 3T3 cells is shown.

To determine intracellular retention, a similar method was employed. However, after washing the cells with fresh (non-radioactive) incubation media, the cells were incubated in the fresh media at different time periods after washing away all extracellular $^{125}$I—or $^{105}$Rh-BBN analogues. After each time period, the methods used to determine TOTAL c.p.m. and intracellular c.p.m. after washing with a 0.2M acetic acid solution at pH 2.5 were the same as described above and the percent $^{125}$I or $^{105}$Rh remaining trapped inside of the cells was calculated. FIG. 12 is a graph of results of efflux experiments using Swiss 3T3 cells with $^{125}$I-Lys$^3$-BBN. The results show that there is rapid efflux of the 1251 from inside of these cells with less than 50% retained at fifteen minutes and by sixty minutes, less than 20% remained as shown in FIG. 12.

Figure 13:
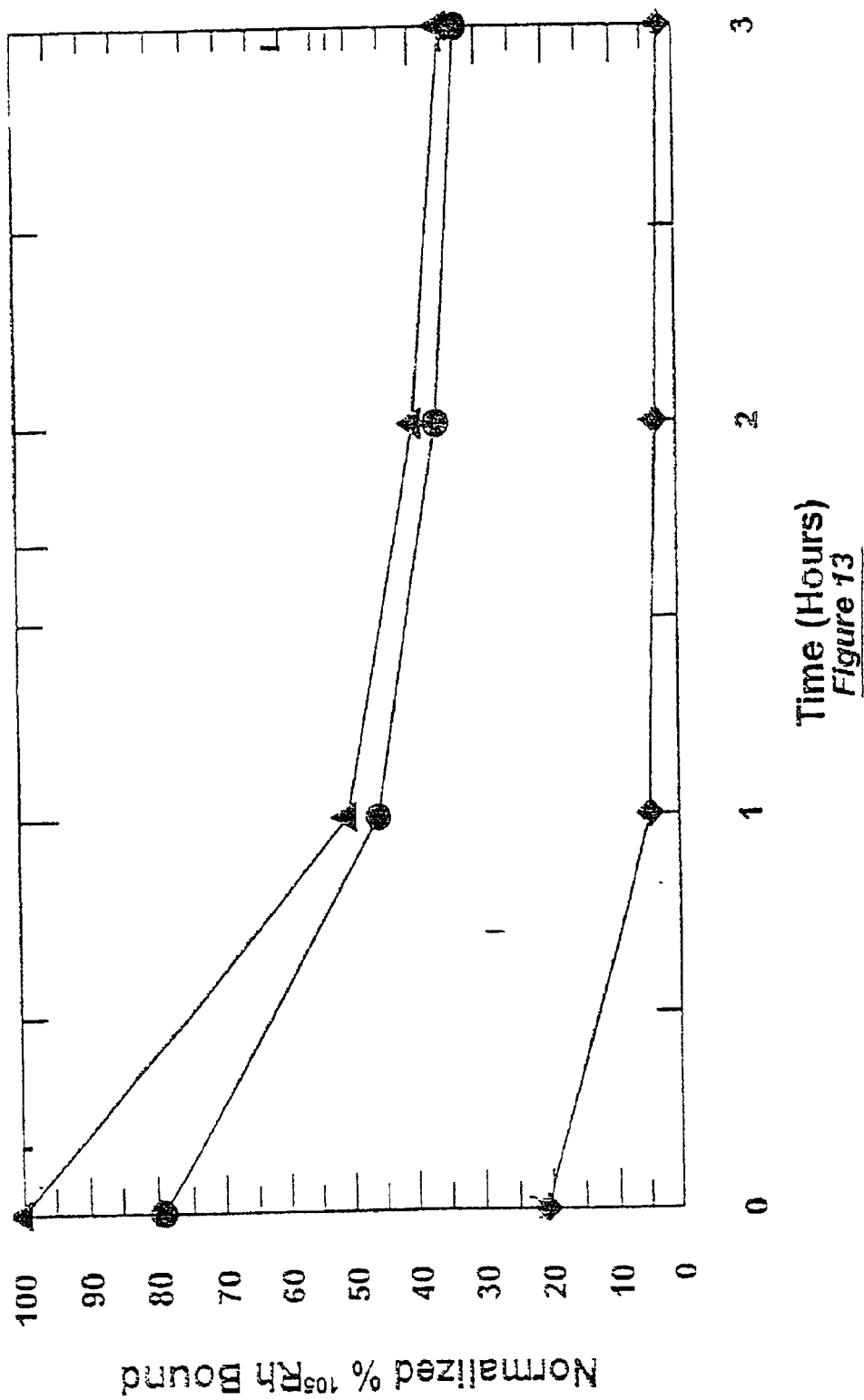
FIG. 13 is a graph illustrating the efflux of $^{105}Rh$-BBN-37 from Swiss 3T3 cells.

In contrast, studies with all of the $^{105}$Rh-[16]aneS$_4$-BBN agonist derivatives that are internalized inside of the cells showed substantial intracellular retention of $^{105}$Rh by the GRP receptor expressing cells. For example, results of studies using $^{105}$Rh-BBN-37 (see FIG. 9) in conjunction with Swiss 3T3 cells showed that approximately 50% of the $^{105}$Rh activity remains associated with the cells at sixty minutes post-washing and approximately 30% of $^{105}$Rh remained inside of the cells after four hours as shown in FIG. 13. Note that at least 5% of the $^{105}$Rh is surface bound at >sixty minutes.

Figure 14:
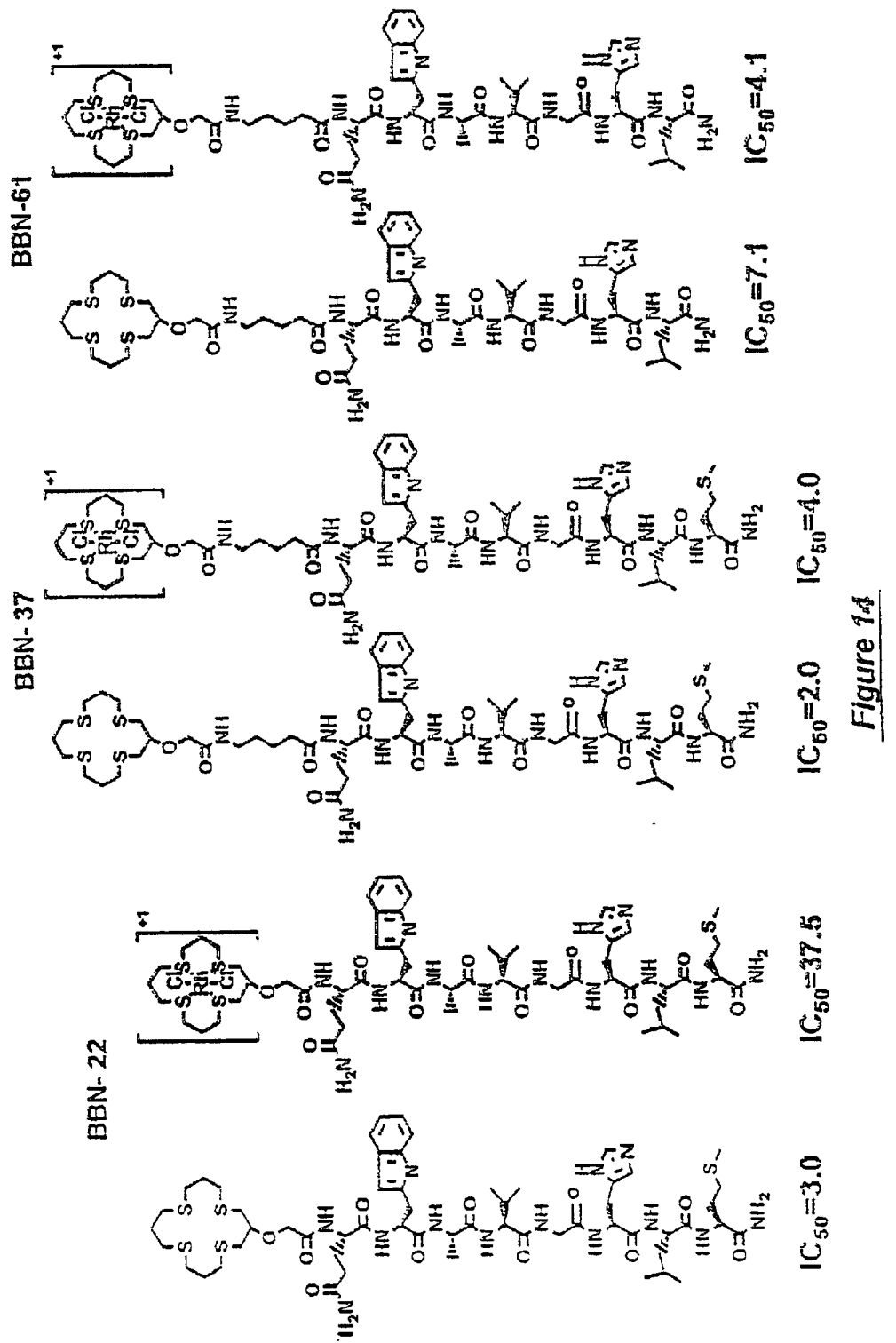
FIG. 14 illustrates several $^{105}$Rhodium bombesin analogues including their IC$_{50}$'s.
Figure 15:
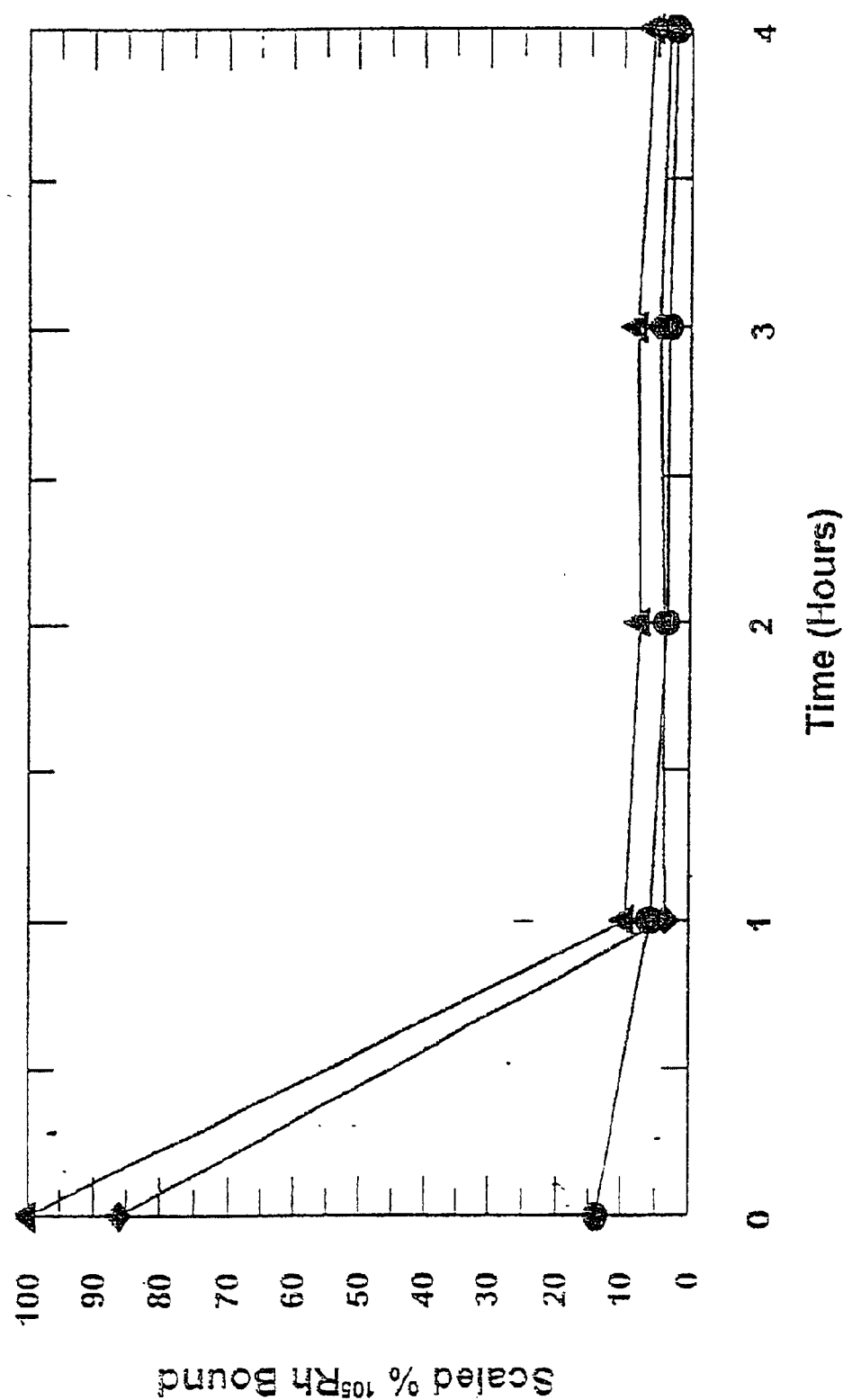
FIG. 15 is a graph illustrating $^{105}Rh$-BBN-61 efflux from Swiss 3T3 cells.
Figure 16:
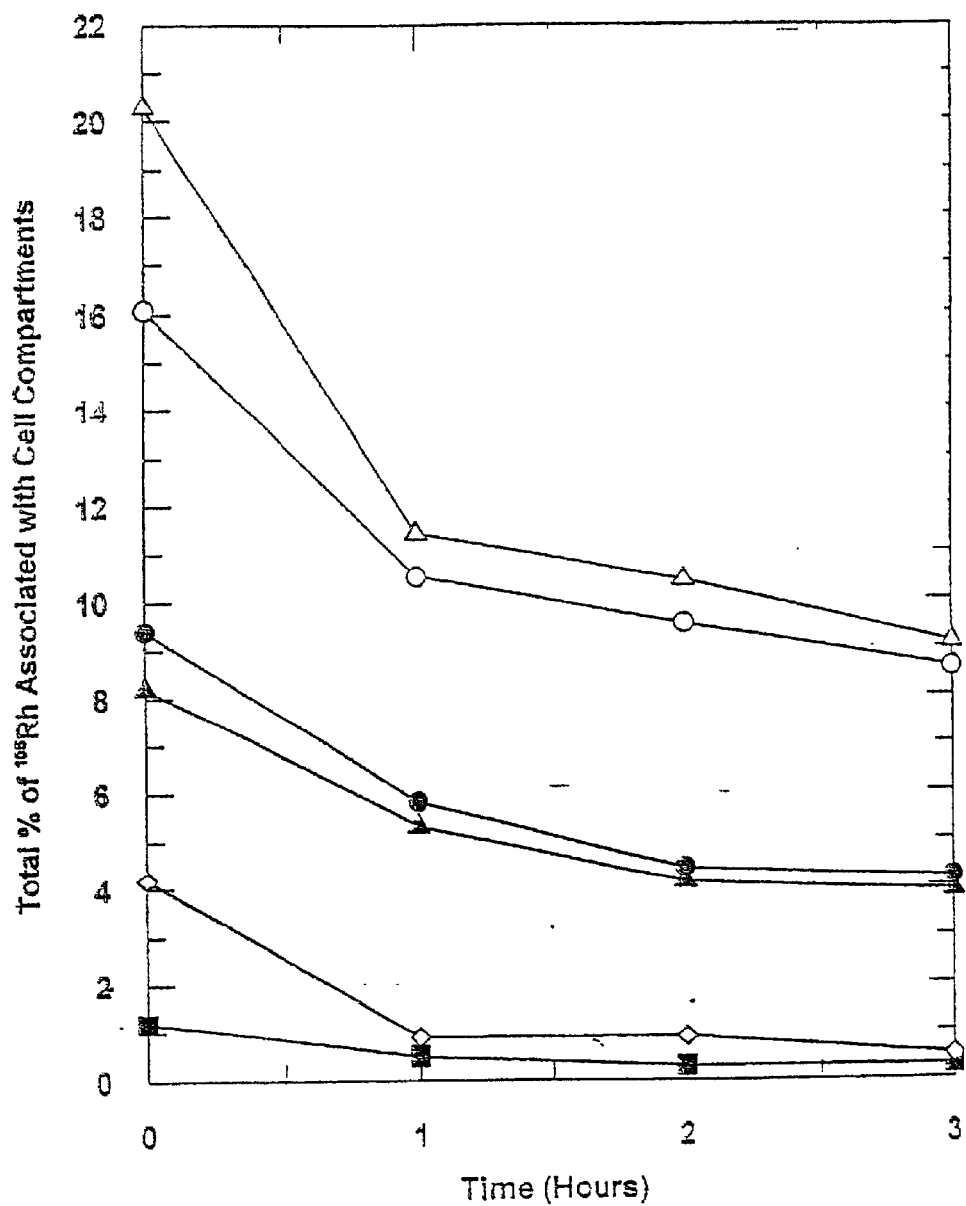
FIG. 16 is a graph illustrating the efflux of $^{105}Rh$-BBN-22 vs. $^{105}Rh$-BBN-37 from Swiss 3T3 cells.
Figure 18:
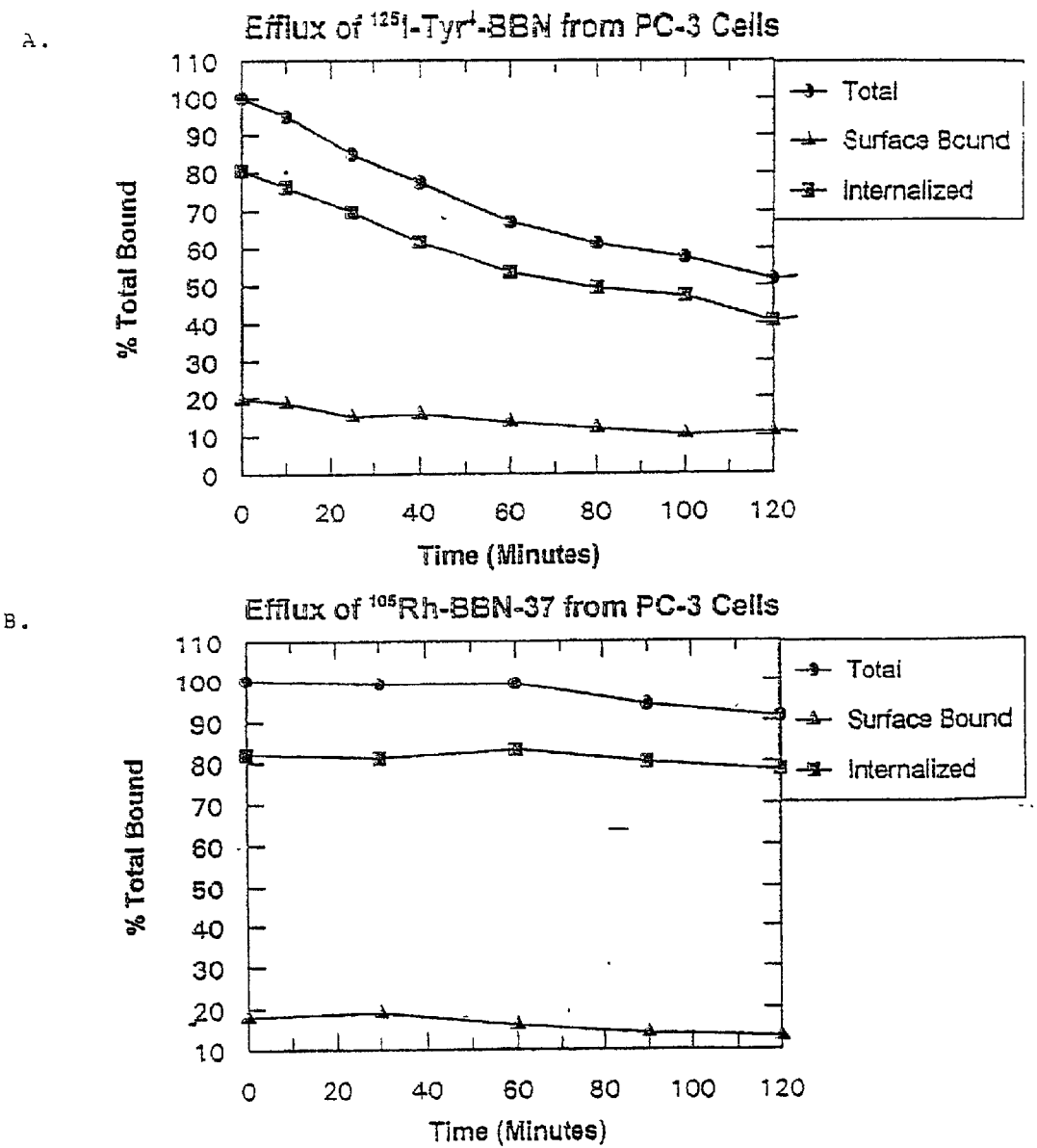
FIG. 18 are graphs illustrating Prostate CA cell binding wherein (A) illustrates the efflux of $^{125}I$-Tyr$^4$-BBN from PC-3 cells and (B) illustrates the efflux of $^{105}Rh$-BBN-37 from PC-3 cells.

The $^{105}$Rh-BBN derivatives shown in FIG. 9 all have an amidated methionine at position BBN-14 and are expected to be agonists [Jensen et al., 1993]. Therefore, they would be predicted to rapidly internalize after binding to GRP receptors on the cell surface [Reile et al., 1994; Bjisterbosch et al., 1995; Smythe et al., 1 991], which was confirmed by applicants' data. Referring to FIG. 14, $^{105}$Rh-BBN-61, a BBN analogue with no amino acid at position BBN-14 (i.e., a $^{105}$Rh-BBN(8–13) derivative), was synthesized and studied. This BBN analogue has a high bonding affinity (i.e., IC$_{50}$ =4.1 nM). This type of derivative is expected to be an antagonist and as such will not internalize [Jensen et al., 1993; Smythe et al., 1991]. Results of efflux studies with $^{105}$Rh-BBN-61 using Swiss 3T3 cells showed that immediately following washing with fresh incubation buffer (i.e., t=0), essentially all of the $^{105}$Rh associated with these cells is on the cell surface, as expected. Furthermore, after only one hour of incubation, less than 10% remained associated with these cells in any fashion (comparing the results with the antagonist (see FIG. 15) to those of the agonist (see FIG. 16)). These data indicate that $^{105}$Rh-antagonists with structures similar to the $^{105}$Rh-BBN agonists (i.e., those shown in FIG. 9) are not good candidates for development of radiopharmaceuticals since they are neither trapped in nor on the GRP receptor expressing cells to nearly the same extent as the radiometallated BBN agonists.

EXAMPLE 3
Human Cancer Cell Line Studies

In vitro cell binding studies of $^{105}$Rh-BBN-37 with two different human cancer cell lines that express GRP receptors (i.e., CF-PAC1 and PC-3 cell lines), which are tumor cells derived from patients with prostate CA and pancreatic CA, as shown in FIGS. 17A–B and 18A–B, respectively ) were performed. Results of these studies demonstrated consistency with $^{105}$Rh-BBN-37 binding and retention studies using Swiss 3T3 cells. Specifically, the binding affinity of Rh-BBN-37 was high (i.e., IC$_{50}$≅7 nM) with both human cancer cell lines as shown in Table 1. In addition, in all cells, the majority of the $^{105}$Rh-BBN-37 was internalized and perhaps a major unexpected result was that the retention of the $^{105}$Rh-tracer inside of the cells was significantly better than retention in Swiss 3T3 cells as shown in FIGS. 17 and 18. For example, it is particularly remarkable that the percentage of $^{105}$Rh-BBN-37 that remained associated with both the CFPAC-1 and PC-3 cell line was >80% at two hours after removing the extracellular activity by washing with fresh incubation buffer (see FIGS. 17 and 18).

EXAMPLE 4
In Vivo Studies

Biodistribution studies were performed by intravenous (I.V.) injection of either $^{105}$Rh-BBN-22 or $^{105}$Rh-BBN-37 into normal mice. In these studies, unanesthetized CF-1 mice (15–22g, body wt.) were injected I.V. via the tail vein with between one (1) to five (5) uCi (37–185 KBq) of the $^{105}$Rh- labeled agent. Organs, body fluids and tissues were excised from animals sacrificed at 30, 60 and 120 minutes post-injection (PI). The tissues were weighed, washed in saline (when appropriate) and counted in a NaI well counter. These data were then used to determine the percent injected dose (% ID) in an organ or fluid and the %ID per gram. The whole blood volume of each animal was estimated to be 6.5 percent of the body weight. Results of these studies are summarized in Tables 2 and 3.

Results from these studies showed that both the $^{105}$Rh-BBN-22 and $^{105}$Rh-BBN-37 were cleared from the blood stream, predominantly via the kidney into the urine. Specifically, 68.4±6.6% and 62.3±5.8% of the ID was found in urine at two hours Pi of $^{105}$Rh-BBN-22 and $^{105}$Rh-BBN-37, respectively (see Tables 2 and 3). An unexpected finding was that the % ID of $^{105}$Rh that remained deposited in the kidneys of these animals was only 2.4±0.6% ID and 4.6±1.3% ID at two hours Pl of $^{105}$Rh-BBN-22 and $^{105}$Rh-BBN-37 (see Tables 2 and 3). This is much less than would be expected from previously reported data where radiometallated peptides and small proteins have exhibited renal retention of the radiometal that is>10% ID and usually much>10% [Duncan et al., 1997]. The reason for reduced renal retention of $^{105}$Rh-BBN analogues is not known, however, this result demonstrates a substantial improvement over existing radiometallated peptides.

Biodistribution studies also demonstrated another important in vivo property of these radiometallated BBN analogues. Both $^{105}$Rh-BBN-22 and $^{105}$Rh-BBN-37 are efficiently cleared from organs and tissues that do not express GRP receptors (or those that do not have their GRP-receptors accessible to circulating blood). The biodistribution studies in mice demonstrated specific uptake of $^{105}$Rh-BBN-22 and $^{105}$Rh-BBN-37 in the pancreas while other non-excretory organs or tissues (i.e., heart, brain, lung, musde, spleen) exhibited little or no uptake or retention (Tables 2 and 3). Both $^{105}$Rh-BBN-22 and $^{105}$Rh-BBN-37 were removed from the blood stream by both the liver and kidneys with a large fraction of the $^{105}$Rh removed by these routes being excreted into the intestines and the bladder, respectively. It is important to note that the % ID/gm in the pancreas of $^{105}$Rh-BBN-22 and $^{105}$Rh-BBN-37 was 3.9±1.3% and 9.9±5.4%, respectively at 2 hour, PI. Thus, the ratios of % ID/gm of $^{105}$Rh-BBN-22 in the pancreas relative to muscle and blood were 16.2 and 7.6, respectively. The ratios of % ID/gm of $^{105}$Rh-BBN-37 in the pancreas relative to muscle and blood were 25.4 and 29.1, respectively. These data demonstrated selective in vivo targeting of these radiometallated BBN analogues to cells expressing GRP receptors [Zhu et al., 1991; Qin et al., 1994] and efficient clearance from non-target tissues. If cancer cells that express GRP receptors are present in the body, these results indicate radiometallated BBN analogues will be able to target them with a selectivity similar to the pancreatic cells.

A comparison of the pancreatic uptake and retention of [105]Rh-BBN-22 with [105]Rh-BBN-37 demonstrated that [105]Rh-BBN-37 deposits in the pancreas with a 2-fold better efficiency than [105]Rh-BBN-22 (i.e., 3.6±1.2% ID and 2.3±1.0% ID) for [105]Rh-BBN-37 at one and two hours PI, respectively, vs. 1.2±0.5% ID and 1.0±0.1% ID for [105]Rh-BBN-22 at one and two hours PI). This data is consistent with the >2-fold higher uptake and retention of [105]Rh-BBN-37 found in the in vitro studies shown in FIG. 16.

EXAMPLE 5

Figure 19:
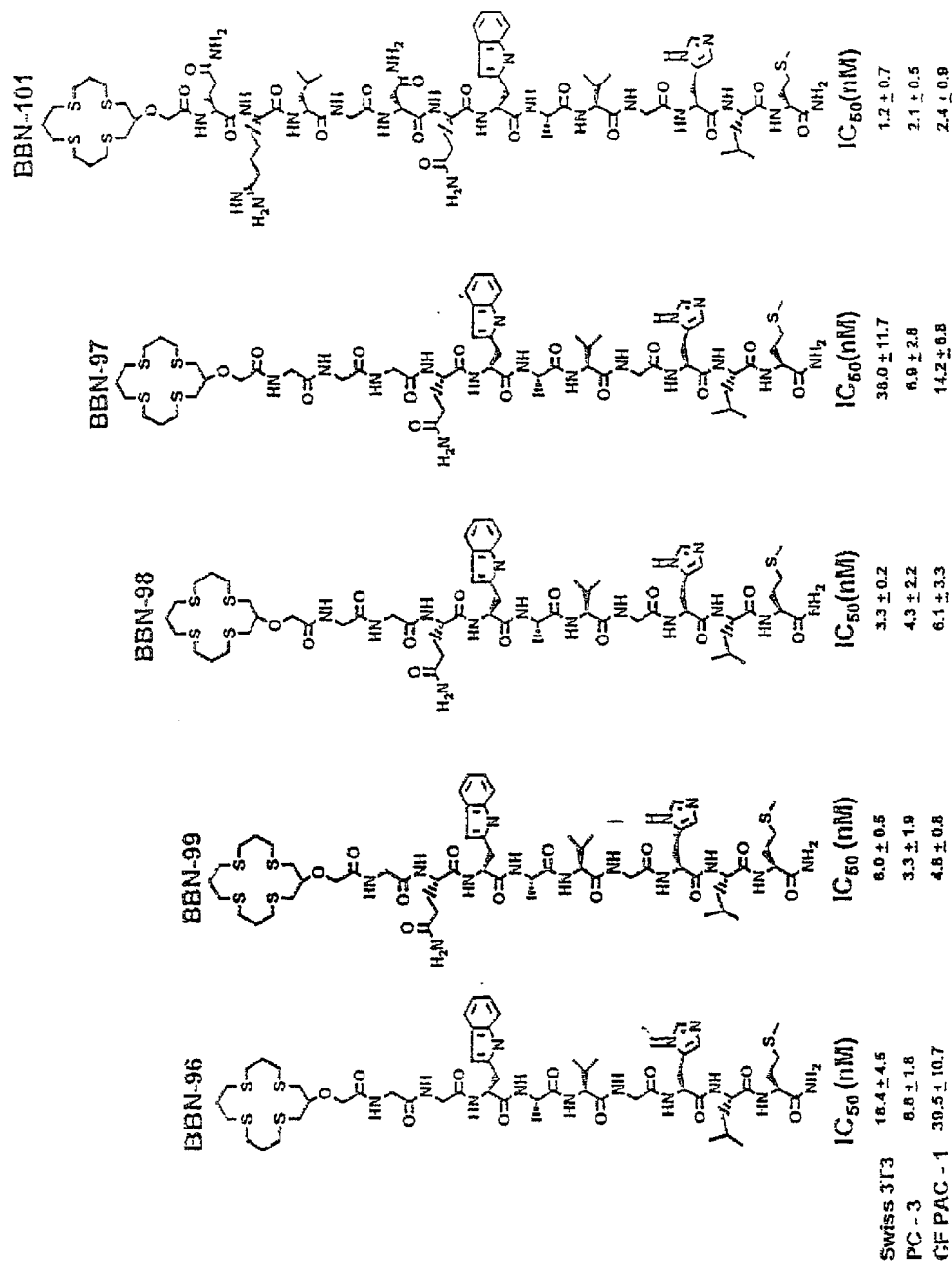
FIG. 19 illustrates 5 [16]aneS$_4$ bombesin analogues which utilize amino acids as Linking Groups.

Synthesis and in vitro binding measurement of synthetic BBN conjugate analogues employing amino acid chain spacers A. Synthesis Five BBN analogues were synthesized by SPPS in which between 2 to 6 amino acid spacer groups were inserted to separate a $S_4$-macrocyclic chelator from the N-terminal trp$^8$ on BBN(8–14) (FIG. 19). Each peptide was prepared by SPPS using an Applied Biosystems Model 432A peptide synthesizer. After cleavage of each BBN analogue from the resin using Trifluoracetic acid (TFA), the peptides were purified by $C_{18}$ reversed-phase HPLC using a Vydac HS54 column and $CH_3CN/H_2O$ containing 0.1% TFA as the mobile phase. After collection of the fraction containing the desired BBN pepfide, the solvent was evaporated. The identity of each BBN peptide was confirmed by FAB-mass spectrometry (Department of Chemistry - Washington University, St. Louis, Mo.).

Various amino acid sequences (in some cases containing different R group moieties) were conjugated to the N-terminal end of the BBN binding region (i.e., to BBN-8 or Trp$^8$). BBN analogue numbers 96, 97, 98, 99 and 101 were synthesized as examples of N-terminal modified peptides in which the [1 6]aneS$_4$ macrocycle BFCA was separated from trp$^8$ on BBN(8–14) by various amino acid sequences as shown in FIG. 19.

The [16]aneS$_4$ macrocyclic ligand was conjugated to selected tethered BBN analogues. The —OCH$_2$COOH group on the [16] and S$_4$ macrocycle derivative was activated via HOBt/HBTU so that it efficiently formed an amide bond with the terminal NH$_2$ group on the spacer side arm (following deprotection). The corresponding [16]aneS$_4$ tethered BBN derivatives were produced and examples of 5 of these derivatives (i.e., BBN-96, 97, 98, 99 and 101) are shown in FIG. 19. As previously described, each [16]aneS$_4$ BBN.derivative was purified by reversed phase HPLC and characterized by FAB Mass Spectroscopy.

B. In Vitro Binding Affinities

The binding affinities of the synthetic BBN derivatives were assessed for GRP receptors on Swiss 3T3 cells, PC-3 cells and CF PAC-1 cells. The IC$_{50}$'s of each of derivative were determined relative to (i.e., in competition with) $^{125}$I-Tyr$^4$-BBN. The cell binding assay methods used to measure the IC$_{50}$'s is standard and was used by techniques previously reported [Jensen et al., 1993; Cai et al., 1992; Cai et al., 1994]. The methods used for determining IC$_{50}$'s with all BBN analogue binding to GRP receptors present on all three cell lines were similar. The specific method used to measure IC$_{50}$'s on Swiss 3T3 cells is briefly described as follows:

Swiss 3T3 mouse fibroblasts are grown to confluence in 48 well microliter plates. An incubation media was prepared consisting of HEPES (11.916gA), NaCl (7.598 g/l), KCI (0.574 g/l), MgCl$_2$(1.106 g/l), EGTA (0.380 g/l), BSA (5.0 g/l), chymostatin (0.002 g/l), soybean trypsin inhibitor (0.200 g/1), and bacitracin (0.050 g/1). The growth media was removed, the cells were washed twice with incubation media, and incubation media was returned to the cells. $^{125}$I-Tyr$^4$-BBN (0.01 uCi) was added to each well in the presence of increasing concentrations of the appropriate competitive peptide. Typical concentrations of displacing peptide ranged from $10^{-12}$ to $10^{-5}$ moles of displacing ligand per well. The cells were incubated at 37° C for forty minutes in a 95% O$_2$/5% CO$_2$ humidified environment. At forty minutes post initiation of the incubation, the medium was discarded, and the cells were washed twice with cold incubation media. The cells were harvested from the wells following incubation in a trypsin/EDTA solution for five minutes at 37° C. Subsequently, the radioactivity, per well, was determined and the maximum % total uptake of the radiolabeled peptide was determined and normalized to 100%. A similar procedure was used in performing cell binding assays with both the PC-3 and CF$_a$-PAC-1 human cancer cell lines.

C. Results of Binding Affinity Measurements

The IC$_{50}$ values measured for the BBN derivatives synthesized in accordance with this invention showed that appending a chelator via amino acid chain spacer groups via the N-terminal BBN-8 residue (i.e., Trp$^8$) produced a variation of IC$_{50}$ values. For example, see IC$_{50}$ values shown for BBN 96, 97, 98 and 101 in FIG. 19. The observations are consistent with previous reports showing variable IC$_{50}$ values when derivatizing BBN(8–13) with a predominantly short chain of amino acid residues [Hoffken, 1994]. When the amino acid spacer groups used in BBN-98, 99 and 101 were appended between BBN(7–14) and the [16]aneS$_4$ macrocyle, the IC$_{50}$'s were found to be surprisingly constant and in the 1–6 nM range for all three cell lines (i.e., see IC$_{50}$ values shown in FIG. 19). These data suggest that using relatively simple spacer groups composed entirely of selected amino acid sequences to extend ligands some distance from the BBN region (e.g., BBN(8–14) can produce derivatives that maintain binding affinities in the 1–6 nmolar range.

D. Cell Binding Studies with Rh-BBN-Coniugates

Figure 20:
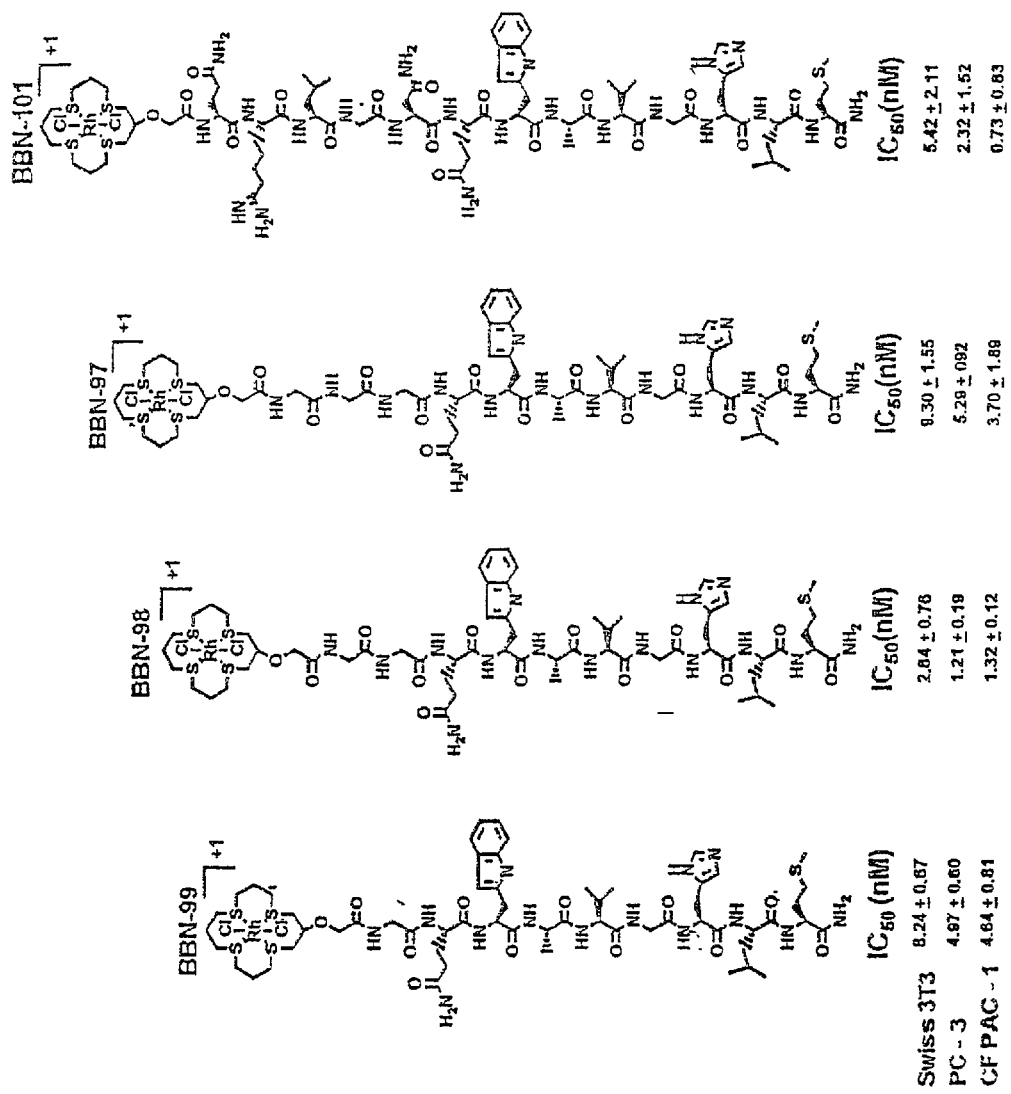
FIG. 20 illustrates 4 Rhodium-[16]aneS$_4$ bombesin analogues and IC$_{50}$ values obtained in 3 cell lines.

Results illustrated in FIG. 20 show that when the corresponding RhCl$_2$ [16]aneS$_4$ complex was separated from Trpa on BBN(8–14) by the four different amino acid spacer groups (see FIG. 20), the IC$_{50}$'s of all four analogues (i.e., BBN-97, -98, -99, -101) were between 0.73 and 5.29 nmolar with GRP receptors on the PC-3 and CF PAC-1 cell lines. The IC$_{50}$'s for these same Rh-BBN conjugates were somewhat higher with the Swiss 3T3 cell line (FIG. 20). These data demonstrate that amino acid chain with spacer groups used to move the +1 charged Rh-S$_4$-chelate away from the BBN binding region will result in a metallated BBN analogue with sufficiently high binding affinities to GRP receptors for in vivo tumor targeting applications.

EXAMPLE 6

Figure 21:
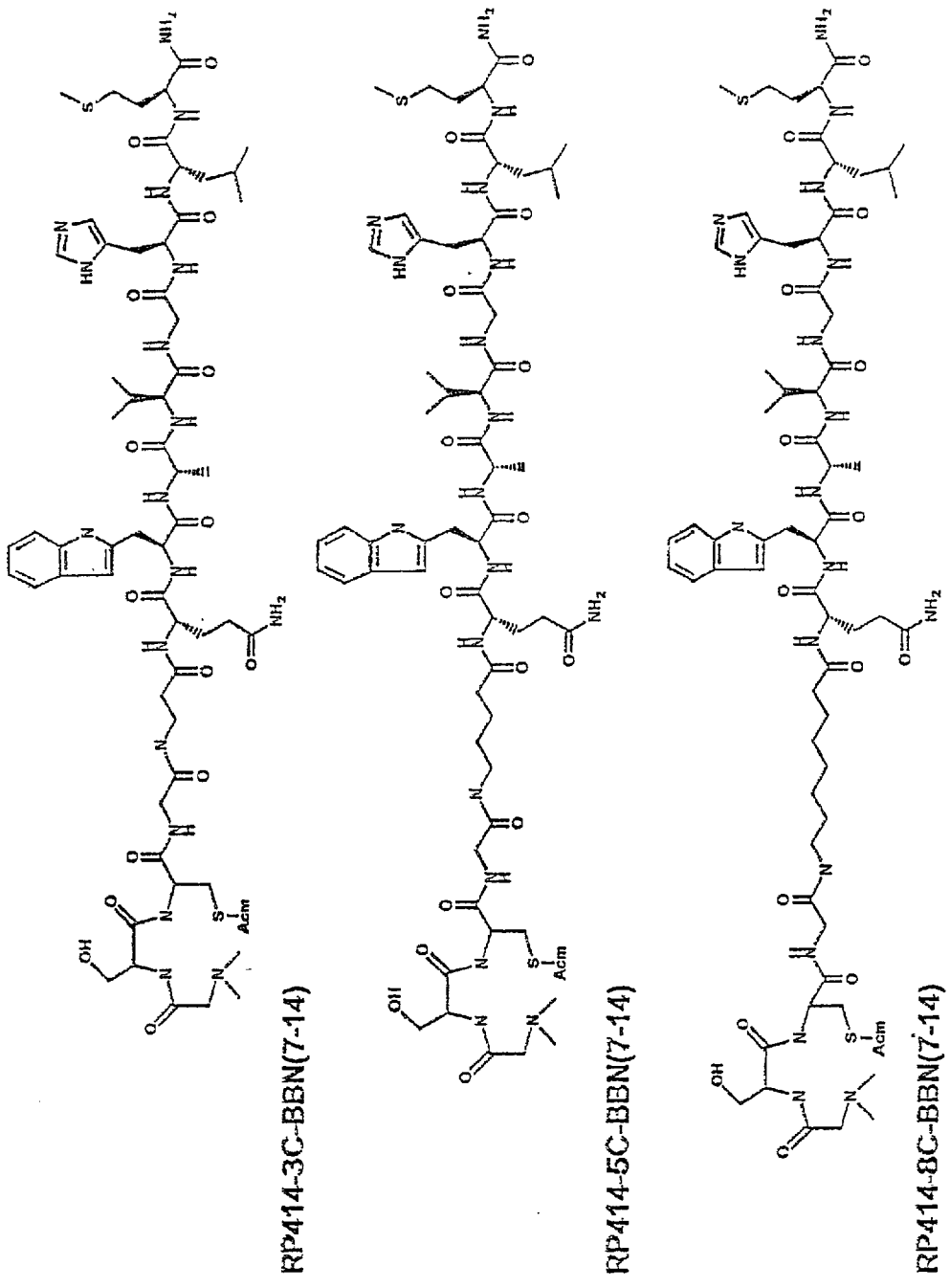
FIG. 21 illustrates 3 different N$_3$S-BFCA conjugates of BBN(7–14)

Synthesis and in vitro binding assessment of a $^{99m}$Tc-labeled synthetic BBN analogue A. Synthesis Several tetradentate chelating frameworks have been used to form stable $^{99m}$Tc or 188Re labeled peptide and protein conjugates [Eckelman, 1995; Li et al., 1996b; Parker, 1990; Lister-James et al., 1997]. Many of these ligand systems contain at least one thiol (-SH) donor group to maximize rates of formation and stability (both in vitro and in vivo) of the resultant Tc(V) or Re(V) complexes [Parker, 1990; Eckelman, 1995]. Results from a recent report indicates that the bifunctional chelating agent (BFCA) (dimethylglycyl-L-seryl-L-cyteinyl-glycinamide (N3S-BFCA) is capable of forming a well-defined complex with ReO+3 and TcO+3 [Wong et al., 1997]. Since this ligand framework can be synthesized by SPPS techniques, this N3S-BFCA was selected for use in forming of Tc-99m-BBN-analogue conjugates. Three different N3S-BFCA conjugates of BBN (7–14) were synthesized (BBN-120,-121 and (122) as shown in FIG. 21 by SPPS. BBN-120, BBN-121 and BBN-122 represent a series of analogues where the N3S-BFCA is separated from the BBN(7–14) sequence by a 3, 5 and 8 carbon spacer groups (FIG. 21). Each peptide was synthesized and purified using the SPPS and chromatographic procedures outlined in Example 1. The thiol group on cysteine was protected using the ACM group, which is not cleaved during cleavage of these BBN-conjugates from the resin using TFA. The identity of BBN-120, -121 and -122 was confirmed by FAB mass spectrometry. Synthesis and purification of the N3S-BFCA could also be readily accomplished using SPPS methods, followed by HPLC purification (see Example 1). The ACM group was used to protect the thiol group on cysteine during synthesis and cleavage from the resin.

B. In Vitro Binding Affinities

Figure 22:
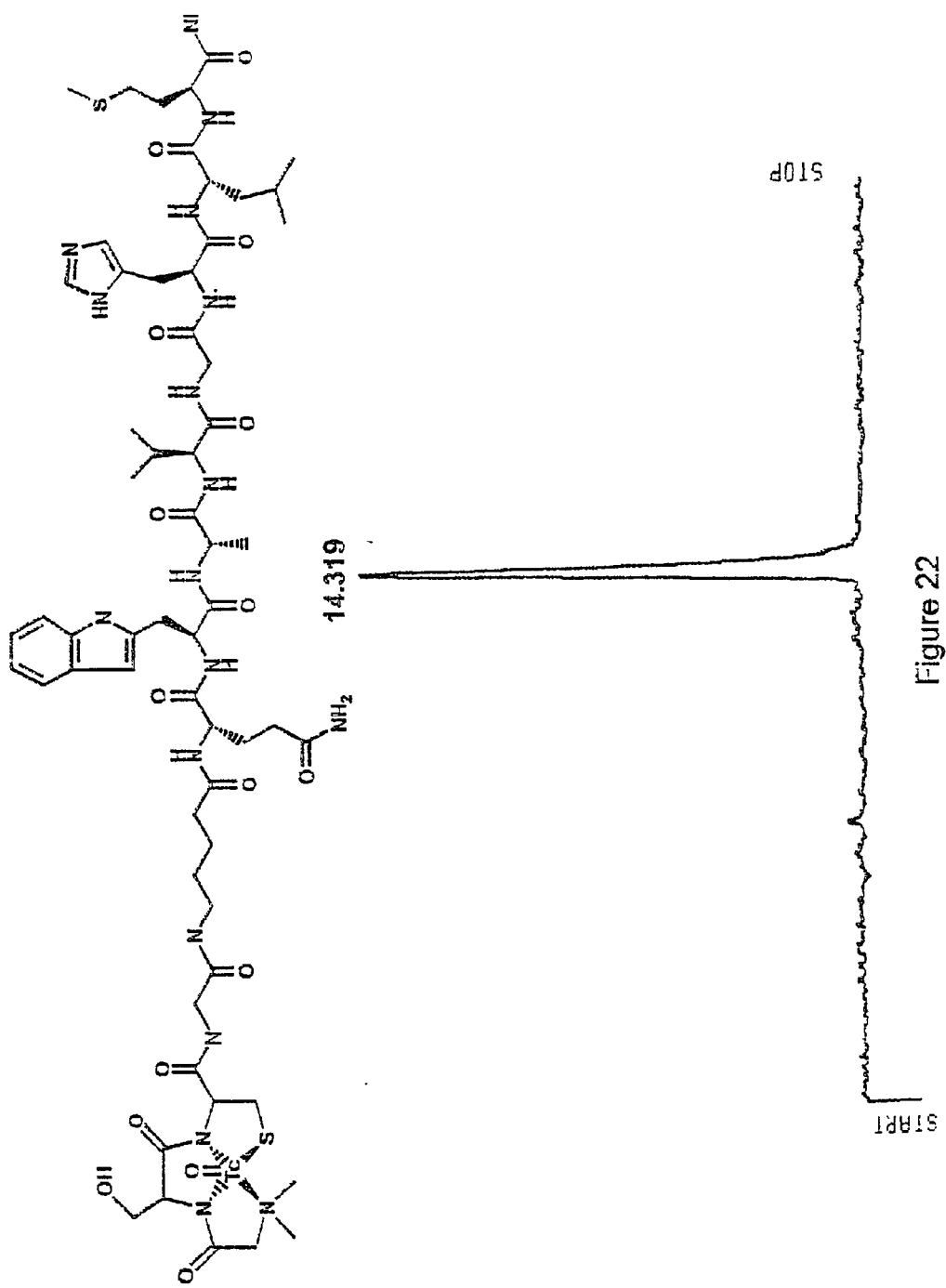
FIG. 22 illustrates on HPLC chromatogram of $^{9m}$Tc-BBN-122.

Synthesis of $^{99m}$Tc-BBN-122 (FIG. 22) was prepared by two methods [i.e., (1) by transchelation of $^{99m}$TcO+3 from $^{99m}$Tc-gluconate or (2) by formation of the "preformed" 99mTc-BFCA complex followed by —COOH activation with tetrafluorophenyl and subsequent reaction with the C5-carbon spacer group appended to BBN[7–14)). In both cases, the 99mTc-labeled peptide formed is shown in FIG. 22. The structure of this Tc-BBN-122 conjugate was determined by using non-radioactive Re(the chemical congener of Tc). In these studies, the "preformed" ReO+3 complex with the N3S-BFCA was prepared by reduction of ReO4; with SnCl2 in the presence of excess N3S-BFCA dissolved in sodium phosphate buffered water at pH 6–6.5 by a method previously published [Wong et al., 1997]. After purification of the ReO-N3S-BFCA complex, the structure of this chelate was shown (by Mass-Spect) to be identical to that previously reported [Wong et al., 1997].

The ReO-N3-S-BFCA complex was converted to the activated trifluorophenyl (TFP) ester by adding 10 mg of the complex to 6 mg (dry) EDC and the 50 ul of TFP. After the solution was vortexed for one minute, CH3CN was added until disappearance of cloudiness. The solution was incubated for one hour at RT and purified by reversed-phase HPLC. To prepare the ReO-N3S-BFCA complex BBN-122 conjugate (FIG. 22), one [l of the HPLC fraction containing the ReO-N3S-BFCA complex was added to a solution containing 1 mg of the C8-tethered BBN[7–14) peptide in 0.2 N NaHCO3 at pH 9.0. After incubation of this solution for one hour at RT, the sample was analyzed and purified by reversed-phase HPLC. The yield of Re-BBN-1 22 was approximately 30–35%.

The method for preparation of the corresponding $^{99m}$Tc-BBN-122 conjugate, using the "preformed" 99mTcO-N3S-BFCA complex, was the same as described above with the "preformed" ReO-N3S-BFCA complex. In this case, 99mTcO4, from a 99Mo/99mTc generator, was reduced with an aqueous saturated stan nous tartrate solution in the presence of excess N3S-BFCA. The yields of the $^{99m}$Tc-BBN-122 product using this "preformed" method were approximately 30–40%. Reversed phase HPLC analysis of the $^{99m}$Tc-BBN-122, using the same gradient elution program[1] as used for analysis of the Re-BBN-122 conjugate, showed that both the 99mTc-BBN-122 and 188Re-BBN-122 had the same retention time (i.e., 14.2–14.4 min) (See FIG. 22). This provides strong evidence that the structure of both the 99mTc-BBN-122 and Re-BBN-122 are identical.

The binding affinities of BBN-122 and Re-BBN-122 were assessed for GRP receptors on Swiss 3T3 cells, PC-3 cells and CFPAC-1 cells that express GRP receptors. The IC50's of each derivative were determined relative to (i.e., in competition wit[4 1251-Tyr4-BBN (the Kd for 1251-Tyr4-BBN for GRP receptors in Swiss 3T3 cells is reported to be 1.6+0.4nM) [Zhu et al., 1991]. The cell binding assay methods used to measure the $lC_{50}$'s is standard and was used by techniques previously reported [Leban et al., 1994; Cai et al., 1994; Cai et al., 1992]. The methods used for determining $IC_{50}$'s with all GRP receptor binding of GRP receptors on all cell lines was similar and has been described previously for the other BBN-analogues and Rh-BBN analogues described in this document.

C. Results of Binding Affinity Measurements

The $IC_{50}$ values measured for BBN-122 and Re-BBN-122 synthesized in accordance with this invention showed that appending an 8-carbon hydrocarbon chain spacer linked to the N3S1-BFCA and the corresponding Re complex (i.e., Trp8) produced BBN conjugates with $IC_{50}$ values in a 1–5 nmolar range (See Table A). When 99mTc-BBN-122 was incubated with these same cells, it was shown that >nmolar concentrations of BBN displaced this $^{99m}$Tc conjugate by >90%. This result demonstrates that 99mTc-BBN-122 has high and specific binding affinity for GRP receptors. These data suggest that using relatively simple spacer groups to extend the N3S ligand framework and the corresponding Tc-or Re-N3S1, complexes some distance from the BBN binding region can produce derivatives that maintain binding affinities in the 1–5 nmolar range. TABLE A.

Summary of $IC_{50}$ values for GRP receptor binding for the non-metallated BBN-1 22 conjugate or the Re-BBN-1 22 conjugate in two cell lines (PC-3 and CF-PAC-1 cell lines that express GRP receptors). The $IC_{50}$ values were measured using cell binding assays relative to 1251-Tyr4-BBN.

[1]Gradient elution program used in these studies was as follows.
Flow 1.5 ml/minute
Solvent A = HO with 0.1% TFA
Solvent B = CHCN with 0.1% TFA

| Time (minutes) | % A/% B |
|---|---|
| 0 | 95/5 |
| 25 | 30/70 |
| 35 | 95/5 |

| | IC50 (nmolar) | |
|---|---|---|
| Conjugate | PC-3 | CF-PAC1 |
| BBN-122 | 3.59 ± 0.75 (n = 6) | 5.58 ± 1.92 (n = 14) |
| Re-BBN-122 | 1.23 ± 0.56 (n = 12) | 1.47 ± 0.11 (n = 6) |

EXAMPLE 7

Retention of 99mTc-BBN-122 in Human Cancer Cells PC-3 and CF-PAC-1 cells)

Once the radiometal has been specifically "delivered" to cancer cells (e.g., employing the BBN binding moiety that specifically targets GRP receptors on the cell surface), it is necessary that a large percentage of the "delivered" radioactive atoms remain associated with the cells for a period time of hours or longer to make an effective radiopharmaceutical for effectively treating cancer. One way to achieve this association is to internalize the radiolabeled BBN conjugates within the cancer cell after binding to cell surface GRP receptors.

Experiments designed to determine the fraction 99mTc-BBN-122 internalized within cells were performed by the same method previously described for 105Rh-BBN-37. Briefly, excess 99mTc-BBN-122 was added to PC-3 or CFPAC-1 cell incubation media and allowed to establish equilibrium after a forty minute incubation. The media surrounding the cells was removed and the cells were washed with fresh media containing no radioactivity. After washing, the quantity of radioactivity associated with the cells was determined (i.e., total counts per minute $^{99m}$Tc associated with cells). The PC-3 and CFPAC-1 cells were then incubated in a 0.2M acetic acid solution (pH2.5) which caused the surface proteins (including GRP receptors) to denature and release all surface bound radioactive materials. After removing this buffer and washing, the cells were counted again. The counts per minute (c.p.m.) associated with the cells at that point were only related to the $^{99m}$Tc that remained trapped inside of the PC-3 or CFPAC-1 cells.

To determine intracellular retention of 99mTc activity, a similar method was employed. However, after washing the cells with fresh (non-radioactive) incubation media, the cells were incubated in the fresh media at different time period after washing away all extracellular 99mTc-BBN-122. After each time interval, the methods used to determine total c.p.m. and intracellular c.p.m. by washing with a 0.2M acetic acid solution at pH 2.5.

Figure 23:
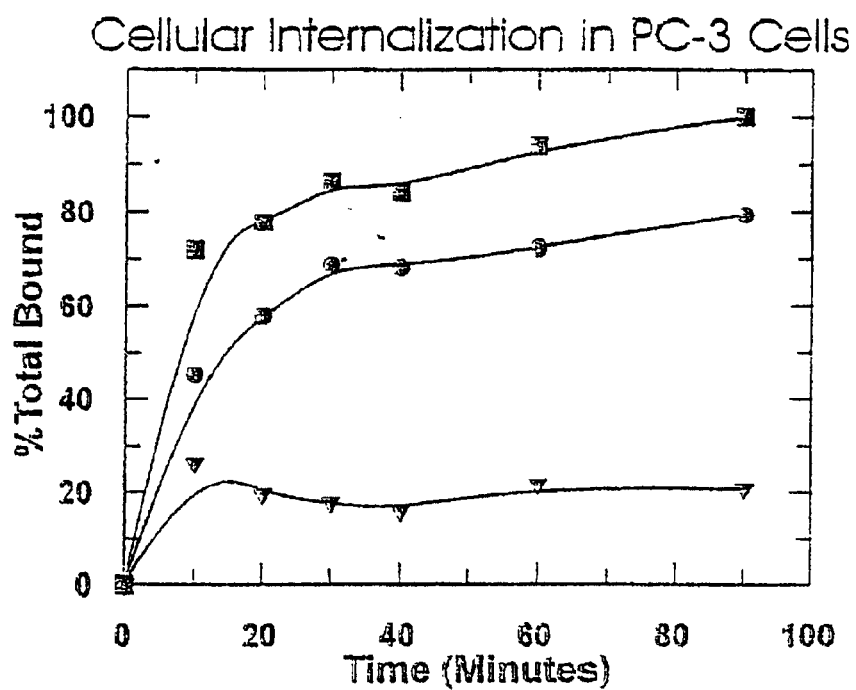
FIG. 23 is a graph illustrating $^{99m}TC$-BBN-122 internalization into human prostate cancer cells (PC-3 cells)
Figure 24:
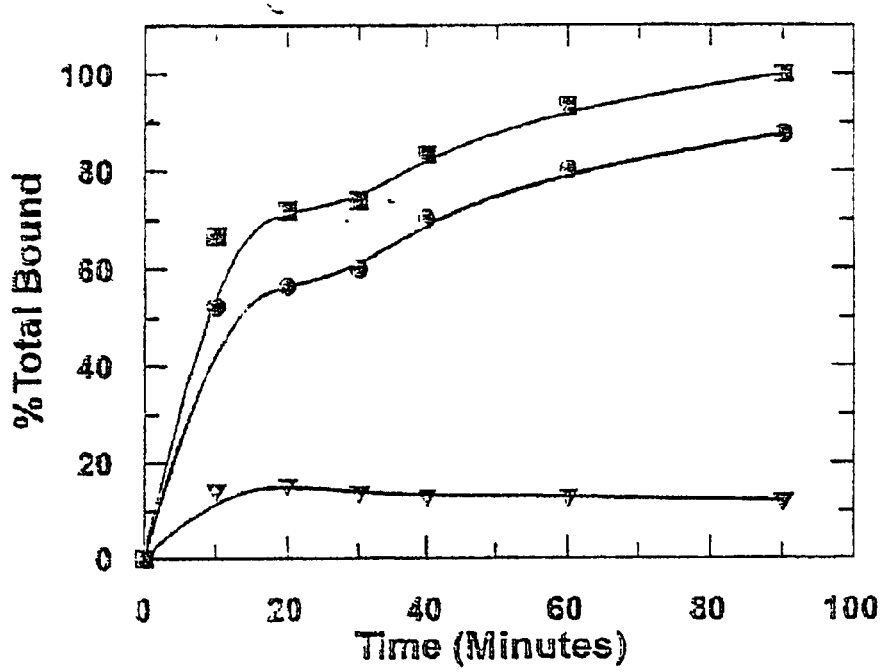
FIG. 24 is a graph illustrating $^{99m}Tc$-BBN-122 internalization into human pancreatic tumor cells (CFPAC-1 cells)
Figure 25:
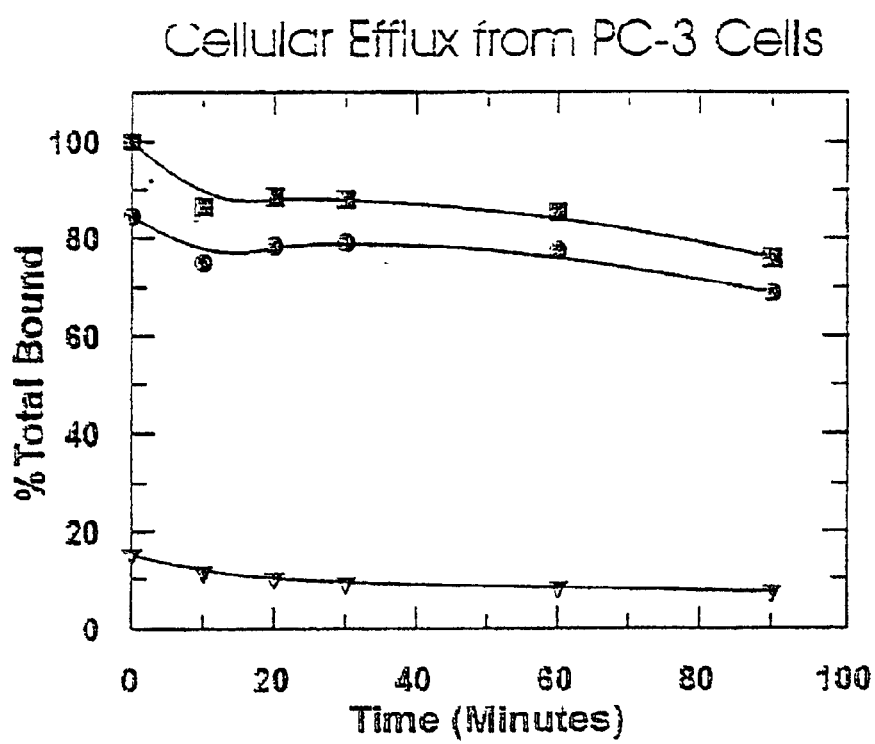
FIG. 25 is a graph illustrating $^{99m}Tc$-RP-414-BBN-42 retention in PC-3 prostate cancer cells.
Figure 26:
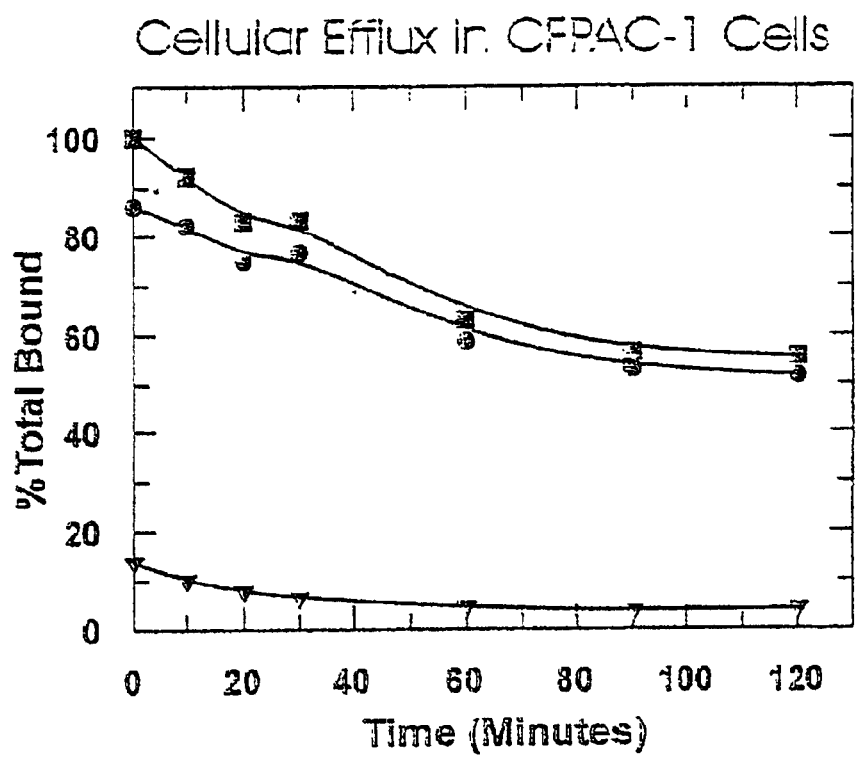
FIG. 26 is a graph illustrating $^{99m}Tc$-42 retention in CFPAC-1 pancreatic cancer cells.

Studies with the 99mTc-BBN-122 agonist show that it is internalized inside of the PC-3 and CFPAC-1 cells (FIGS. 23–26) and that substantial intracellular retention of 99mTc by the GRP receptor expressing cells occurs. For example, results of studies using 99mTc-BBN-122 in conjunction with PC-3 cells showed a high rate of internalization (FIG. 23) and that approximately 75% of the 99mTc activity remains associated with the cells at ninety minutes post-washing (FIG. 25). Almost all of this 99mTc cell-associated activity is inside of the PC-3 cells. Similar results were also found with the CFPAC 1 cells where there is also a high rate of 99mTc-BBN-122 internalization (FIG. 24) and relatively slow efflux of 99mTc from the cells (i.e., 50–60% retention at 120 minutes post-washing (FIG. 26).

The 99mTc-BBN-122 peptide conjugate shown in FIG. 22 has an amidated methionine at position BBN-14 and is expected to be an agonist [Jensen et al., 1993]. Therefore, it would be predicted to rapidly internalize after binding to GRP receptors on the cell surface [Bjisterbosch et al., 1995; Smythe et al., 1991], which is confirmed by applicants' data in FIGS. 23–26.

EXAMPLE 8
In Vivo Studies

Biodistribution studies were performed by intravenous (I.V.) injection of 99mTc-BBN-122 into normal mice. In these studies, unanesthetized CF-i mice (15–22g, body wt.) were injected I.V. via the tail vein with between one (1) to five (5) uCi (37–185 KBq) of 99mTc-BBN-122. Organs, body fluids and tissues were excised from animals sacrificed at 0.5, 1, 4 and 24 hours post-injection (PI). The tissues were weighed, washed in saline (when appropriate) and counted in a NaI well counter. These data were then used to determine the percent injected dose (% ID) in an organ or fluid and the % ID per gram. The whole blood volume of each animal was estimated to be 6.5 percent of the body weight. Results of these studies are summarized in Tables B and C.

Results from these studies showed that 99mTc-BBN-122 is cleared from the blood stream predominantly via the hepatobiliary pathway showing about 35% of the 99mTc-activity cleared via the kidney into the urine. Specifically, 33.79+1.76% of the ID was found in urine at one hour PI (Table B). The retention of 99mTc activity in the kidneys and liver is very low (Table B). This is much less than would be expected from previously reported data where radiometallated peptides and small proteins have exhibited renal retention of the radiometal that is >10% ID and usually much >10% [Duncan et al., 1997]. The reason for reduced renal retention of 99mTc-BBN-122 is not known, however, this result demonstrates a substantial improvement over existing radiometallated peptides.

Biodistribution studies also demonstrated another important in vivo property of 99mTc-BBN-122 in that it is efficiently cleared from organs and tissues that do not express GRP receptors (or those that do not have their GRP-receptors accessible to circulating blood). The biodistribution studies in mice demonstrated specific uptake of 99mTc-BBN-122 in the pancreas while other non-excretory organs or tissues (i.e., heart, brain, lung, muscle, spleen) exhibited little or no uptake or retention. 99mTc-BBN-122 is removed from the blood stream by both the liver and kidneys with a large fraction of the 99mTc removed by these routes being excreted into the intestines and the bladder, respectively. It is important to note that the % ID/gm in the pancreas of 99mTc-BBN-122 is 12.63%/gm at 1 hour and drops to only 5.05% at the 4 hour PI (Table C). Thus, the ratios of % ID/gm of 99mTc-BBU-122 in the pancreas relative to muscle and blood were 92.2 and 14.78 at 4 hour PI, respectively. These data demonstrated selective in vivo targeting of this 99mTc-labeled BBN analogue to cells expressing GRP receptors [Zhu et al., 1991; Qin et al., 1 994] and efficient clearance from non-target tissues. If cancer cells that express GRP receptors are present in the body, these results indicate 99mTc-BBN analogues will be able to target them with a selectivity similar to the pancreatic cells.

EXAMPLE 9
Materials and Methods For Examples 9 and 10

The following abbreviations are used in the examples and derived from the following amino acids:
ava=5-amino valeric acid
aoc=8-amino octanoic acid
aun=11-amino undecanoic acid Reagents and Apparatus. All chemicals were obtained from either Aldrich Chemicals (St. Louis, Mo.) or Fisher Scientific (Pittsburgh, Pa.). All chemicals and solvents used in these studies were reagent grade and used without further purification. The Resin and fmoc-protected amino acids were purchased from Calbiochem-Novabiochern Corp (San Diego, Calif.) and the other peptide reagents from Applied Biosystems, Inc (Foster City, Calif.). The DOTA-tris(t-butyl ester) was purchased from Macrocyclics (Dallas, Tex.) and the fmoc-protected w-amino alkyl carboxylic acids from Advanced ChemTech (Louisville, Ky.). 1251-Tyr4-Bombesin (1251-Tyr4-BBN) was obtained from NEN Life Sciences Products, Inc (Boston, Mass.). 111 InC 3 was obtained from Mallinckrodt Medical, Inc (St. Louis, Mo.) as a 0.05N HCl solution. 90Y was obtained from Perkin-Elmer (Biclerica, Mass.) as an HCl solution. Electrospray mass spectral analyses were performed by Synpep Corporation and T47D (Dublin, Calif.). Human prostate cancer PC-3 cells and MDA-MB-231 breast cancer cells were obtained from American Tissue Culture Collection (ATCC) and maintained and grown in the University of Missouri Cell and Immunology Core facilities. CF-i mice were purchased from Charles River Laboratories (Wilmington, Mass.) and maintained in an in house animal facility.

Solid Phase Peptide Synthesis (SPPS). Peptide synthesis was carried out on a Perkin Elmer—Applied Biosystems Model 432 automated peptide synthesizer employing traditional fmoc chemistry with HBTU activation of carboxyl groups on the reactant with the N-terminal amino group on the growing peptide anchored via the C-terminus to the resin. Rink Amide MBHA resin (25 μmol), fmoc-protected amino acids with appropriate side-chain protections (7 μmol), fmoc-protected amino alkyl carboxylic acids (75 μmol) and DOTA-tris(t-butyl ester) (75 μmol) were used for the synthesis. The final products were cleaved by a standard procedure using a cocktail containing thioanisol, water, ethanedithiol and trifluoroacetic acid in a ratio of 2:1:1:36 and precipitated into methyl-t-butyl ether. Typical yields of the crude peptides were 80–85%. Crude peptides were purified by HPLC and the solvents were removed on a SpeedVac concentrator. The purified peptides were characterized by electrospray mass spectrometry. The mass spectral analysis results are shown in Table 4.

High performance liquid chromatography (HPLC). High performance liquid chromatography (HPLC) analyses for DOTA conjugates were performed on a Waters 600E system equipped with Varian 2550 variable absorption detector, Packard Radiometic 1 50TR flow scintillation analyzer, sodium iodide crystal radiometric detector, Eppendorf TC-50 column temperature controller and Hewlett Packard HP3395 integrators. A Phenomenex Jupiter C-18 (5pm, 300 A0, 4.6×250 mm) column was used with a flow rate of 1.5 ml/minute HPLC solvents consisted of H20 containing 0.1% trifluoroacetic acid (Solvent A) and acetonitrile containing 0.1% trifluoroacetic acid (Solvent B). HPLC gradient conditions for 0 spacer to 8 carbon spacer analogs begin with a solvent composition of 80% A and 20% B followed by a linear gradient to 70% A:30% B over 30 minutes. HPLC gradient conditions for the 11 carbon spacer analysis are solvent composition of 75% A and 25% B followed by a linear gradient to 50% A:50% B over 30 minutes.

Indium metallation. A solution of the unmetallated DOTA-BBN conjugates as shown in table 4 (5.0 mg) in 0.2M tetramethylammonium acetate (0.5 ml) was added to indium trichloride ($InCl_3$) (10.0 mg). The pH of the reaction mixture was adjusted to 5.5 (Scheme 1). The reaction mixture was incubated for 1 hour at 80 OC. The resultant In-DOTA-BBN conjugate (Scheme 1) was purified by reversed-phase HPLC and analyzed by electrospray mass spectrometry. The mass spectral analysis results are shown in Table 4. The pure product was obtained as a white powder with a typical yield of 50–60%.

111Indium/90Yttrium labeling. An aliquot of 111 $InCl_3$ (1.0 mCi, 50 ul) was added to a solution of the unmetallated DOTA-BBN (100 ug) conjugates shown in Table 4 in 0.2M tetramethyiammonium acetate (500 ul). The pH of the reaction mixture was adjusted to 5.6. The reaction mixture was incubated for 1 hour at 80 OC. An aliquot of 0.002M EDTA (50 pl) was added to the reaction mixture to complex the unreacted 111 ln+3. The resultant 111 In-DOTA-BBN conjugate was obtained as a single product and purified by reversed-phase HPLC. The purified 111 In-DOTA-BBN conjugate was then concentrated by passing through a 3M Empore C-18 HD high performance extraction disk (7mm/3ml) cartridge and eluting with 33% ethanol in 0.1 M NaH2PO4 buffer (400 pl). The concentrated fraction was then diluted with 0.1 M NaH2PO4 buffer (2.3 ml, pH-7) to make the final concentration of ethanol in the solution <5%. The 90Y DOTA-BBN complex was similarly prepared.

In Vitro Cell Binding Studies. The $IC_{50}$ of the various In-DOTA-BBN conjugates was determined by a competitive displacement cell binding assay using 125I-Tyr4-BBN. Briefly 3×104 cells suspended in RPMI medium 1640 at pH-7.4 containing 4.8 mg/ml HEP ES, 0.1 ug/ml Bacitracin and 2 mg/ml BSA, were incubated at 37 OC and a 5% CO2 atmosphere for 40 minutes in the presence of 20,000 cpm 1251-Tyr4-BBN and increasing concentration of the In-DOTA-BBN conjugates. After the incubation, the reaction medium was aspirated and cells were washed four times with media. The radioactivity bound to the cells was counted in a Packard Riastar gamma counting system. The % 125I-Tyr4-BBN bound to cells was plotted vs. increasing concentrations of In-DOTA-BBN conjugates to determine the respective $IC_{50}$ values.

Internalization and efflux studies. In vitro studies to determine the degree of internalization of the 111 In-DOTA-8-Aoc-BBN[7-14]NH2 conjugate were carried out by a method similar to that of described by Rogers, et al. These studies were performed by incubating 3 X 1 04 cells suspended in RPM I medium 1640 at pH-7.4 containing 4.8 mg/ml HEPES, 0.1 ug/mi Bacitracin and 2 mg/ml BSA, at 37 OC and a 5% C02 atmosphere for 40 minutes in presence of 20,000 cpm 111 In-DOTA-8-Aoc-BBN[7-14]NH2 conjugate. After the incubation, the reaction medium was aspirated and cells were washed with media. The percent of cell-associated activity as a function of time (in the incubating medium at 37 OC) was determined. The percentage radioactivity trapped in the cells was determined after removing activity bound to the surface of the cells by washing with a pH-2.5 (0.2M acetic acid and 0.5M NaCI) buffer 1, 2, 3 and 4 hours afterwards.

In vivo pharmacokinetic studies in CF-I mice. The biodistribution and uptake of 111 In-DOTA-BBN conjugates in CF-i mice was studied. The mice (average weight, 25 g) were injected with aliquots (50–100 p 1) of the labeled peptide solution (55–75 kBq) in each animal via the tail vein. Tissues and organs were excised from the animals sacrificed at 1 hour post-injection. The activity counted in a Nal counter and the percent injected dose per organ and the percent injected dose per gram were calculated. The percent injected dose (% ID) in the blood was estimated assuming a blood volume equal to 6.5% of the total body weight. Receptor blocking studies were also carried out where excess (100 ug) BBN was administered to animals along with the 111 In-DOTA-8-Aoc-BBN[7–14]NH2.

In vivo pharmacokinetic studies in human tumor bearing SCID mice. The biodistribution studies of the 111n and 90Y conjugates were determined in SCID mice bearing human tumor xenografts of either PC-3 (human androgen independent prostate cancer cell origin) or MDA-MB-231 (human breast cancer cell origin) cell lines. The xenograft models were produced by bilateral flank inoculation of 5×106 cells (PC-3 or MDA-MB-231 cells) per site. Four to six weeks post inoculation, palpable tumors were observed. At this point, the mice were injected with 4pCi of the complex in 100/uL of isotonic saline via the tail vein. The mice were euthanized and tissues and organs were excised from the animals at selected times post-injection (p.i.), including 15 minutes, 30 minutes, 1 hour, 4 hours, 24 hours, 48 hours, and 72 hours p.i. Subsequently, the tissues and organs were weighed and counted in a Nal well counter and the percent injected dose (%ID) and %ID/g of each organ or tissue calculated. The % ID in whole blood was estimated assuming a whole-blood volume of 6.5% the total body weight.

In vivo pre-clinical evaluation of single dose radiotherapy in human tumor bearing SCID mice. Preclinical therapeutic evaluation of the 90Y-DOTA-8-Aoc-BBN[7-145NH2 conjugate was performed in SCID mice bearing PC-3 human androgen independent prostate cancer cell human tumor xenografts. The xenograft model was produced by bilateral flank inoculation of 5×106 PC-3 cells per site. Twenty one days post inoculation when palpable tumors appeared, single dose administration of 90Y-DOTA-8-Aoc-BBN[7–14]NH2 was initiated. Baseline weights, hematology profiles, and tumor measurements were obtained immediately prior to therapy administration. Four groups of animals were utilized; a saline placebo, a 5 mCi/kg single dose, a 10 mCilkg single dose, and a 20 mCi/kg single dose. Tumor measurements and weights were obtained twice weekly throughout the 14 weeks post injection.

Discussion

Figure 27:
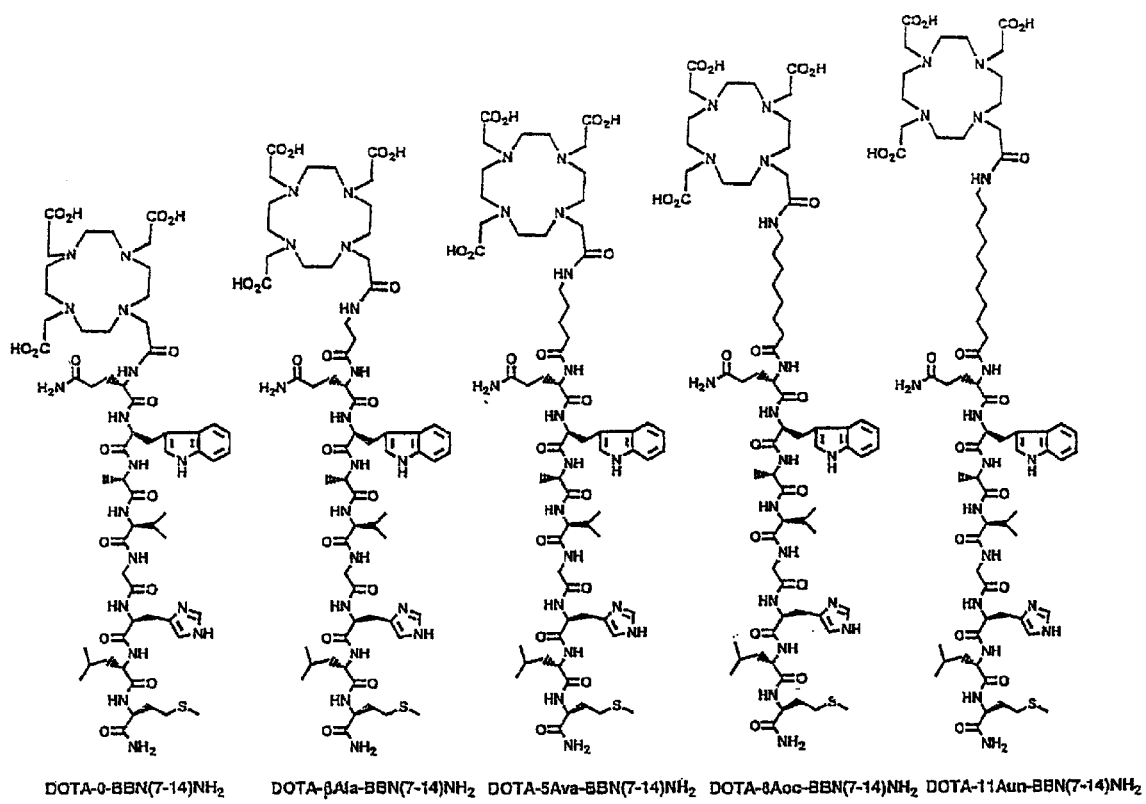
FIG. 27 illustrates further radiometal conjugates according to the present invention.
Figure 28:
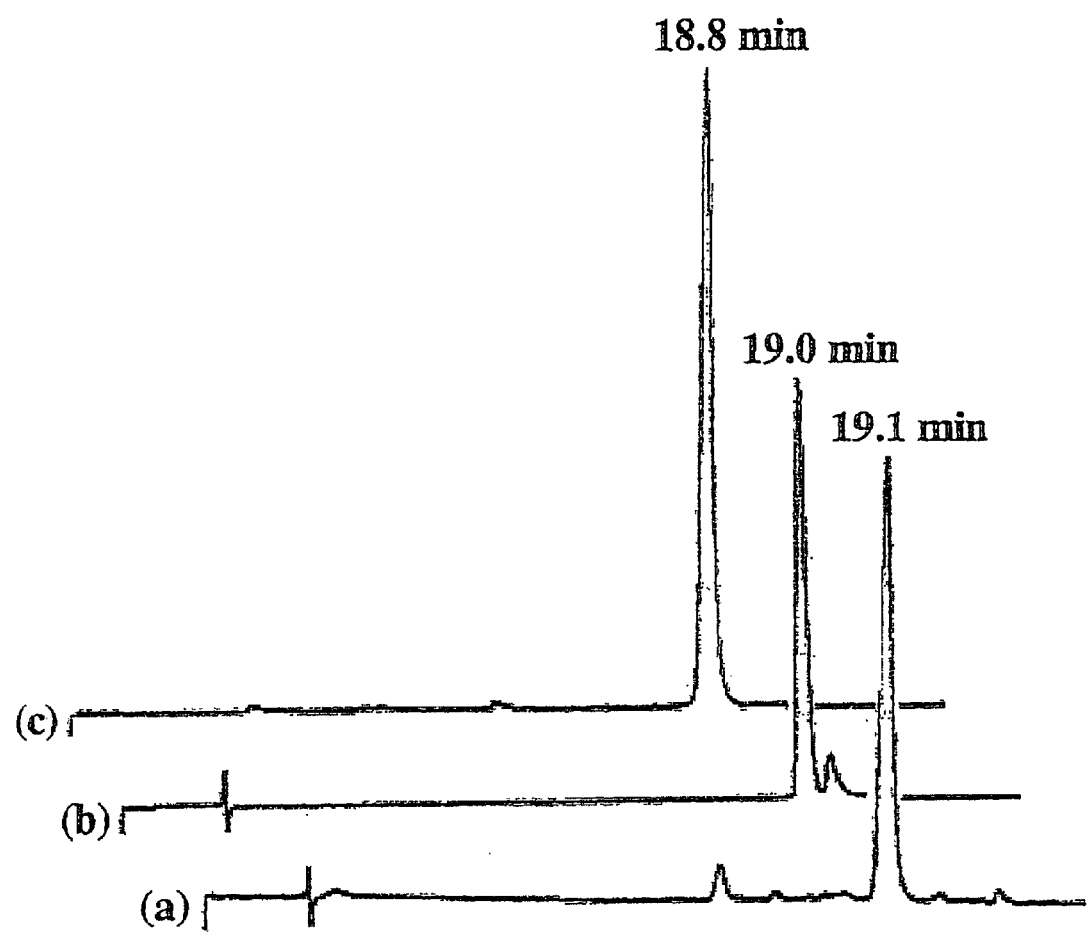
FIG. 28 are HPLC chromatograms of (a) DOTA-BBN [7–14-NH$_2$ (k =280 nm) (b) In-DOTA-BBN[7–14]NH$_2$ (λ=280 nm) and (c) $^{111}$In-DOTA-BBN[7–14]NH$_2$ (radiometric)
Figure 29:
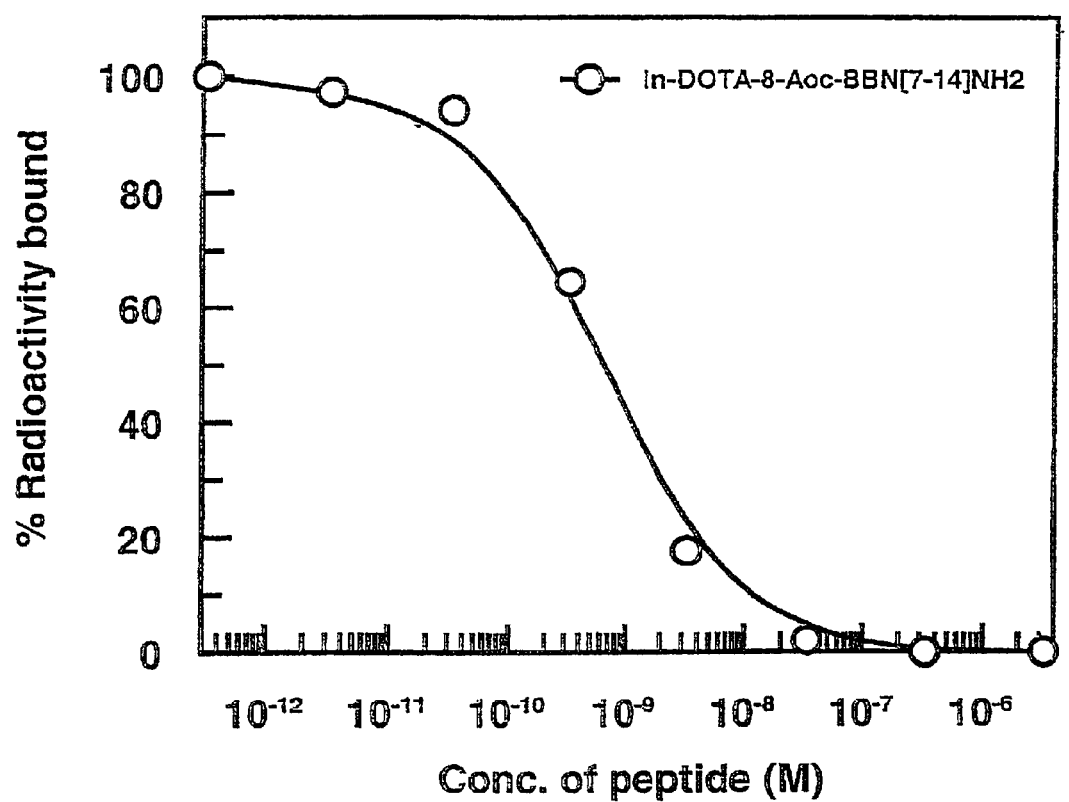
FIG. 29 is a graph showing the competitive binding assay of In-DOTA-8-Aoc-BBN[7–14]NH$_2$ v. $^{125}$-Tyr4-BBN in PC-3 cells.

A series of BBN-agonists containing the DOTA chelation system separated by spacers have been synthesized and characterized. [FIGS. 27 and 28; Tables 4 and 20] The in vitro binding affinity of the lndium-BBN analogs was measured in two cell lines, the human prostate cancer cell line, PC-3, and the human breast cancer cell line, T47D. Of the compounds tested, optimum binding of the In-DOTA-8-Aoc-BBN[7–14]NH2 analog was demonstrated in both cell lines examined. [FIG. 29 & Table 5]

Figure 30:
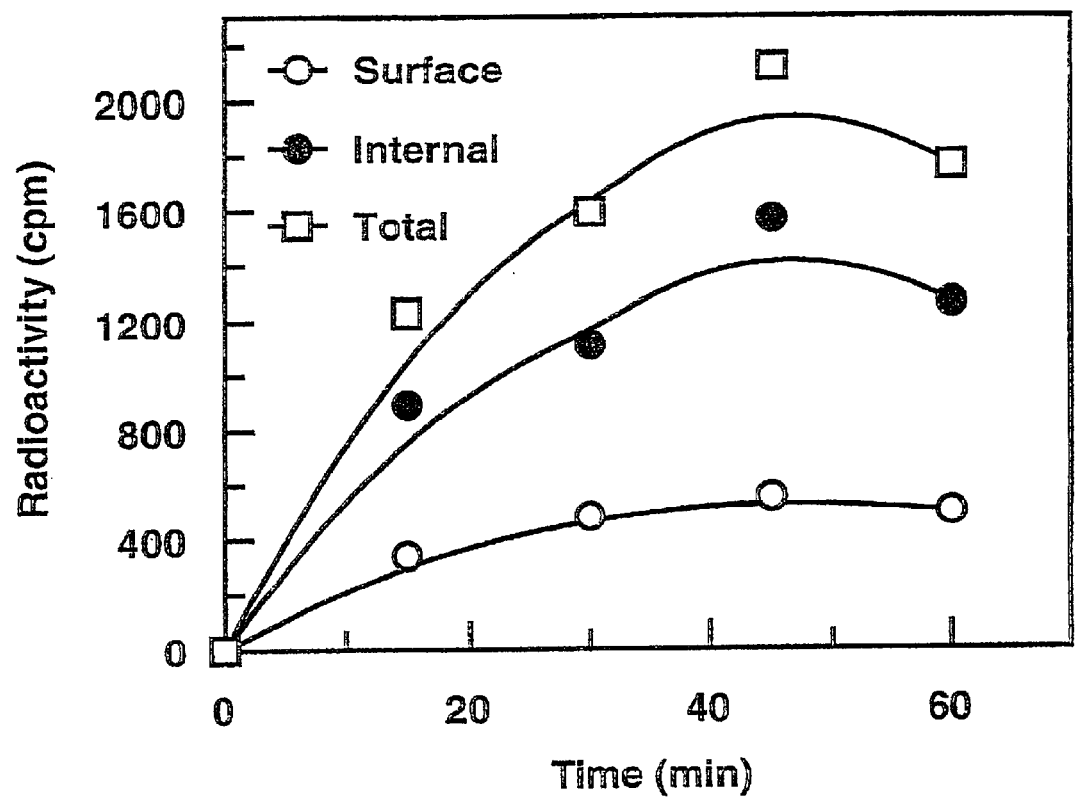
FIG. 30 is a graph showing the internalization of $^{111}$In-DOTA-8-Aoc-BBN[7–14]NH$_2$ in PC-3 cells.
Figure 31:
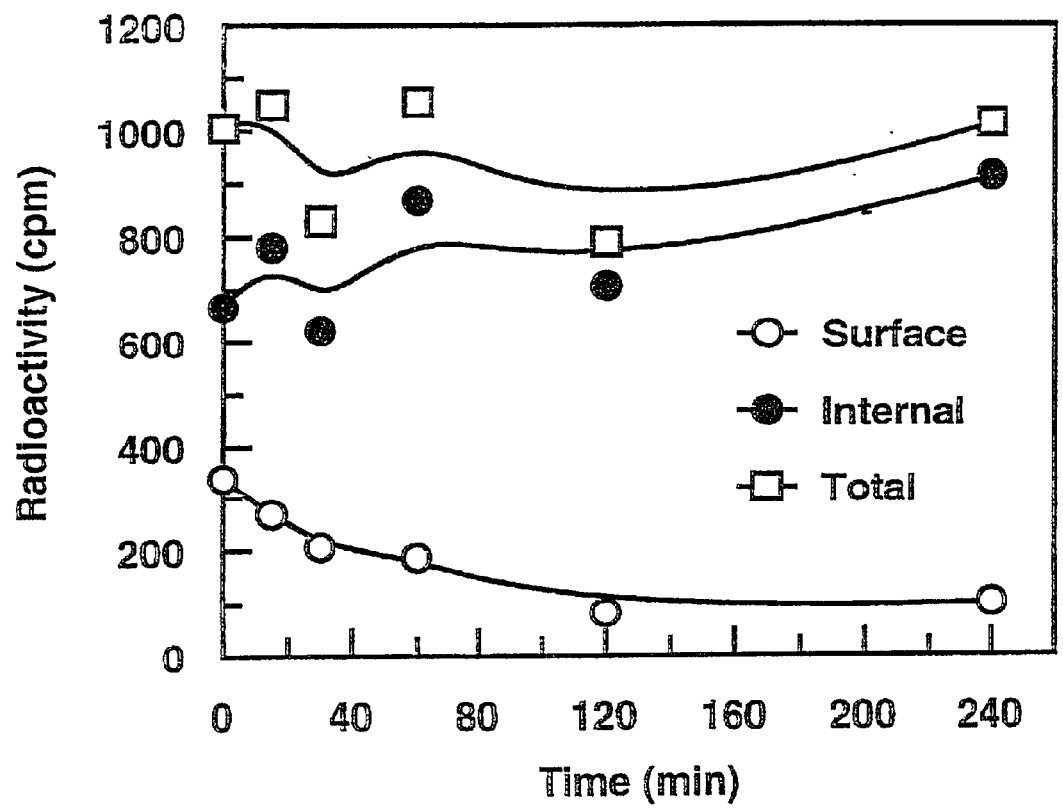
FIG. 31 is a graph showing the efflux of $^{111}$In-DOTA-8-Aoc-BBN[7–14]NH$_2$ in PC-3 cells.
Figure 32:
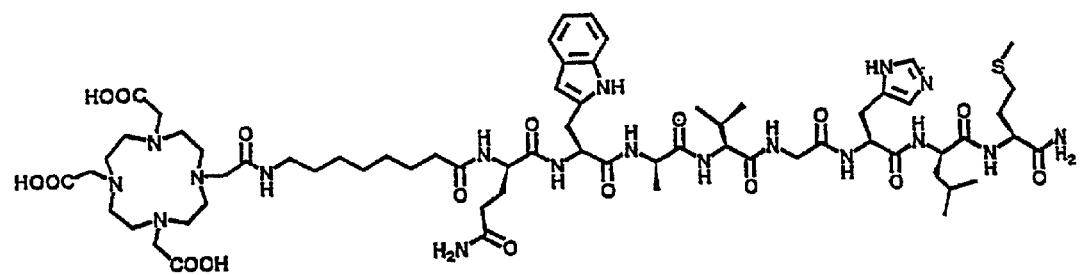
FIG. 32 is illustrates radiometal conjugate according to the present invention.

The In-DOTA-8-Aoc-BBN[7–14]NH2 analog underwent rapid receptor mediated endocytosis using an in vitro PC-3 cell assay system. Once internalized within PC-3 cells, the In-DOTA-8-Aoc-BBN[7–14]NH2 analog remained retained within the cells for a prolonged time period. [FIGS. 30 and 31]

In vivo analysis of the DOTA-BBN analogs in CF1 mice demonstrates that 111 In-DOTA-5-Ava-BBN[7–14]NH2, 111 In -DOTA-8-Aoc-BBN[7–14]NH2, 1111In-DOTA-11 -Aun-BBN[7–14]NH2 all target GRP receptor expression in vivo based on high uptake and accumulation of these compounds in the normal pancreas. Increasing hydrocarbon spacer length linking the DOTA metal chelation moiety to the GRP receptor binding moiety (BBN[7–14]NH2) results in compounds with increased hydrophobicity which subsequently shifts the clearance of these agents from the renal system (hydrophilic agents) to the hepatobiliary system (hydrophobic agents). [Tables 6 and 7]

Specific in vivo GRP receptor binding was demonstrated by performing competitive blocking assays in CF1 normal mice, where >98% of the normal receptor mediated uptake of 111 In -DOTA-8-Aoc-B BN[7–14]NH2 in normal pancreatic tissue was blocked by co-administration of an excess of bombesin. [Tables 8 and 9]

Prolonged PC-3 human prostate tumor uptake was demonstrated for 111 In-DOTA-8-Aoc-BBN[7–14]NH2 and 90Y -DOTA-8-Aoc-BBN[7–14]NH2 using a xenograft mouse model. [Tables 10–13]

Prolonged MDA-MB-23 1 human breast tumor uptake was demonstrated for 111In -DOTA-8-Aoc-BBN[7–14]NH2 using a xenograft mouse model. [Table 14]

These in vivo pharmacokinetic studies in CF1 mice have demonstrated that the radiometallated bombesin analogues (111 In and 90Y) clear from the blood pool, into the renal-urinary excretion pathway.

Competitive Binding Assay Results

The 111 In and 90Y complexes of one lead candidate, DOTA-8-Aoc-BBN[7–14]NH2, have been synthesized and evaluated in vitro and in vivo. In vitro competitive binding assays, employing PC-3 human prostate tumor cells, demonstrated an average $IC_{50}$ value of 1.69 nM for the In-DOTA-8-Aoc-BBN[7–14]NH2 complex.

In Vivo Pharmacokinetic Results in PC-3 Tumor Bearing Mice

In vivo pharmacokinetic studies of 111 In-DOTA-8-Aoc-BBN[7–14]NH2 in PC-3 prostate tumor bearing mice conducted at 1,4,24,48, and 72 hours p.i. revealed efficient clearance from the blood pool (0.92 i 0.58 % ID, 1 hour p.i.) with excretion through the renal and hepatobiliary pathways (87% ID and 8.5% ID, at 24 hours p.i., respectively). Similar pharmacokinetic properties were observed with 90Y-DOTA-8-Aoc-BBN[7–14]NH2. Tumor targeting of PC-3 xenografted SCID mice resulted in tumor uptake and retention values of 3.63±1.11% ID/g, 1.78±1.09% ID/g, and 1.56 ±0.45% ID/g obtained at 1,4, and 24 hours p.i. respectively, for the 111 In-DOTA-8-Aoc-BBN-[7–1 4]NH2 complex. 90Y-DOTA-8-Aoc-BBN[7–14]NH2 exhibited nearly identical PC-3 tumor uptake and retention values of 2.95 i 0.99%[D/g, 1.98±0.66% ID/g, and 1.08±0.37% ID/g at 1, 4, and 24 hr p.i., respectively. Initial therapeutic assessment of the 90Y complex in PC-3 xenografted mice demonstrated that radiation doses of up to 20 mCi/kg were well tolerated with overall survival exhibiting a dose dependent response.

These pre-clinical observations show that peptide conjugates of this type exhibit properties suitable as clinical therapeutic/diagnostic pharmaceuticals. EXAMPLE 10 Binding of D(3TA-BBN Conjugates in Human Breast Cancer Cell Lines Expression of Gastrin Releasing Peptide receptors (GRP-Rs) in a variety of cancers including breast, prostate, small cell lung, and pancreatic is well known. Recently, the first positive clinical images of GRP-R expression in human metastatic breast cancer patients were obtained [C. Van de Wiele et al., Eur. J. Nucl. Med. (2000) 27:1694–1699] with the compound, 99mTc-N3S-5-Ava-BBN[7–14)NH2, initially developed in our laboratory. The continued efforts in the development of GRP targeted radiopharmaceuticals has led to the synthesis of a series of DOTA incorporated peptides for the complexation of 111 In/90Y.

Methods: Six synthetic peptides were constructed in an X-Y-Z fashion where X=the DOTA chelation system, Y=the linking arm, and Z=the BBN[7–14)NH2 sequence. The six peptides differed in the selection of linking arms, comprising either amino acid tethers; -G-G-G-, -G-S-G-,or S-G-S-, or alkyl carbon chain tethers; 5-Ava, 8-Aoc, or 1 1-Aun. The In complexes of all peptides were prepared, purified by RPHPLC, and characterized by ES-MS as described in example 9.

Results: Pharmacokinetic studies conducted in CF1 mice revealed that 111 In-DOTA-8-Aoc-BBN[7–14)NH2 exhibited optimum clearance kinetics while maintaining selective and high in vivo GRP receptor targeting. 111 ln-DOTA-8-Aoc-BBN[7–14)NH2 exhibited an $IC_{50}$ value of 1.23±0.25 nM for the GRP receptor expressed by the T47D human breast cancer cell line. Pharmacokinetic studies of 111 In-DOTA-8-Aoc-BBN[7–14)NH2 conducted in MDA-MB-231 human breast cancer cell line xenografted SCID mice demonstrated specific tumor targeting with 0.83±0.23% IDig obtained at 1 hour post injection. Residualization of the radiolabel within the tumor was observed with 46%, and 28%, of the initial uptake retained at 4, and 24 hours, respectively.

Conclusion: These results show that GRP-R specific radiopharmaceuticals incorporating the DOTA chelation system are beneficial for the development of diagnostic/ therapeutic matched pair agents to target breast cancer.

EXAMPLE 11

Lutetium DOTA-BBN Compounds

A conjugate, 177Lu-DOTA-8-Aoc-BBN[7–14]NH2, was routinely prepared in high yield (>95%) by addition of 177LuCl3 to an aqueous solution (Ammonium Acetate) of DOTA-8-Aoc-BBN[7–14]NH2 (3.4x10–8 mols) [pH =5.5, Temp. =800C, RT =1 hour]. RCP determination demonstrated the stability of the conjugate over a wide range of pH values over a time course of 24 hours. The HPLC chromatogram of 177Lu-DOTA-8-Aoc-BBN[7–14INH2 showed a retention time of 19.0 minutes. Under identical chromatographic conditions, DOTA-8-Aoc-BBN[7–14]NH2 has a retention time of 20.5 minutes, allowing for peak purification of the radiolabeled conjugate. Collection of and counting of the 177Lu-DOTA-8-Aoc-BBN[7–14]NH2 eluant peak in a NaI well counter further demonstrated the stability of the new complex as >95% of the activity loaded onto the column was recovered as a singular species.

The biodistribution studies of 177Lu-DOTA-8-Aoc-BBN[7–14]NH2 were determined in tumor bearing (PC-3), SCID mice (TABLE 19). This 177Lu-conjugate cleared efficiently from the bloodstream within 1 hour post-injection. For example, 0.62±0.44%ID remained in whole blood at 1 hour p.i. The majority of the activity was excreted via the renal-urinary excretion pathway (i.e., 67.41±2.45% at 1 hour p.i. and 85.9 i 1.4% at 24 hour p.i.), with, the remainder of the radioactivity being excreted through the hepatobiliary pathway. Receptor-mediated, tumor targeting of the PC-3 xenografted SCID mice resulted in tumor uptake and retention values of 4.22±1.09%ID/g, 3.03±0.91%ID/g, and 1.54±1.14% ID/g at 1,4, and 24 hours, respectively.

EXPERIMENTAL: To 50 ug (3.4×10–8 mols) of DOTA-8-Aoc-BBN[7–14]NH2 in 50[L of 0.2M Ammonium Acetate was added 150 uL of 0.4M Ammonium Acetate. To this solution was added 50 uL of 177LuCi3 (2mCi in 0.05N HCI, Missouri University Research Reactor). The solution was allowed to incubate at 800 C. for 1 hour, after which 50lg of 0.002M EDTA was added in order to scavenge uncomplexed Lutetium. Quality control of the final product was determined by reversed-phase HPLC. Peak purification of the labeled species was performed by collecting the sample from the HPLC eluant, into a solution of lmg/mL bovine serum albumin/0.1 M Na2HPO4. All further analyses were carried out using the HPLC-purified products.

HPLC analysis of each of the new compounds was performed using an analytical C-18 reversed phase column (Phenomenex, 250×4.6mm, 5um). The mobile phase consisted of a linear gradient system, with solvent A corresponding to 100% water with 0.1% trifluoroacetic acid and solvent B corresponding to 100% acetonitrile with 0.1 % trifluoroacetic acid. The mobile phase started with solvent compositions of 80% A:20%B. At time=30 minutes, the solvent compositions were 70% A:30% B. Solvent compositions of the mobile phase remained as such (70%A:30%B) for a period of two minutes before being changed to 100% B. At time=34 minutes, the solvent composition was again changed to 80%A:20%B for column re-equilibration. The flow rate of the mobile phase was 1.5 mL/min. The chart speed of the integrator was 0.5 cm/min. The results of these analyses are shown in Table 20.

In vivo analysis of the DOTA-BBN analogs in CF1 mice demonstrates that 149Pm-DOTA-5-Ava-BBN[7–14]NH2 and 149Pm-DOTA-8-Aoc-BBN[7–14]NH2 target GRP receptor expression in vivo based on high uptake and accumulation of these compounds in the normal pancreas, which contain high levels of the GRP receptor [Tables 15 and 16] In vivo analysis of the DOTA-BBN analogs in CF1 mice demonstrates that 177Lu-DOTA-5-Ava-BBN[7–1–4]NH2, 177Lu-DOTA-8-Aoc-BBN[7–1 4]NH2, and 177Lu-DOTA-1 1-Aun-BBN[7–14]NH2 all target GRP receptor expression in vivo based on high uptake and accumulation of these compounds in the normal pancreas. [Tables 17 and 18] The biodistribution studies of 177Lu-DOTA-8-Aoc-BBN[7–14]NH2 were determined in SCID mice bearing human prostate cancer, PC-3 tumors. The mice were injected with 4[Ci of the complex in 1 00[L of isotonic saline via the tail vein. The mice were euthanized by cervical dislocation. Tissues and organs were excised from the animals following at 1 hour, 4 hour, and 24 hours post-injection (p.i.). Subsequently, the tissues and organs were weighed and counted in a NaI well counter and the percent injected dose (% ID) and % ID/g of each organ or tissue calculated. The % ID in whole blood was estimated assuming a whole-blood volume of 6.5% the total body weight.

Prolonged PC-3 human prostate tumor uptake was demonstrated for 177Lu DOTA-8-Aoc-BBN[7–14] using a xenograft mouse model of human prostate cancer. [Table 19 and 20]

CONCLUSION: This pre-clinical evaluation of 177Lu-DOTA-8-Aoc-BBN[7–14]NH2 and 149Pm-DOTA-8-Aoc-BBN[7–14]NH2 suggests the potential for peptide conjugates of this type to be used as site-directed, therapeutic radiopharmaceuticals.

TABLE B

Biodistribution of 99mTc-BBN-122 in normal CF-1 mice at 0.5, 1, 4 and 24 hr post-IV injection. Results expressed as % ID/organ

| Organ[c] | % Injected Dose/Organ[a] | | | |
|---|---|---|---|---|
|  | 30 min | 1 hr | 4 hr | 24 hr |
| Blood[d] | 3.52 ± 2.16 | 1.08 ± 0.34 | 0.59 ± 0.24 | 0.12 ± 0.01 |
| Liver | 4.53 ± 0.93 | 4.77 ± 1.40 | 1.49 ± 0.32 | 0.32 ± 0.06 |
| Stomach | 2.31 ± 0.45 | 1.61 ± 0.81 | 1.75 ± 0.20 | 0.30 ± 0.06 |
| Lg. Intestine[b] | 2.84 ± 0.32 | 24.17 ± 7.91 | 23.85 ± 7.02 | 0.61 ± 0.14 |
| Sm. Intestine[b] | 43.87 ± 1.51 | 23.91 ± 9.08 | 5.87 ± 7.09 | 0.42 ± 0.06 |
| Kidneys[b] | 1.49 ± 0.19 | 1.15 ± 0.10 | 0.55 ± 0.06 | 0.20 ± 0.01 |
| Urine[b] | 26.78 ± 1.05 | 33.79 ± 1.76 | ~35 | ~35 |
| Muscle | 0.02 ± 0.01 | 0.01 ± 0.00 | 0.01 ± 0.01 | 0.01 ± 0.01 |
| Pancreas | 5.30 ± 0.63 | 3.20 ± 0.83 | 1.21 ± 0.13 | 0.42 ± 0.17 |

[a]Each value in the table represents the mean and SD from 5 animals in each group
[b]At 4 and 24 hr, feces containing 99Tc had been excreted from each animal and the % ID in the urine was estimated to be approximately 60% of the ID.
[c]All other organs excised (incl. Brain, heart, lung and spleen) shown <0.10% at t ≧ 1 hr.
[d]% ID in the blood estimated assuming the whole blood volume is 6:5% of the body weight.

TABLE C

Biodistribution of 99mTc-BBN-122 in normal CF-1 mice at 0.5, 1, 4 and 24 hr post I.V. injection. Results expressed as % ID/gm.

| Organ | % Injected Dose/gma | | | |
|---|---|---|---|---|
|  | 30 min | 1 hr | 4 hr | 24 hr |
| Blood[b] | 2.00 ± 1.28 | 0.63 ± 0.19 | 0.34 ± 0.11 | 0.08 ± 0.00 |
| Liver | 2.70 ± 0.41 | 3.14 ± 0.81 | 0.96 ± 0.20 | 0.22 ± 0.05 |
| Kidneys | 3.99 ± 0.76 | 3.10 ± 0.31 | 1.58 ± 0.15 | 0.64 ± 0.07 |
| Muscle | 0.23 ± 0.08 | 0.13 ± 0.02 | 0.05 ± 0.01 | 0.01 ± 0.01 |
| Pancreas | 16.89 ± 0.95 | 12.63 ± 1.87 | 5.05 ± 0.42 | 1.79 ± 0.71 |
| P/B1 and P/M Update Ratios | | | | |
| Pancreas/Blood | 8.42 | 19.76 | 14.78 | 20.99 |
| Pancreas/Muscle | 73.16 | 93.42 | 92.25 | 142.76 |

[a]Each value in the table represents the mean and SD from 5 animals in each group.
[b]% ID in the blood estimated assuming the whole blood volume is 6:5% of the body weight.

TABLE D

Biodistribution of $^{99m}$Tc-BBN-122 in PC-3 tumor bearing SCID mice at 1, 4 and 24 hr post-I.V. injection. Results expressed as % ID/organ.

Tumor Line: PC-3

| Organ[c] | % ID per Organ[a] | | |
|---|---|---|---|
| | 1 hr | 4 hr | 24 hr |
| Blood[b] | 1.16 ± 0.27 | 0.47 ± 0.06 | 0.26 ± 0.05 |
| Liver | 1.74 ± 0.64 | 0.72 ± 0.10 | 0.29 ± 0.05 |
| Stomach | 0.43 ± 0.13 | 0.29 ± 0.22 | 0.08 ± 0.02 |
| Lg. Intestine | 9.18 ± 19.42 | 42.55 ± 8.74 | 0.64 ± 0.17 |
| Sm. Intestine | 46.55 ± 16.16 | 2.13 ± 0.76 | 0.31 ± 0.04 |
| Kidneys | 1.16 ± 0.20 | 0.60 ± 0.06 | 0.16 ± 0.01 |
| Urine[d] | 32.05 ± 12.78 | ~35 | ~35 |
| Muscle | 0.01 ± 0.00 | 0.00 ± 0.00 | 0.00 ± 0.00 |
| Pancreas | 1.69 ± 0.61 | 1.05 ± 0.13 | 0.34 ± 0.08 |
| Tumor | 1.00 ± 0.78 | 0.49 ± 0.08 | 0.49 ± 0.25 |

[a]Each value in the table represents the mean and SD from 5 animals in each group.
[b]At 4 and 24 hr, feces containing $^{99m}$Tc had been excreted from each animal and the % ID in the urine was estimated to be approximately 60% of the ID.
[c]All other organs excised (incl. brain, heart, lung and spleen) showed < 0.10% at t ≥ 1 hr.
[d]% ID in the blood estimated assuming the whole blood volume is 6:5% of the body weight.

TABLE E

Biodistribution of $^{99m}$Tc-BBN-122 in PC-3 tumor bearing SCID mice at 1.4 and 24 hr post-I.V. injection. Results expressed as % ID/Gm.

Tumor Line: PC-3

| Organ[c] | % ID per gm[a] | | |
|---|---|---|---|
| | 1 hr | 4 hr | 24 hr |
| Blood[b] | 0.97 ± 0.26 | 0.31 ± 0.33 | 0.18 ± 0.34 |
| Liver | 2.07 ± 0.88 | 0.64 ± 0.05 | 0.26 ± 0.04 |
| Kidneys | 4.80 ± 1.33 | 2.23 ± 0.35 | 0.60 ± 0.04 |
| Muscle | 0.18 ± 0.12 | 0.06 ± 0.03 | 0.05 ± 0.04 |
| Pancreas | 10.34 ± 3.38 | 5.08 ± 1.12 | 1.47 ± 0.23 |
| Tumor | 2.07 ± 0.50 | 1.75 ± 0.61 | 1.28 ± 0.22 |
| T/Bl, T/M, P/Bl and P/M Uptake Ratios | | | |
| Tumor/Blood | 2.13 | 5.52 | 6.79 |
| Tumor/Muscle | 11.44 | 25.38 | 21.62 |
| Pancreas/Blood | 10.64 | 15.96 | 7.81 |
| Pancreas/Muscle | 57.14 | 73.40 | 24.87 |

[a]Each value in the table represents the mean and SD from 5 animals in each group.
[b]% ID in the blood estimated assuming the whole blood volume is 6:5% of the body weight.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

Throughout this application, various publications are referenced by citation and number. Full citations for the publication are listed below. the disclosure of these publications in their entireties are hereby incorporated by reference into this application in order to more fully describe the state of the art to which this invention pertains.

TABLE 1

Binding Affinity of Rh-BBN-37 for GRP Receptors Expressed on Neoplasms

| Type of Cancer | Cell Line | IC$_{50}$ (Mean Value) |
|---|---|---|
| Pancreatic CA | CF PAC1 | 3.2 × 10$^{-9}$ |
| Prostate CA | PC-3 | 7.0 × 10$^{-9}$ |

TABLE 2

| | (% Dose) | | |
|---|---|---|---|
| Complex | $^{105}$Rh-Peptide22 30 min n = 9 | $^{105}$Rh-Peptide22 1 hr n = 9 | $^{105}$Rh-Peptide22 2 hr n = 9 |
| Organ (% Dose) | | | |
| Brain | 0.08 ± 0.02 | 0.04 ± 0.01 | 0.06 ± 0.09 |
| Blood | 4.48 ± 1.24 | 1.86 ± 0.38 | 0.99 ± 0.24 |
| Heart | 0.13 ± 0.03 | 0.08 ± 0.03 | 0.04 ± 0.04 |
| Lung | 0.25 ± 0.08 | 0.20 ± 0.09 | 0.15 ± 0.09 |
| Liver | 7.97 ± 2.85 | 8.51 ± 2.33 | 8.57 ± 2.04 |
| Spleen | 0.07 ± 0.03 | 0.09 ± 0.08 | 0.05 ± 0.01 |
| Stomach | 1.11 ± 0.76 | 0.59 ± 0.21 | 0.30 ± 0.16 |
| Large Intestine | 0.73 ± 0.16 | 3.21 ± 3.38 | 8.91 ± 3.79 |
| Small Intestine | 6.29 ± 1.87 | 6.98 ± 1.87 | 3.48 ± 1.78 |
| Kidneys | 4.25 ± 1.33 | 3.25 ± 0.60 | 2.44 ± 0.64 |
| Bladder | 44.66 ± 7.29 | 62.88 ± 3.84 | 68.41 ± 6.63 |
| Muscle | 0.06 ± 0.03 | 0.03 ± 0.03 | 0.01 ± 0.01 |
| Pancreas | 0.95 ± 0.46 | 1.15 ± 0.49 | 1.01 ± 0.14 |
| Carcass | 32.90 ± 6.61 | 12.62 ± 4.77 | 6.37 ± 1.17 |
| Organ (% D/GM) | | | |
| Brain | 0.21 ± 0.07 | 0.14 ± 0.08 | 0.16 ± 0.28 |
| Blood | 2.22 ± 0.40 | 1.02 ± 0.22 | 0.51 ± 0.11 |
| Heart | 0.92 ± 0.25 | 0.64 ± 0.20 | 0.38 ± 0.33 |
| Lung | 1.44 ± 0.33 | 1.24 ± 0.54 | 0.92 ± 0.69 |
| Liver | 4.33 ± 1.52 | 5.18 ± 1.52 | 5.17 ± 1.12 |
| Spleen | 0.86 ± 0.38 | 1.10 ± 0.65 | 0.84 ± 0.53 |
| Stomach | 2.46 ± 1.65 | 1.53 ± 0.74 | 0.71 ± 0.33 |
| Large Intestine | 0.78 ± 0.19 | 4.42 ± 4.62 | 10.10 ± 4.58 |
| Small Intestine | 4.73 ± 1.47 | 5.84 ± 1.01 | 2.86 ± 1.47 |
| Kidneys | 7.57 ± 1.44 | 6.70 ± 0.75 | 4.60 ± 0.83 |
| Muscle | 0.53 ± 0.32 | 0.61 ± 0.97 | 0.24 ± 0.24 |
| Pancreas | 3.12 ± 0.99 | 4.31 ± 1.98 | 3.88 ± 1.25 |

TABLE 3

| | (% Dose) | | |
|---|---|---|---|
| Complex | $^{105}$Rh-Pept37 30 min n = 5 | $^{105}$Rh-Pept37 1 hr n = 9 | $^{105}$Rh-Pept37 2 hr n = 7 |
| Organ (% Dose) | | | |
| Brain | 0.03 ± 0.01 | 0.07 ± 0.11 | 0.03 ± 0.03 |
| Blood | 3.09 ± 0.54 | 1.46 ± 0.62 | 0.66 ± 0.26 |
| Heart | 0.12 ± 0.03 | 0.05 ± 0.03 | 0.04 ± 0.02 |
| Lung | 0.26 ± 0.09 | 0.12 ± 0.07 | 0.08 ± 0.11 |
| Liver | 13.04 ± 1.93 | 13.00 ± 3.59 | 10.12 ± 1.86 |
| Spleen | 0.21 ± 0.13 | 0.16 ± 0.08 | 0.10 ± 0.04 |
| Stomach | 0.80 ± 0.34 | 0.65 ± 0.52 | 0.83 ± 0.96 |
| Large Intestine | 2.05 ± 0.69 | 2.96 ± 1.67 | 8.07 ± 2.25 |
| Small Intestine | 8.44 ± 1.89 | 11.38 ± 3.02 | 5.04 ± 2.27 |
| Kidneys | 7.82 ± 2.52 | 6.04 ± 1.68 | 4.57 ± 1.29 |
| Bladder | 39.65 ± 7.31 | 51.82 ± 7.53 | 62.32 ± 5.78 |
| Muscle | 0.06 ± 0.03 | 0.02 ± 0.01 | 0.02 ± 0.02 |
| Pancreas | 2.73 ± 1.14 | 3.63 ± 1.22 | 2.25 ± 1.02 |
| Carcass | 24.35 ± 7.69 | 9.81 ± 2.91 | 6.37 ± 1.73 |

TABLE 3-continued

|  | (% Dose) | | |
|---|---|---|---|
| Complex | $^{105}$Rh-Pept37 30 min n = 5 | $^{105}$Rh-Pept37 1 hr n = 9 | $^{105}$Rh-Pept37 2 hr n = 7 |
| Organ (% D/GM) | | | |
| Brain | 0.10 ± 0.05 | 0.26 ± 0.41 | 0.10 ± 0.09 |
| Blood | 1.60 ± 0.30 | 0.72 ± 0.31 | 0.34 ± 0.15 |
| Heart | 0.92 ± 0.26 | 0.38 ± 0.21 | 0.28 ± 0.17 |
| Lung | 1.52 ± 0.48 | 0.76 ± 0.47 | 0.46 ± 0.50 |
| Liver | 7.31 ± 1.15 | 7.65 ± 1.29 | 6.30 ± 1.73 |
| Spleen | 2.18 ± 1.17 | 1.59 ± 0.71 | 1.05 ± 0.44 |
| Stomach | 1.53 ± 0.67 | 1.63 ± 1.17 | 2.18 ± 2.35 |
| Large Intestine | 2.46 ± 0.70 | 3.80 ± 2.42 | 11.84 ± 4.39 |
| Small Intestine | 5.69 ± 1.26 | 7.85 ± 1.87 | 3.81 ± 2.01 |
| Kidneys | 14.28 ± 2.84 | 11.21 ± 3.68 | 8.39 ± 2.36 |
| Muscle | 0.73 ± 0.39 | 0.20 ± 0.14 | 0.39 ± 0.38 |
| Pancreas | 14.02 ± 3.23 | 15.54 ± 6.21 | 9.91 ± 5.35 |

TABLE 4

ES-MS and HPLC data of DOTA-BBN[7–14]NH$_2$ and In-DOTA-BBN[7–14]NH$_2$ analogues.

| BBN Analogue | Mol. Formula | ES-MS Calculated | ES-MS Observed | HPLC $t_r$ (min)[a] |
|---|---|---|---|---|
| 0 | $C_{59}H_{91}N_{17}O_{16}S$ | 1326.5 | 1326.6 | 13.2 |
| 3 | $C_{62}H_{96}N_{18}O_{17}S$ | 1397.6 | 1397.4 | 13.4 |
| 5 | $C_{64}H_{100}N_{18}O_{17}S$ | 1425.7 | 1425.8 | 14.0 |
| 8 | $C_{67}H_{106}N_{18}O_{17}S$ | 1467.8 | 1467.8 | 19.1 |
| 11 | $C_{70}H_{112}N_{18}O_{17}S$ | 1509.8 | 1509.8 | 17.1[b] |
| In-0 | $C_{59}H_{88}N_{17}O_{16}SIn$ | 1438.3 | 1438.2 | 12.9 |
| In-3 | $C_{62}H_{93}N_{18}O_{17}SIn$ | 1509.4 | 1509.6 | 12.7 |
| In-5 | $C_{64}H_{97}N_{18}O_{17}SIn$ | 1536.5 | 1537.7 | 13.6 |
| In-8 | $C_{67}H_{103}N_{18}O_{17}SIn$ | 1579.6 | 1579.7 | 19.0 |
| In-11 | $C_{70}H_{109}N_{18}O_{17}SIn$ | 1621.6 | 1621.7 | 16.8[b] |

TABLE 5

$IC_{50}$ (nM) values (n = 3 or 4 separate experiments performed in duplicate) of In-DOTA-BBN[7–14]NH$_2$ analogues vs. $^{125}$I-Tyr$^4$-BBN in human prostate PC-3 cells and human breast carcinoma T47D cells.

| BBN Analogue | PC-3 $IC_{50}$ (nM) | T47D $IC_{50}$ (nM) |
|---|---|---|
| 0 | 110.6 ± 32.3 | 322 ± 54.5 |
| β-Ala | 2.1 ± 0.3 | 4.7 ± 0.7 |
| 5-Ava | 1.7 ± 0.4 | 2.3 ± 1.01 |
| 8-Aoc | 0.6 ± 0.1 | 1.3 ± 0.21 |
| 11-Aun | 64.0 ± 11.2 | 516 ± 32.2 |

TABLE 6

$^{111}$In-DOTA-SPACER-BBN[7–14]NH$_2$ biodistribution (Avg % ID/gm, n = 5) in CF1 normal mice after 1 hour post-injection.

| Tissue | Spacer 0 | β-Ala | 5-Ava | 8-Aoc | 11-Aun |
|---|---|---|---|---|---|
| Blood | 0.10 ± 0.03 | 0.11 ± 0.06 | 0.20 ± 0.07 | 0.32 ± 0.09 | 0.34 ± 0.08 |
| Heart | 0.05 ± 0.02 | 0.06 ± 0.04 | 0.10 ± 0.04 | 0.05 ± 0.02 | 0.13 ± 0.04 |
| Lung | 0.13 ± 0.03 | 0.11 ± 0.08 | 0.20 ± 0.06 | 0.31 ± 0.07 | 0.26 ± 0.05 |
| Liver | 0.09 ± 0.01 | 0.11 ± 0.02 | 0.16 ± 0.02 | 0.65 ± 0.07 | 1.22 ± 0.25 |
| Spleen | 0.08 ± 0.02 | 0.37 ± 0.06 | 0.87 ± 0.28 | 1.51 ± 0.41 | 1.15 ± 0.38 |
| Stomach | 0.06 ± 0.03 | 0.30 ± 0.07 | 0.71 ± 0.24 | 1.02 ± 0.26 | 1.05 ± 0.25 |
| L. Intestine | 0.09 ± 0.03 | 1.10 ± 0.78 | 3.07 ± 0.86 | 2.66 ± 1.07 | 4.34 ± 1.34 |
| S. Intestine | 0.44 ± 0.64 | 1.01 ± 0.37 | 3.49 ± 0.87 | 4.43 ± 0.90 | 11.12 ± 2.07 |
| Kidney | 1.24 ± 0.14 | 1.40 ± 0.27 | 1.84 ± 0.44 | 2.37 ± 0.31 | 2.06 ± 0.31 |
| Muscle | 0.03 ± 0.02 | 0.03 ± 0.02 | 0.05 ± 0.02 | 0.12 ± 0.05 | 0.09 ± 0.03 |
| Pancreas | 0.20 ± 0.04 | 4.92 ± 0.37 | 15.78 ± 2.54 | 26.97 ± 3.97 | 26.00 ± 3.46 |

TABLE 7

$^{111}$In-DOTA-SPACER-BBN[7–14]NH$_2$ biodistribution (Avg % ID, n = 5) in CF1 normal mice after 1 hour post-injection.

| Tissue | Spacer 0 | β-Ala | 5-Ava | 8-Aoc | 11-Aun |
|---|---|---|---|---|---|
| Blood | 0.22 ± 0.07 | 0.23 ± 0.10 | 0.45 ± 0.14 | 0.66 ± 0.13 | 0.79 ± 0.20 |
| Heart | 0.01 ± 0.00 | 0.01 ± 0.01 | 0.02 ± 0.01 | 0.01 ± 0.00 | 0.02 ± 0.01 |
| Lung | 0.03 ± 0.00 | 0.03 ± 0.02 | 0.04 ± 0.01 | 0.07 ± 0.02 | 0.08 ± 0.01 |
| Liver | 0.17 ± 0.02 | 0.17 ± 0.03 | 0.26 ± 0.03 | 1.02 ± 0.08 | 2.44 ± 0.50 |
| Spleen | 0.01 ± 0.00 | 0.05 ± 0.00 | 0.11 ± 0.04 | 0.17 ± 0.04 | 0.19 ± 0.04 |
| Stomach | 0.03 ± 0.01 | 0.13 ± 0.02 | 0.37 ± 0.16 | 0.50 ± 0.06 | 0.53 ± 0.11 |
| L. Intestine | 0.10 ± 0.02 | 0.90 ± 0.57 | 2.74 ± 0.80 | 3.02 ± 0.33 | 5.54 ± 2.42 |
| S. Intestine | 0.25 ± 0.04 | 1.57 ± 0.65 | 0.11 ± 0.04 | 6.58 ± 1.10 | 17.84 ± 1.40 |

TABLE 7-continued $^{111}$In-DOTA-SPACER-BBN[7–14]NH$_2$ biodistribution (Avg % ID, n = 5) in CF1 normal mice after 1 hour post-injection.

| | Spacer | | | | |
|---|---|---|---|---|---|
| Tissue | 0 | β-Ala | 5-Ava | 8-Aoc | 11-Aun |
| Kidney | 0.57 ± 0.02 | 0.62 ± 0.10 | 0.75 ± 0.14 | 1.04 ± 0.12 | 1.07 ± 0.17 |
| Urine | 96.95 ± 0.37 | 92.41 ± 0.90 | 81.29 ± 1.32 | 71.61 ± 1.82 | 53.26 ± 0.90 |
| Muscle | 0.01 ± 0.00 | 0.01 ± 0.01 | 0.01 ± 0.01 | 0.02 ± 0.01 | 0.02 ± 0.01 |
| Pancreas | 0.07 ± 0.01 | 1.84 ± 0.35 | 5.57 ± 0.99 | 10.81 ± 0.78 | 11.56 ± 1.14 |
| Carcass | 1.78 ± 0.37 | 2.23 ± 0.36 | 3.15 ± 0.70 | 5.01 ± 0.47 | 7.35 ± 1.57 |

TABLE 8

$^{111}$In-DOTA-BBN[7–14]NH$_2$ analogues biodistribution (Avg % ID/gm, n = 5) in CF1 normal mice after 1 hour post-injection.

| Analogue Tissue | 8-Aoc | 8-Aoc Blocking |
|---|---|---|
| Blood | 0.32 ± 0.09 | 0.49 ± 0.15 |
| Heart | 0.05 ± 0.02 | 0.16 ± 0.06 |
| Lung | 0.31 ± 0.07 | 0.74 ± 0.17 |
| Liver | 0.65 ± 0.07 | 0.54 ± 0.13 |
| Spleen | 1.51 ± 0.41 | 0.15 ± 0.16 |
| Stomach | 1.02 ± 0.26 | 0.32 ± 0.34 |
| L. Intestine | 2.66 ± 1.07 | 0.16 ± 0.06 |
| S. Intestine | 4.43 ± 0.90 | 0.95 ± 0.18 |
| Kidney | 2.37 ± 0.31 | 2.19 ± 0.47 |
| Muscle | 0.12 ± 0.05 | 0.11 ± 0.07 |
| Pancreas | 26.97 ± 3.97 | 0.43 ± 0.10 |

TABLE 9

$^{111}$In-DOTA-BBN[7–14]NH$_2$ analogues biodistribution (Avg % ID, n = 5) in CF1 normal mice after 1 hour post-injection.

| Analogue Tissue | 8-Aoc | 8-Aoc Blocking |
|---|---|---|
| Blood | 0.66 ± 0.13 | 0.98 ± 0.23 |
| Heart | 0.01 ± 0.00 | 0.03 ± 0.01 |
| Lung | 0.07 ± 0.02 | 0.17 ± 0.05 |
| Liver | 1.02 ± 0.08 | 0.87 ± 0.10 |
| Spleen | 0.17 ± 0.04 | 0.02 ± 0.03 |
| Stomach | 0.50 ± 0.06 | 0.16 ± 0.12 |
| L. Intestine | 3.02 ± 0.33 | 0.15 ± 0.05 |
| S. Intestine | 6.58 ± 1.10 | 1.65 ± 0.19 |
| Kidney | 1.04 ± 0.12 | 0.92 ± 0.13 |
| Urine | 71.61 ± 1.82 | 88.19 ± 1.79 |
| Muscle | 0.02 ± 0.01 | 0.02 ± 0.01 |
| Pancreas | 10.81 ± 0.78 | 0.19 ± 0.03 |
| Carcass | 5.01 ± 0.47 | 7.42 ± 1.35 |

TABLE 10

$^{111}$In-DOTA-8-Aoc-BBN[7–14]NH$_2$ biodistribution (Avg % ID/gm, n = 5) in PC-3 tumor bearing mice.

| | Time | | | | | | |
|---|---|---|---|---|---|---|---|
| Tissue | 15 min | 30 min | 1 hr | 4 hrs | 24 hrs | 48 hrs | 72 hrs |
| Blood | 5.585 ± 2.43 | 1.46 ± 0.44 | 0.60 ± 0.39 | 0.27 ± 0.02 | 0.10 ± 0.03 | 0.07 ± 0.03 | 0.01 ± 0.02 |
| Heart | 2.20 ± 1.05 | 0.62 ± 0.33 | 0.25 ± 0.18 | 0.13 ± 0.06 | 0.05 ± 0.09 | 0.05 ± 0.05 | 0.01 ± 0.01 |
| Lung | 3.35 ± 1.22 | 0.94 ± 0.28 | 0.50 ± 0.39 | 0.25 ± 0.08 | 0.09 ± 0.07 | 0.06 ± 0.02 | 0.02 ± 0.02 |
| Liver | 2.03 ± 0.85 | 0.70 ± 0.21 | 1.34 ± 0.25 | 1.44 ± 0.57 | 0.37 ± 0.12 | 0.13 ± 0.04 | 0.07 ± 0.02 |
| Spleen | 2.21 ± 0.80 | 0.83 ± 0.26 | 1.39 ± 1.17 | 1.59 ± 0.27 | 0.46 ± 0.20 | 0.22 ± 0.22 | 0.08 ± 0.09 |
| Stomach | 3.30 ± 1.99 | 1.82 ± 0.44 | 1.99 ± 0.24 | 0.96 ± 0.57 | 0.30 ± 0.05 | 0.12 ± 0.03 | 0.05 ± 0.02 |
| L. Intestine | 8.58 ± 3.04 | 4.33 ± 0.44 | 4.29 ± 2.55 | 10.27 ± 2.70 | 2.35 ± 0.43 | 0.81 ± 0.20 | 0.45 ± 0.01 |
| S. Intestine | 7.82 ± 2.26 | 5.16 ± 1.06 | 6.80 ± 1.81 | 2.24 ± 0.35 | 0.89 ± 0.16 | 0.25 ± 0.06 | 0.12 ± 0.02 |
| Kidney | 29.03 ± 14.40 | 8.70 ± 2.80 | 5.66 ± 1.33 | 3.18 ± 0.43 | 1.18 ± 0.14 | 0.48 ± 0.09 | 0.20 ± 0.02 |
| Muscle | 1.30 ± 0.60 | 0.32 ± 0.12 | 0.08 ± 0.07 | 0.04 ± 0.02 | 0.05 ± 0.05 | 0.02 ± 0.04 | 0.01 ± 0.02 |
| Pancreas | 54.33 ± 9.70 | 27.87 ± 3.44 | 18.80 ± 10.97 | 16.55 ± 4.43 | 6.78 ± 1.15 | 0.77 ± 0.44 | 0.23 ± 0.08 |
| Tumor | 7.59 ± 2.11 | 4.58 ± 0.53 | 3.63 ± 1.11 | 1.78 ± 1.09 | 1.56 ± 0.45 | 0.68 ± 0.24 | 0.34 ± 0.10 |

TABLE 11

$^{11}$In-DOTA-8-Aoc-BBN[7–14]NH$_2$ biodistribution
(Avg % ID, n = 5) in PC-3 tumor bearing mice.

| Tissue | Time | | | | | | |
|---|---|---|---|---|---|---|---|
| | 15 min | 30 min | 1 hr | 4 hrs. | 24 hrs | 48 hrs | 72 hrs |
| Blood | 7.92 ± 2.03 | 2.47 ± 0.74 | 0.92 ± 0.58 | 0.40 ± 0.11 | 0.15 ± 0.04 | 0.12 ± 0.05 | 0.02 ± 0.03 |
| Heart | 0.20 ± 0.07 | 0.06 ± 0.02 | 0.03 ± 0.02 | 0.01 ± 0.01 | 0.00 ± 0.01 | 0.01 ± 0.01 | 0 00 ± 0.00 |
| Lung | 0.62 ± 0.25 | 0.20 ± 0.06 | 0.09 ± 0.07 | 0.05 ± 0.02 | 0.02 ± 0.01 | 0.01 ± 0.00 | 0 00 ± 0.00 |
| Liver | 1.85 ± 0.41 | 0.85 ± 0.21 | 1.41 ± 0.32 | 1.57 ± 0.72 | 0.40 ± 0.17 | 0.15 ± 0.04 | 0.08 ± 0.01 |
| Spleen | 0.10 ± 0.02 | 0.08 ± 0.03 | 0.09 ± 0.07 | 0.10 ± 0.04 | 0.03 ± 0.02 | 0.01 ± 0.01 | 0.01 ± 0.01 |
| Stomach | 0.98 ± 0.18 | 0.65 ± 0.04 | 0.52 ± 0.11 | 0.34 ± 0.23 | 0.09 ± 0.02 | 0.06 ± 0.02 | 0.02 ± 0.01 |
| L. Intestine | 5.84 ± 0.90 | 4.53 ± 0.45 | 2.18 ± 0.86 | 6.04 ± 2.05 | 1.46 ± 0.42 | 0.73 ± 0.21 | 0.41 ± 0.05 |
| S. Intestine | 6.98 ± 0.35 | 6.24 ± 0.46 | 7.45 ± 1.62 | 2.43 ± 0.56 | 0.98 ± 0.26 | 0.32 ± 0.07 | 0.15 ± 0.02 |
| Kidney | 7.18 ± 3.16 | 2.45 ± 0.78 | 1.81 ± 0.37 | 0.97 ± 0.08 | 0.36 ± 0.08 | 0.16 ± 0.04 | 0.06 ± 0.01 |
| Urine | 27.91 ± 10.33 | 62.61 ± 5.02 | 68.56 ± 6.96 | 81.83 ± 3.82 | 87.15 ± 4.31 | 91.75 ± 4.13 | 92.53 ± 1.09 |
| Muscle | 0.16 ± 0.06 | 0.05 ± 0.02 | 0.01 ± 0.01 | 0.0 ± 0.00 | 0.01 ± 0.01 | 0.00 ± 0.00 | 0.00 ± 0.00 |
| Feces | — | — | — | — | 6.10 ± 2.60 | 5.89 ± 3.81 | 6.23 ± 1.00 |
| Pancreas | 10.26 ± 1.44 | 7.37 ± 1.20 | 3.49 ± 2.15 | 3.28 ± 0.80 | 1.19 ± 0.49 | 0.17 ± 0.09 | 0.06 ± 0.02 |
| Carcass | 33.06 ± 5.51 | 12.31 ± 3.27 | 13.55 ± 6.05 | 2.92 ± 0.64 | 1.69 ± 0.56 | 0.57 ± 0.02 | 0.38 ± 0.06 |
| Tumor | 1.92 ± 1.22 | 0.99 ± 0.62 | 0.36 ± 0.32 | 0.18 ± 0.17 | 0.25 ± 0.13 | 0.08 ± 0.05 | 0.03 ± 0.01 |

TABLE 12

$^{90}$Y-DOTA-8-Aoc-BBN[7–14]NH$_2$ biodistribution
(Avg % ID/gm, n = 5) in PC-3 tumor bearing mice.

| Tissue | Time | | | | |
|---|---|---|---|---|---|
| | 1 hr (n = 9) | 4 hrs (n = 9) | 24 hrs (n = 6) | 48 hrs (n = 6) | 72 hrs (n = 6) |
| Blood | 0.34 ± 0.12 | 0.05 ± 0.07 | 0.07 ± 0.08 | 0.06 ± 0.08 | 0.06 ± 0.09 |
| Heart | 0.10 ± 0.11 | 0.10 ± 0.14 | 0.00 ± 0.00 | 0.14 ± 0.19 | 0.36 ± 0.45 |
| Lung | 0.22 ± 0.12 | 0.07 ± 0.07 | 0.01 ± 0.02 | 0.03 ± 0.03 | 0.02 ± 0.03 |
| Liver | 0.39 ± 0.29 | 0.18 ± 0.12 | 0.08 ± 0.03 | 0.03 ± 0.03 | 0.08 ± 0.11 |
| Spleen | 1.09 ± 0.67 | 0.35 ± 0.42 | 0.11 ± 0.13 | 0.09 ± 0.24 | 0.28 ± 0.26 |
| Stomach | 1.34 ± 0.64 | 0.55 ± 0.16 | 0.09 ± 0.07 | 0.04 ± 0.07 | 0.07 ± 0.03 |
| L. Intestine | 3.35 ± 1.12 | 5.17 ± 1.85 | 1.27 ± 0.92 | 0.77 ± 0.15 | 0.47 ± 0.24 |
| S. Intestine | 3.64 ± 0.82 | 1.66 ± 0.91 | 0.35 ± 0.16 | 0.13 ± 0.04 | 0.08 ± 0.05 |
| Kidney | 3.77 ± 1.41 | 1.68 ± 0.76 | 0.51 ± 0.25 | 0.29 ± 0.12 | 0.43 ± 0.29 |
| Muscle | 0.15 ± 0.19 | 0.07 ± 0.13 | 0.02 ± 0.03 | 0.07 ± 0.13 | 0.08 ± 0.19 |
| Pancreas | 24.73 ± 4.97 | 14.02 ± 4.89 | 1.80 ± 0.57 | 0.59 ± 0.14 | 0.27 ± 0.17 |
| Tumor | 2.95 ± 0.99 | 1.98 ± 0.66 | 1.08 ± 0.37 | 0.58 ± 0.30 | 0.46 ± 0.48 |

TABLE 13

$^{90}$Y-DOTA-8-Aoc-BBN[7–14]NH$_2$ biodistribution
(Avg % ID) in PC-3 tumor bearing mice.

| Tissue | Time | | | | |
|---|---|---|---|---|---|
| | 1 hr (n = 9) | 4 hrs (n = 9) | 24 hrs (n = 6) | 48 hrs (n = 6) | 72 hrs (n = 6) |
| Blood | 0.56 ± 0.20 | 0.09 ± 0.13 | 0.12 ± 0.14 | 0.10 ± 0.14 | 0.11 ± 0.15 |
| Heart | 0.01 ± 0.01 | 0.01 ± 0.01 | 0.00 ± 0.00 | 0.02 ± 0.02 | 0.04 ± 0.04 |
| Lung | 0.06 ± 0.03 | 0.01 ± 0.01 | 0.00 ± 0.00 | 0.01 ± 0.01 | 0.00 ± 0.01 |
| Liver | 0.44 ± 0.34 | 0.19 ± 0.13 | 0.10 ± 0.03 | 0.04 ± 0.04 | 0.08 ± 0.11 |
| Spleen | 0.07 ± 0.04 | 0.02 ± 0.03 | 0.01 ± 0.01 | 0.01 ± 0.02 | 0.02 ± 0.01 |
| Stomach | 0.41 ± 0.12 | 0.18 ± 0.06 | 0.04 ± 0.04 | 0.01 ± 0.02 | 0.04 ± 0.02 |
| L. Intestine | 2.44 ± 0.66 | 3.33 ± 0.71 | 1.11 ± 0.75 | 0.47 ± 0.12 | 0.35 ± 0.20 |
| S. Intestine | 4.65 ± 0.98 | 2.06 ± 1.27 | 0.51 ± 0.20 | 0.16 ± 0.06 | 0.11 ± 0.07 |
| Kidney | 1.22 ± 0.46 | 0.54 ± 0.25 | 0.17 ± 0.09 | 0.10 ± 0.04 | 0.13 ± 0.07 |
| Urine | 57.73 ± 14.52 | 67.02 ± 16.74 | 67.62 ± 17.26 | 76.74 ± 21.06 | 82.97 ± 25.39 |
| Muscle | 0.02 ± 0.02 | 0.01 ± 0.01 | 0.00 ± 0.01 | 0.01 ± 0.02 | 0.01 ± 0.02 |
| Feces | — | — | 10.71 ± 8.29 | 6.78 ± 3.88 | 13.89 ± 4.48 |
| Pancreas | 5.70 ± 1.60 | 3.42 ± 0.82 | 0.44 ± 0.08 | 0.15 ± 0.04 | 0.08 ± 0.05 |
| Carcass | 0.62 ± 0.44 | 0.14 ± 0.11 | 0.04 ± 0.04 | 0.11 ± 0.17 | 0.10 ± 0.11 |
| Tumor | 0.40 ± 0.22 | 0.34 ± 0.22 | 0.16 ± 0.09 | 0.11 ± 0.07 | 0.06 ± 0.06 |

TABLE 14

In Vivo Biodistribution Analyses (% ID/g (SD), n = 5) of $^{111}$In-DOTA-8-Aoc-BBN[7–14]NH$_2$ in Tumor-Bearing Mice Models (MDA-MB-231).

| Tissue/Organ | 1 hour | 4 hours | 24 hours |
|---|---|---|---|
| Blood | 0.35 ± 0.08 | 0.08 ± 0.10 | 0.02 ± 0.03 |
| Heart | 0.15 ± 0.11 | 0.03 ± 0.05 | 0.08 ± 0.06 |
| Lung | 0.31 ± 0.09 | 0.06 ± 0.06 | 0.05 ± 0.05 |
| Liver | 0.31 ± 0.04 | 0.15 ± 0.09 | 0.07 ± 0.02 |
| Spleen | 0.57 ± 0.10 | 0.48 ± 0.25 | 0.21 ± 0.07 |
| Stomach | 1.49 ± 0.68 | 0.27 ± 0.08 | 0.33 ± 0.10 |
| L. Intestine | 5.14 ± 0.42 | 5.58 ± 1.26 | 2.76 ± 0.49 |
| S. Intestine | 5.15 ± 0.19 | 1.52 ± 0.19 | 0.90 ± 0.14 |
| Kidney | 3.29 ± 0.56 | 1.76 ± 0.15 | 0.98 ± 0.28 |
| Pancreas | 23.4 ± 4.99 | 17.9 ± 5.00 | 5.06 ± 0.77 |
| Muscle | 0.08 ± 0.05 | 0.06 ± 0.13 | 0.03 ± 0.05 |
| Tumor 1 | 0.91 ± 0.16 | 0.36 ± 0.13 | 0.22 ± 0.07 |
| Tumor 2 | 0.74 ± 0.27 | 0.40 ± 0.23 | 0.24 ± 0.15 |
| Urine (% ID) | 72.1 ± 3.55 | 84.3 ± 2.09 | 83.8 ± 1.41 |

TABLE 15

$^{149}$Pm-DOTA-SPACER-BBN[7–14]NH$_2$ biodistribution (Avg % ID/gm, n = 5) in CF1 normal mice after 1 hour post-injection.

| Tissue | Spacer | | | |
|---|---|---|---|---|
| | 0 | β-Ala | 5-Ava | 8-Aoc |
| Blood | 0.00 ± 0.00 | 0.21 ± 0.22 | 0.27 ± 0.06 | 0.12 ± 0.13 |
| Heart | 0.00 ± 0.00 | 0.17 ± 0.24 | 0.42 ± 0.59 | 0.03 ± 0.06 |
| Lung | 0.00 ± 0.00 | 0.34 ± 0.30 | 0.78 ± 1.08 | 0.09 ± 0.14 |
| Liver | 0.12 ± 0.10 | 0.15 ± 0.05 | 0.23 ± 0.13 | 0.19 ± 0.12 |
| Spleen | 0.00 ± 0.00 | 0.16 ± 0.31 | 2.37 ± 1.36 | 1.61 ± 0.36 |
| Stomach | 0.04 ± 0.08 | 0.19 ± 0.11 | 1.90 ± 1.60 | 1.16 ± 0.59 |
| L. Intestine | 0.01 ± 0.03 | 0.42 ± 0.08 | 3.53 ± 1.10 | 4.14 ± 2.14 |
| S. Intestine | 0.27 ± 0.17 | 0.63 ± 0.20 | 5.15 ± 1.20 | 12.56 ± 16.70 |
| Kidney | 1.04 ± 0.90 | 2.05 ± 1.63 | 2.81 ± 0.66 | 3.74 ± 1.02 |
| Muscle | 0.00 ± 0.00 | 0.04 ± 0.10 | 0.24 ± 0.25 | 0.09 ± 0.21 |
| Pancreas | 0.00 ± 0.00 | 2.40 ± 1.33 | 22.1 ± 5.40 | 28.29 ± 13.26 |

TABLE 16

$^{149}$Pm-DOTA-SPACER-BBN[7–14]NH$_2$ biodistribution (Avg % ID, n = 5) in CF1 normal mice after 1 hour post-injection.

| Spacer Tissue | 0 | β-Ala | 5-Ava | 8-Aoc |
|---|---|---|---|---|
| Blood | 0.00 ± 0.00 | 0.30 ± 0.32 | 0.47 ± 0.11 | 0.23 ± 0.26 |
| Heart | 0.00 ± 0.00 | 0.02 ± 0.02 | 0.06 ± 0.09 | 0.00 ± 0.01 |
| Lung | 0.00 ± 0.00 | 0.06 ± 0.04 | 0.17 ± 0.21 | 0.02 ± 0.04 |
| Liver | 0.16 ± 0.15 | 0.23 ± 0.07 | 0.37 ± 0.20 | 0.35 ± 0.20 |
| Spleen | 0.00 ± 0.00 | 0.02 ± 0.04 | 0.27 ± 0.13 | 0.24 ± 0.06 |
| Stomach | 0.02 ± 0.05 | 0.10 ± 0.03 | 0.77 ± 0.74 | 0.66 ± 0.35 |
| L. Intestine | 0.01 ± 0.02 | 0.31 ± 0.06 | 3.18 ± 1.18 | 4.43 ± 2.37 |
| S. Intestine | 0.38 ± 0.25 | 0.95 ± 0.19 | 7.70 ± 0.66 | 7.84 ± 2.15 |
| Kidney | 0.34 ± 0.28 | 0.61 ± 0.41 | 1.11 ± 0.29 | 1.55 ± 0.47 |
| Urine | 97.10 ± 2.91 | 95.54 ± 1.15 | 75.82 ± 2.02 | 67.20 ± 5.53 |
| Muscle | 0.00 ± 0.00 | 0.00 ± 0.01 | 0.03 ± 0.04 | 0.01 ± 0.02 |
| Pancreas | 0.07 ± 0.01 | 0.46 ± 0.23 | 4.25 ± 0.43 | 7.34 ± 3.51 |
| Carcass | 1.98 ± 2.27 | 1.64 ± 0.38 | 6.16 ± 0.75 | 10.30 ± 1.84 |

TABLE 17

$^{177}$Lu-DOTA-SPACER-BBN[7–14]NH$_2$ biodistribution (Avg % ID/gm, n = 5) in CF1 normal mice after 1 hour post-injection

| Spacer Tissue | 0 | β-Ala | 5-Ava | 8-Aoc | 11-Aun |
|---|---|---|---|---|---|
| Blood | 0.58 ± 0.96 | 0.16 ± 0.17 | 0.22 ± 0.19 | 0.14 ± 0.10 | 0.78 ± 1.10 |
| Heart | 0.04 ± 0.09 | 0.43 ± 0.70 | 0.34 ± 0.35 | 0.19 ± 0.36 | 1.56 ± 2.40 |
| Lung | 0.19 ± 0.26 | 0.23 ± 0.33 | 0.47 ± 0.84 | 0.20 ± 0.21 | 0.73 ± 0.81 |
| Liver | 0.09 ± 0.06 | 0.15 ± 0.06 | 0.09 ± 0.04 | 0.23 ± 0.05 | 1.65 ± 0.29 |
| Spleen | 0.04 ± 0.09 | 0.31 ± 0.31 | 1.26 ± 0.69 | 1.23 ± 0.59 | 1.78 ± 1.87 |
| Stomach | 0.10 ± 0.21 | 0.34 ± 0.18 | 1.48 ± 2.25 | 1.41 ± 0.44 | 1.82 ± 1.12 |
| L. Intestine | 0.07 ± 0.09 | 0.45 ± 0.19 | 3.78 ± 1.23 | 6.17 ± 0.79 | 6.31 ± 0.86 |
| S. Intestine | 0.75 ± 0.60 | 0.49 ± 0.10 | 2.55 ± 1.31 | 6.47 ± 1.24 | 12.58 ± 1.73 |
| Kidney | 1.21 ± 0.31 | 1.88 ± 0.37 | 2.03 ± 1.02 | 4.97 ± 0.71 | 4.97 ± 0.61 |
| Muscle | 0.09 ± 0.15 | 0.94 ± 1.54 | 0.67 ± 0.90 | 0.17 ± 0.39 | 0.75 ± 1.12 |
| Pancreas | 0.18 ± 0.28 | 1.44 ± 0.26 | 16.41 ± 1.38 | 30.83 ± 1.89 | 35.48 ± 2.39 |

TABLE 18

$^{177}$Lu-DOTA-SPACER-BBN[7–14]NH$_2$ biodistribution (Avg % ID, n = 5) in CF1 normal mice after 1 hour post-injection.

| Spacer Tissue | 0 | β-Ala | 5-Ava | 8-Aoc | 11-Aun |
|---|---|---|---|---|---|
| Blood | 0.39 ± 0.34 | 0.24 ± 0.25 | 0.35 ± 0.31 | 0.20 ± 0.15 | 0.47 ± 0.54 |
| Heart | 0.01 ± 0.02 | 0.05 ± 0.08 | 0.04 ± 0.05 | 0.02 ± 0.04 | 0.19 ± 0.29 |
| Lung | 0.04 ± 0.06 | 0.04 ± 0.06 | 0.08 ± 0.15 | 0.03 ± 0.04 | 0.17 ± 0.22 |
| Liver | 0.19 ± 0.10 | 0.21 ± 0.09 | 0.14 ± 0.06 | 0.31 ± 0.05 | 2.26 ± 0.46 |
| Spleen | 0.01 ± 0.01 | 0.05 ± 0.04 | 0.18 ± 0.12 | 0.16 ± 0.05 | 0.24 ± 0.24 |
| Stomach | 0.05 ± 0.11 | 0.13 ± 0.09 | 0.73 ± 1.33 | 0.51 ± 0.15 | 0.64 ± 0.35 |
| L. Intestine | 0.09 ± 0.12 | 0.36 ± 0.17 | 3.52 ± 1.37 | 4.63 ± 0.57 | 5.03 ± 0.46 |
| S. Intestine | 1.27 ± 1.03 | 0.64 ± 0.20 | 3.80 ± 1.87 | 9.55 ± 2.37 | 17.10 ± 3.60 |
| Kidney | 0.58 ± 0.10 | 0.63 ± 0.14 | 0.69 ± 0.33 | 1.62 ± 0.14 | 1.76 ± 0.25 |
| Urine | 93.26 ± 3.61 | 94.66 ± 1.88 | 84.08 ± 2.13 | 71.16 ± 1.05 | 58.76 ± 3.44 |
| Muscle | 0.02 ± 0.03 | 0.11 ± 0.18 | 0.09 ± 0.12 | 0.02 ± 0.05 | 0.11 ± 0.18 |
| Pancreas | 0.06 ± 0.10 | 0.32 ± 0.07 | 3.78 ± 1.09 | 7.01 ± 1.42 | 6.89 ± 1.20 |
| Carcass | 4.34 ± 2.64 | 2.73 ± 1.08 | 2.77 ± 0.75 | 4.95 ± 1.41 | 6.69 ± 2.48 |

TABLE 19

$^{177}$Lu-DOTA-8-Aoc-BBN[7–14]NH$_2$ biodistribution (Avg % ID/gm, n = 5) in PC-3 tumor bearing

| | Time | | |
|---|---|---|---|
| Tissue | 1 hr (n = 5) | 4 hrs (n = 5) | 24 hrs (n = 5) |
| Blood | 0.38 ± 0.22 | 0.08 ± 0.07 | 0.01 ± 0.01 |
| Heart | 0.15 ± 0.22 | 0.07 ± 0.13 | 0.06 ± 0.99 |
| Lung | 0.18 ± 0.09 | 0.11 ± 0.15 | 0.14 ± 0.26 |
| Liver | 0.30 ± 0.05 | 0.13 ± 0.02 | 0.03 ± 0.02 |
| Spleen | 0.33 ± 0.51 | 0.60 ± 0.36 | 0.08 ± 0.10 |
| Stomach | 1.38 ± 0.52 | 0.34 ± 0.34 | 0.19 ± 0.13 |
| L. Intestine | 3.29 ± 0.61 | 7.29 ± 3.73 | 1.90 ± 0.53 |
| S. Intestine | 5.60 ± 0.46 | 1.93 ± 0.96 | 0.48 ± 0.14 |
| Kidney | 4.70 ± 0.95 | 2.18 ± 0.31 | 0.60 ± 0.20 |
| Muscle | 0.11 ± 0.13 | 0.15 ± 0.21 | 0.10 ± 0.17 |
| Pancreas | 38.53 ± 3.61 | 22.18 ± 4.66 | 4.97 ± 2.28 |
| Tumor | 4.22 ± 1.09 | 3.03 ± 0.91 | 1.54 ± 1.14 |

TABLE 20

$^{177}$Lu-DOTA-8-Aoc-BBN[7–14]NH$_2$ biodistribution (Avg % ID, n = 5) in PC-3 tumor bearing mice.

| | Time | | |
|---|---|---|---|
| Tissue | 1 hr (n = 5) | 4 hrs (n = 5) | 24 hrs (n = 5) |
| Blood | 0.62 ± 0.44 | 0.12 ± 0.11 | 0.01 ± 0.02 |
| Heart | 0.01 ± 0.02 | 0.01 ± 0.02 | 0.01 ± 0.01 |
| Lung | 0.04 ± 0.02 | 0.05 ± 0.09 | 0.03 ± 0.05 |
| Liver | 0.38 ± 0.09 | 0.15 ± 0.03 | 0.04 ± 0.03 |
| Spleen | 0.03 ± 0.04 | 0.05 ± 0.02 | 0.01 ± 0.01 |
| Stomach | 0.61 ± 0.09 | 0.22 ± 0.06 | 0.09 ± 0.06 |
| L. Intestine | 3.64 ± 0.72 | 7.28 ± 4.23 | 1.75 ± 0.23 |
| S. Intestine | 8.20 ± 1.72 | 2.51 ± 0.75 | 0.67 ± 0.12 |
| Kidney | 1.35 ± 0.41 | 0.61 ± 0.08 | 0.17 ± 0.06 |
| Urine | 67.41 ± 2.45 | 79.76 ± 6.48 | 85.85 ± 1.39 |
| Muscle | 0.01 ± 0.02 | 0.02 ± 0.03 | 0.02 ± 0.03 |
| Pancreas | 9.70 ± 1.12 | 5.23 ± 1.68 | 1.31 ± 0.45 |
| Tumor | 1.15 ± 0.72 | 0.78 ± 0.27 | 0.29 ± 0.18 |
| Carcass | 6.18 ± 1.01 | 2.52 ± 1.18 | 2.08 ± 3.14 |

REFERENCES CITED

Albert et al., (1991) Labeled Polypeptide Derivatives, Int'l Patent No. W091/01144.

Bjisterbosch, M. K., et al., (1995) Quarterly J. Nucl. Med. 39:4–19.

Bushbaum, (1995) Pharmacokinetics of Antibodies and Their Radiolabels. In: Cancer Therapy with Radiolabeled Antibodies, (ed) D. M. Goldenberg, CRC Press, Boca Raton, Chaper 10, 115–140 FL.

Cai et al., (1992) Peptides, 13:267.

Cai et al., (1994) Proc. Natl. Acad. Sci., 91:12664.

Coy et al., (1988) J. Biolog. Chem., 263(11), 5066.

Cutler, C., Hu, F., Hoffman, T. J., Volkert, W. A., and Jurisson, S. S., "DOTA Bombesin Complexes with Sm-153 and NCA PM-149", The International Chemical Congress of Pacific Basin Societies, Pacifichem 2000,, Honolulu, HI, December, 2000.

Davis et al. (1992) Peptides, 13:401.

de Jong et al., (1997) Eur. J. Nucl. Med., 24:368.

Duncan et al., (1997) Cancer Res. 57:659.

Eckelman (1995) Eur. J. Nucl. Med., 22:249.

Eckelman et al., (1993) The design of site-directed radiopharmaceuticals for use in drug discovery. In: Nuclear Imaging in Drug Discovery, Development and Approval (eds) H.D. Burns et al., Birkhauser Publ. Inc., Boston, Mass.

Fischman etal., (1993) J. Nucl. Med., 33:2253.

Fritzberg et al., (1992) J. Nucl. Med., 33:394.

Frizberg et al. (1995) Radiolabeling of antibodies for targeted diagnostics. In: Targeted Delivery of Imaging Agents (ed) V.P. Torchilin, CRC Press, Boca Raton, Fla., pp. 84–101.

Gali, H., Hoffman, T. J., Owen, N. K., Sieckman, G. L., and Volkert, W. A., "In Vitro and In Vivo Evaluation of 111In_Labeled DOTA_8_AocBBN[7–14]NH2 Conjugate for Specific Targeting of Tumors Expressing Gastrin Releasing Peptide (GRP) Receptors", 47th Annual Meeting - Society of Nuclear Medicine, St. Louis, Mo., J.Nucl. Med., 41 (5), 119P, #471, 2000.

Gali, H., Hoffman, T. J., Sieckman, G. L., Katti, K. V., and Volkert, W. A., "Synthesis, Characterization and Labeling with 99mTc/188Re of Peptide Conjugates Containing a Dithio-bisphosphine Chelating Agent" Bioconjugate Chemistry (Accepted), 2001.

Gali, H., Hoffman, T. J., Sieckman, G. L., Katti, K. V., and Volkert, W. A. "Synthesis, Characterization, and Labeling with 99mTc/l 88Re of Peptide Conjugates Containing a Dithio-bisphosphine Chelating Agent", American Chemical Society Annual Meeting, San Francisco, Calif., April, 2000.

Gali, H., Smith, C. J., Hoffman, T. J., Sieckman, G. L., Hayes, D. L., Owen, N.K., and Volkert, W. A., "Influence of the Radiometal on the In Vivo Pharmacokinetic Properties of a Radiometal-labeled DOTA-Conjugated Peptide", 222nd American Chemical Society National Meeting, Chicago, Ill., August, 2001 (Accepted)

Hennanson (1996) In: Bioconjugate Techniques, Academic Press, pp. 3–136.

Hoffken, (ed) (1994) Peptidesin Oncology II, Springer-Vedag, Berlin-Heidelberg.

Hoffman, et al., (1997) Quarterly J. Nucl. Med. 41(2) Supp. #1, 5.

Hoffman, T. J. and Volkert, W. A. "Design of Radioloabeled Bombesin Analogs" Receptors 2000; DOE Sponsored Workshop (La Jolla, Calif.) Apr. 17–18, 2000.

Hoffman, T. J., Gali, H., Sieckman, G. L., Forte, L. R., Chin, D. T., Owen, N. K., Wooldridge, J. E., and Volkert, W. A., "Development and Characterization of a Receptor-Avid 111 In-Labeled Peptide for Site-Specific Targeting of Colon Cancer", 92nd Annual Meeting of the American Association for Cancer Research, New Orleans, La. Proceedings of the American Association for Cancer Research, Vol. 42, 139, #746, March 2001.

Hoffman, T. J., Li, N., Sieckman, G., and Volkert, W. A., "Uptake and Retention of a Rh-105 Labeled Bombesin Analogue in GRP Receptor Expressing Neoplasms: An In-Vitro Study", 44th Annual Meeting - Society of Nuclear Medicine, June, 1997;J.Nucl. Med., 38(5), 188P, 1997.

Hoffman, T. J., Li, N., Sieckman, G., Higginbotham, C. A., and Volkert, W. A., "Evaluation of Radiolabeled (1–125 vs. Rh-1 05) Bombesin Analogue Internalization in Normal and Tumor Cell Lines", 10th International Symposium on Radiopharmacology, May, 1997; Quarterly J. Nuel. Med., 41(2) Suppl#1, 5,1997.

Hoffman, T. J., Li, N., Volkert, W. A., Sieckman, G., Higginbotham, C. A., and Ochrymowycz, L. A., "Synthesis and Characterization of Rh-105 Labeled Bombesin Analogues: Enhancement of GRP Receptor Binding Affinity Utilizing Aliphatic Carbon Chain Linkers", J. Label. Comp'd Radiopharm., 1997.

Hoffman, T. J., Li, N., Volkert, W. A., Sieckman, G., Higginbotham, C. A., and Ochrymowycz, L. A., "Synthesis and Characterization of Rh-105 Labeled Bombesin Analogues: Enhancement of GRP Receptor Binding Affinity Utilizing Aliphatic Carbon Chain Linkers", 12th International Symposium on Radiopharmaceutical Chemistry, June, 1997.

Hoffman, T. J., Li, N., Higginbotham, C. A., Sieckman, G., Volkert, W. A., "Specific Uptake and Retention of Rh-105 Labeled Bombesin Analogues in GRP-Receptor Expressing Cells", European Society of Nuclear Medicine, August, 1997; Eur. J. Nucl. Med., 24(8), 901, 1997.

Hoffman, T. J., Li, N., Sieckman, G. L., Higginbotham, C. Ochrymowycz, L. A., Volkert, W. A. "Rh-105 Bombesin Analogs: Selective in Vivo Targeting of Prostate Cancer with a Therapeutic Radionuclide", 45th Annual Meeting - Society of Nuclear Medicine, June 1998; J.Nucl. Med., 39(5), 222P, 1998.

Hoffman, T. J., Quinn, T. P., and Volkert, W. A., "Radiometallated Receptor-Avid Peptide Conjugates for Specific In Vivo Targeting of Cancer", Nuc. Med. & Biol. (Accepted), 2001.

Hoffman, T. J., Sieckman, G., Volkert, W. A., "Targeting Small Cell Lung Cancer Using Iodinated Peptide Analogs", J. Label. Comp'd Radiopharm., 37:321–323, 1995.

Hoffman, T. J., Sieckman, G., Volkert, W. A., "Targeting Small Cell Lung Cancer Using Iodinated Peptide Analogs", 11th International Symposium on Radiopharmaceutical Chemistry, August, 1995; J. Label. Comp'd Radiopharm., 37:321–323,1995.

Hoffman, T. J., Sieckman, G. L:, Volkert, W. A., "Iodinated Bombesin Analogs: Effect of N-Terminal Chain Iodine Attachment on BBN/GRP Receptor Binding", 43rd Annual Meeting - Society of Nuclear Medicine, June, 1996; J.Nucl. Med., 37(5), p185P, 1996.

Hoffman, T. J., Simpson, S. D., Smith, C. J., Sieckman, G. L., Higginbotham, C., Volkert, W. and Thornback, J. R. "Accumulation and Retention of 99mTc-RP527 by GRP Receptor Expressing Tumors in SCID Mice", 46th Annual Meeting - Society of Nuclear Medicine, Los Angeles, Calif., J.Nucl. Med., 40(5), 104P, 1999.

Hoffman, T. J., Simpson, S. D., Smith, C. J., Sieckman, G. L., Higginbotham, C., Eshima, D., Volkert, W. and Thornback, J. R. "Accumulation and Retention of 99mTc-RP591 by GRP Receptor Expressing Tumors in SCID Mice", Congress of the European Association of Nuclear Medicine, Barcelona, Spain, Eur. J. Nucl. Med., 26(9), 1157, #PS-420, September, 1999.

Hoffman, T. J., Smith, C. J., Gali, H., Owen, N. K., Sieckman, and Volkert, W. A., "In Vitro and In Vivo Evaluation of 111 In/90Y Radiolabeled Peptides for Specific Targeting of Tumors Expressing Gastrin Releasing Peptide (GRP) Receptors", 92nd Annual Meeting of the American Association for Cancer Research, New Orleans, La. Proceedings of the American Association for Cancer Research, Vol.42, 773, #4148, March 2001.

Hoffman, T. J., Smith, C. J., Gali, H., Owen, N. K., Sieckman, Hayes, D. L., and Volkert, W. A., "Development of a Diagnostic Radiopharmaceutical for Visualization of Primary and Metastatic Breast Cancer", 48th Annual Meeting-Society of Nuclear Medicine, Toronto, Ontario, Canada, June 2001. (Accepted)

Hoffman, T. J., Smith, C. J., Gali, H., Owen, N. K., Sieckman, Hayes, D. L., Foster, B., and Volkert, W. A., "111 In/9OY Radiolabeled Peptides for Targeting Prostate Cancer; A Matched Pair Gastrin Releasing Peptide (GRP) Receptor Localizing Radiopharmaceutical", 48th Annual Meeting-Society of Nuclear Medicine, Toronto, Ontario, Canada, June 2001. (Accepted)

Hoffman, T. J., Smith, C. J., Sieckman, G. L., Owen, N. K., and Volkert, W. A., "Design, Synthesis, and Biological Evaluation of Novel Gastrin Releasing Peptide Receptor Targeting Radiopharmaceuticals" American Chemical Society Annual Meeting, August 2000, Washington, D.C.

Hoffman, T. J., Smith, C. J., Simpson, S. D., Sieckman, G. L., Higginbotham, C., Jimenez, H., Eshima, D., Thornback, J. R., and Volkert, W. A. "Targeting Gastrin Releasing Peptide Receptor (GRP-R) Expression in Prostate and Pancreatic Cancer Using Radiolabeled GRP Agonist Peptide Vectors", American Association for Cancer Research Annual Meeting, San Francisco, Calif., Proceedings of the American Association for Cancer Research, Vol.41, 529, #3374, April, 2000.

Hoffman, T. J., Smith, C. J., Simpson, S. D., Sieckman, G. L., Higginbothan, C., Jimenez, H., Eshima, D., Thornback, J. R., and Volkert, W. A., "Optimizing Pharmacokinetics of Tc-99m-GRP Receptor Targeting Peptides Using Multi-Amino Acid Linking Groups", 47th Annual Meeting - Society of Nuclear Medicine, St. Louis, Mo., J.Nucl, Med., 41(5), 228P, #1013, 2000.

Jensen et al., (1993) Rec. Result. Cancer Res., 129:87.

Karra, S. R., Schibli, R., Gali, H., Katti, K. V., Hoffman, T. J., Higginbotham, C., Sieckman, G., Volkert, W. A., "99mTc-Labeling and In Vivo Studies of a Bombesin Analogue with a Novel Water-soluble Dithia-Diphosphine Based Bifunctional Chelating Agent", Bioconjugate Chemistry, 10:254–260,1999.

Katti, K. V, Gali, H., Schibli, R., Hoffman, T. J., and Volkert, W. A. "99mTc/Re Coordination Chemistry and Biomolecule Conjugation Strategy of a Novel Water Soluble Phosphine-Based Bifunctional Chelating Agent", Fifth International Symposium of Technetium in Chemistry and Nuclear Medicine, Bressanone, Italy, September, 1998.

Katti, K. V., Gali, H., Schibli, R., Hoffman, T. J., and Volkert, W. A. "99mTc/Re Coordination Chemistry and Biomolecule Conjugation Strategy of a Novel Water Soluble Phosphine-Based Bifunctional Chelating Agent", In Technetium, Rhenium and Other Metals in Chemistry and Nuclear Medicine (5), Ed. By M. Nicolini and U. Mazzi, Servizi Grafici Editoriali, Padova, pp. 93–100,1999.

Kothari, K. K., Katti, K. V., Prabhu, K. R., Gali, H., Pillarsetty, N. K., Hoffman, T. J., Owen, N. K., and Volkert, W. A., "Development of a Diamido-Diphosphine (N2P2)-BFCA for Labeling Cancer Seeking Peptides via the 99mTc(l)(CO)3(H20)3 Intermediate", 47th Annual Meeting - Society of Nuclear Medicine, St. Louis, Mo., J.Nucl. Med., 41 (5), 244P, #1079, 2000. Krenning et al., (1994) Semin. Oncology, 5–14.

Leban et al. (1994) J. Med. Chem., 37:439.

Li et al., (1996a) J. Nucl. Med., 37:61 P.

Li et al., (1996b) Radiochim Acta, 75:83.

Li, W. P., Ma, D. S., Higginbotham, C., Hoffman, T. J., Ketring, A. R., and Jurisson, S. S., "Development of an In Vitro Model for Assessing the In Vivo Stability of Lanthanide Chelates", Nuc. Med. & Biol. 28:145–154, 2001.

Lister-James et al. (1997) Quart. J. Nucl. Med., 41:111.

Lowbertz et al., (1994) Semin. Oncol., 1–5.

Mattes, (1995) Pharmacokinetics of antibodies and their radiolabels. In: Cancer Therapy with Radiolabeled Antibodies (ed) D.M. Goldenberg, CRC Press, Boca Raton, Fla.

Moody et al., (1995) Life Sciences, 56(7), 521.

Moody et al., (1996) Peptides, 17(8), 1337.

Ning, Li, Hoffman, T. J., Sieckman, G. L., Ochrymowycz, L. A., Higginbotham, C., Struttman, M., Volkert, W. A., and Ketring, A. R., "In-vitro and In-vivo Characterization of a Rh-105-tetrathiamacrocycle Conjugate of a Bombesin Analogue",43rd Annual Meeting - Society of Nuclear Medicine, June, 1996; J.Nucl. Med., 37(5), p61 P, 1996.

Parker (1990) Chem. Soc. Rev., 19:271.

Pollak et al., (1996) Peptide Derived Radionuclide Chealtors, Int'l Patent No. WO96/03427.

Qin etal., (1994) J. Canc. Res. Clin. Oncol., 120:519.

Qin, Y. et al., (1994) Cancer Research 54: 1035–1041.

Reile, H. et al., (1994) Prostate 25: 29–38.

Schibli, R., Karra, S., Katti, K. V., Gali, H., Higginbotham, C., Sieckman, G., Hoffman, T. J., Volkert, W. A., "A Tc-99m-Dithia-Di(Bis-Hydroxy-methylene)Phosphine Conjugate of Bombesin: In Vitro and In Vivo Studies" 45th Annual Meeting - Society of Nuclear Medicine, June, 1998; J.Nucl. Med., 39(5), 225P, 1998.

Schibli, R., Karra, S. R., Gali, H., Katti, K. V., Higginbotham, C., Smith, C. J., Hoffman, T. J., and Volkert, W. A. "Conjugation of Small Biomolecules and Peptides with Water-Soluble Dithio-Bis-Hydroxymethylphosphine Ligands", Annual Meeting of the American Chemical Society, April, 1998.

Schubiger et al., (1996) Bioconj. Chem.

Seifert et al. (1998) Appl. Radiat. Isot., 49:5.

Smith et al., (1997) Nucl. Med. Biol., 24:685.

Smith, C. J., Hoffman, T. J., Gali, H., Hayes, D. L., Owen, N. K., Sieckman, G. L., and Volkert, W. A., "Radiochemical Investigations of 177Lu-DOTA-8-Aoc-BBN(7–14) NH2: A New Gastrin Releasing Peptide Receptor (GRPr) Targeting Radiopharmaceutical", J. Labeled Compounds and Radiopharmaceuticals (Accepted), 2001

Smith, C. J., Hoffman, T. J., Gali, H., Hayes, D. L., Owen, N. K., Sieckman, G. L., and Volkert, W. A., "Radiochemical Investigations of 177Lu-DOTA-8-Aoc-BBN[7–14) NH2: A New Gastrin Releasing Peptide Receptor (GRPr) Targeting Radiopharmaceutical", 14th International Symposium on Radiopharmaceutical Chemistry, Interlaken Switzerland, June, 2001, J. Labeled Compounds and Radiopharmaceuticals (Accepted)

Smythe, E. et al., (1991) Eur. J. Biochem. 202: 689–699.

Troutner(1987) Nucl. Med. Biol., 14:171.

Vallabhajosula et al., (1996) J. Nucl. Med., 37:1016.

Volkert, W. A., and Hoffman, T. J. "Design and Development of Receptor-avid Peptide Conjugates for In Vivo Targeting of Cancer", In Biomedical Imaging: Reporters, Dyes, and Instrumentation, Ed. by D. J. Bornhop, C. H. Contag, and E. M. Sevick_Muraca, Proceedings of SPIE Vol. 3600, 86–98,1999.

Volkert, W. A., Gali, H-P, Hoffman, T. J., Owen, N. K., Sieckman, G. L., and Smith, C. J., "111In/90Y Labeled GRP Analogs: A Structure-Activity Relationship", The International Chemical Congress of Pacific Basin Societies, Pacifichem 2000,, Honolulu, Hi., December, 2000.

Volkert, W. A., Hoffman, T. J., Li, N., Sieckman, G., Higginbotham, C., "Therapeutic Potential for Small Radiometallated Site-Specific Drugs", Radiation Research Society - Annual Meeting, May, 1997

Wilbur (1992) Bioconj. Chem., 3:433.

Wong, E. et al., (1997) Inorg. Chem. 36: 5799–5808.

Zhu, W–Y. et al., (1 991) Am. J. Physiol. 261: G57–64.

What is claimed is:

1. A compound comprising a metal complexed with a chelating group attached to a gastrin releasing peptide (GRP) receptor agonist, the gastrin releasing peptide receptor agonist including a bombesin agonist binding moiety, said compound having a structure of the formula X-Y-B wherein X is a metal chelating group, Y is a spacer group or covalent bond and B is a gastrin releasing peptide receptor agonist which includes a bombesin agonist binding moiety and Y is selected from the group consisting of at least one amino acid residue, a hydrocarbon chain and a combination thereof.

2. The compound of claim 1 wherein X is selected from the group consisting of DOTA, DTPA, S4, N3S, N2S2, NS3 and derivatives thereof.

3. The compound of claim 2, wherein Y is selected from the group consisting of at least one amino acid residue, a hydrocarbon chain and a combination thereof and B is selected from the group consisting of BBN(7–14) and BBN (8–14).

4. The compound of claim 2 wherein X is DOTA or a derivative thereof.

5. The compound of wherein 4 is selected is selected from the group consisting of at least one amino acid residue, a hydrocarbon chain and a combination thereof and B is selected from the group consisting of BBN(7–14) and BBN (8–14).

6. The compound of claim 5 wherein Y is a combination of L-glutamine and a hydrocarbon chain.

7. The compound of claim 6 wherein Y is a combination of L-glutamine and a C1 to C10 hydrocarbon chain.

8. The compound of claim 7 wherein Y is selected from the group consisting of glycine, β-alanine, gamma-aminobutanoic acid, 5-aminovaleric acid (5-Ava), 6-aminohexanoic acid, 7-aminoheptanoic acid, 8-aminooctanoic acid (8-Aoc), 9-aminononanoic acid, 10-aminodecanoic acid and 11-aminoundecanoic acid (11-Aun).

9. The compound of claim 2 wherein X is N3S or a derivative thereof.

10. The compound of claim 9 wherein Y is selected from the group consisting of at least one amino acid residue, a hydrocarbon chain and a combination thereof and B is selected from the group consisting of BBN(7–14) and BBN (8–14).

11. The compound of claim 10 wherein Y is gly-ser-gly.

12. A complex comprising a metal and a compound having a structure of the formula X-Y-B wherein X is a metal chelating group, Y is a spacer group or covalent bond and B is a gastrin releasing peptide (GRP) receptor agonist, the GRP receptor agonist including a bombesin agonist moiety and the metal is selected from the group consisting of transition metals, lanthanides, auger-electron emitting isotopes, and α-, β- or γ-emitting isotopes.

13. The complex of claim 12 wherein the metal is selected from the group consisting of: 105Rh-, 99mTc-, 186/188Re-, 153Sm-, 166Ho-, 111In-, 90Y-, 177Lu-, 149Pm-, 166Dy-, 175Yb-, 199Au- and 117mSn-.

14. The complex of claim 13 wherein X is selected from the group consisting of DOTA, DTPA, S4, N3S, N2S2, NS3 and derivatives thereof.

15. The complex of claim 14 wherein Y is selected from the group consisting of at least one amino acid residue, a hydrocarbon chain and a combination thereof and B is selected from the group consisting of BBN(7–14) and BBN (8–14).

16. The complex of claim 13 wherein X is DOTA or a derivative thereof.

17. The complex of claim 16 wherein Y is selected is selected from the group consisting of at least one amino acid residue, a hydrocarbon chain and a combination thereof and B is selected from the group consisting of BBN(7–14) and BBN(8–14).

18. The complex of claim 17 wherein Y is a combination of L-glutamine and a hydrocarbon chain.

19. The complex of claim 18 wherein Y is a combination of L-glutamine and a C1 to C10 hydrocarbon chain.

20. The complex of claim 19 wherein Y is selected from the group consisting of glycine, β-alanine, gamma-aminobutanoic acid, 5-aminovaleric acid (5-Ava), 6-aminohexanoic acid, 7-aminoheptanoic acid, 8-aminooctanoic acid (8-Aoc), 9-aminononanoic acid, 10-aminodecanoic acid and 11-aminoundecanoic acid (11-Aun).

21. The complex of claim 20 wherein Y is 8-aminooctanoic acid.

22. The complex of claim 20 consisting of 90Y-DOTA-8-Aoc-BBN(7–14)NH2.

23. The complex of claim 20 consisting of 111In-DOTA-8-Aoc-BBN(7–14) NH2.

24. The complex of claim 20 consisting of 177Lu-DOTA-8-Aoc-BBN(7–14) NH2.

25. The complex of claim 20 consisting of 149Pm-DOTA-8-Aoc-BBN(7–14) NH2.

26. The complex of claim 20 consisting of 90Y-DOTA-5-Ava-BBN(7–14)NH2.

27. The complex of claim 20 consisting of 111In-DOTA-5-Ava-BBN(7–14) NH2.

28. The complex of claim 20 consisting of 177Lu-DOTA-5-Ava-BBN(7–14) NH2.

29. The complex of claim 20 consisting of 149Pm-DOTA-5-Ava-BBN(7–14) NH2.

30. The complex of claim 13 wherein X is N3S or a derivative thereof.

31. The complex of claim 30 wherein Y is selected from the group consisting of at least one amino acid residue, a hydrocarbon chain and a combination thereof and B is selected from the group consisting of BBN(7–14) and BBN (8–14).

32. The complex of claim 31 wherein Y is gly-ser-gly.

33. The complex of claim 31 consisting of 99 mTc-N3S-gly-ser-gly-BBN(7–14)NH2.

34. A method of treating patients using radioisotope therapy by administering an effective amount of a pharmaceutical comprising a metal complex with a chelating group with a GRP receptor agonist, the GRP receptor agonist including a bombesin agonist moiety the complex comprising a metal and a compound having a structure of the formula X-Y-B wherein X is a metal chelating group, Y is a spacer group or covalent bond and B is a gastrin releasing peptide receptor agonist which includes a bombesin agonist binding moiety.

35. The method of claim 34 wherein the metal is selected from the group consisting of transition metals, lanthanides, auger-electron emitting isotopes, and α-, β- or γ-emitting isotopes.

36. The method of claim 34 wherein the metal is selected from the group consisting of: 105Rh-, 99mTc-, 186/188Re-, 153Sm-, 166Ho-, 111In-, 90Y-, 177Lu-, 149Pm-, 166Dy-, 175Yb-, 199Au- and 117mSn-.

37. The method of claim 36 wherein X is selected from the group consisting of DOTA, DTPA, S4, N3S, N2S2, NS3 and derivatives thereof.

38. The method of claim 37 wherein X is DOTA or a derivative thereof.

39. The method of claim 38 wherein Y is selected from the group consisting of at least one amino acid residue, a hydrocarbon chain and a combination thereof and B is selected from the group consisting of BBN(7–14) and BBN (8–14).

40. The method of claim 39 wherein Y is a combination of L-glutamine and a hydrocarbon chain.

41. The method of claim 40 wherein Y is selected from the group consisting of glycine, β-alanine, gamma-aminobutanoic acid, 5-aminovaleric acid (5-Ava), 6-aminohexanoic acid, 7-aminoheptanoic acid, 8-aminooctanoic acid (8-Aoc), 9-aminononanoic acid, 10-aminodecanoic acid and 11-aminoundecanoic acid (11-Aun).

42. A method of imaging a patient by administering to a subject a diagnostically effective amount of a compound as set forth in claim 1.

43. The method of claim 42, wherein said method includes administering an effective amount of a complex comprising a metal and a compound having a structure of the formula X-Y-B wherein X is a metal chelating group, Y is a spacer group or covalent bond and B is a gastrin releasing peptide receptor agonist which includes a bombesin agonist binding moiety.

44. The method of claim 43 wherein the metal is selected from the group consisting of transition metals, lanthanides, auger-electron emitting isotopes, and α-, β- or γ-emitting isotopes.

45. The method of claim 44 wherein X is selected from the group consisting of DOTA, DTPA, S4, N3S, N2S2, NS3 and derivatives thereof.

46. The method of claim 45 wherein X is N3S or a derivative thereof.

47. The method of claim 46 wherein Y is selected is selected from the group consisting of at least one amino acid residue, a hydrocarbon chain and a combination thereof and B is selected from the group consisting of BBN(7–14) and BBN (8–14).

48. The method of claim 47 wherein Y is gly-ser-gly.

49. A method of forming a therapeutic or diagnostic compound comprising the step of reacting a metal complexed with a chelating group with a GRP receptor agonist the receptor against including a bombesin agonist moiety.

50. The method of claim 49, wherein said method includes reacting a metal with a compound having a structure of the formula X-Y-B wherein X is a metal chelating group, Y is a spacer group or covalent bond and B is a gastrin releasing peptide receptor agonist which includes a bombesin agonist binding moiety.

51. The method of claim 50 wherein the metal is selected from the group consisting of transition metals, lanthanides, auger-electron emitting isotopes, and $\alpha$-, $\beta$- or $\Gamma$-emitting isotopes.

52. The method of claim 50 wherein the metal is selected from the group consisting of: 99mTc- and 186/188Re-.

53. The method of claim 52 wherein Y is selected is selected from the group consisting of at least one amino acid residue, a hydrocarbon chain and a combination thereof.

54. The method of claim 52 wherein X is selected from the group consisting of DOTA, DTPA, S4, N3S, N2S2, NS3 and derivatives thereof.

55. The method of claim 54 wherein B is selected from the group consisting of BBN(7–14) and BBN(8–14).

56. The method of claim 55 wherein X is DOTA or a derivative thereof and Y is selected from the group consisting of glycine, $\beta$-alanine, gamma-aminobutanoic acid, 5-aminovaleric acid (5-Ava), 6-aminohexanoic acid, 7-aminoheptanoic acid, 8-aminooctanoic acid (8-Aoc), 9-aminononanoic acid, 10-aminodecanoic acid and 11-aminoundecanoic acid (11-Aun).

57. The method of claim 55 wherein X is N3S or a derivative thereof and Y is gly-ser-gly.

* * * * *